US012692516B2

(12) United States Patent
Tagliatela et al.

(10) Patent No.: US 12,692,516 B2
(45) Date of Patent: *Jul. 28, 2026

(54) TISSUE SELECTIVE TRANSGENE EXPRESSION

(71) Applicant: Encoded Therapeutics, Inc., South San Francisco, CA (US)

(72) Inventors: Stephanie Tagliatela, South San Francisco, CA (US); Andrew Young, Redwood City, CA (US); Szu-Ying Chen, South San Francisco, CA (US); Kartik Ramamoorthi, South San Francisco, CA (US); David Oberkofler, South San Francisco, CA (US)

(73) Assignee: Encoded Therapeutics, Inc., South San Francisco, CA (US)

( * ) Notice: Subject to any disclaimer, the term of this patent is extended or adjusted under 35 U.S.C. 154(b) by 818 days.

This patent is subject to a terminal disclaimer.

(21) Appl. No.: 18/055,968

(22) Filed: Nov. 16, 2022

(65) Prior Publication Data
US 2023/0203531 A1 Jun. 29, 2023

Related U.S. Application Data

(63) Continuation of application No. 16/670,996, filed on Oct. 31, 2019, now abandoned, which is a continuation of application No. 16/153,433, filed on Oct. 5, 2018, now Pat. No. 10,519,465, which is a continuation of application No. PCT/US2018/025940, filed on Apr. 3, 2018.

(60) Provisional application No. 62/480,998, filed on Apr. 3, 2017.

(51) Int. Cl.
| | |
|---|---|
| *C12N 15/86* | (2006.01) |
| *A61K 48/00* | (2006.01) |
| *C07K 14/705* | (2006.01) |
| *C12N 15/113* | (2010.01) |
| *C12N 15/85* | (2006.01) |
| *C12N 15/864* | (2006.01) |

(52) U.S. Cl.
CPC .......... *C12N 15/86* (2013.01); *A61K 48/0058* (2013.01); *C07K 14/705* (2013.01); *C12N 15/113* (2013.01); *C12N 15/85* (2013.01); *C12N 15/8645* (2013.01); *A01K 2217/052* (2013.01); *A01K 2217/15* (2013.01); *A01K 2227/105* (2013.01); *A01K 2267/0312* (2013.01); *A61K 48/00* (2013.01); *C12N 2320/32* (2013.01); *C12N 2750/14143* (2013.01); *C12N 2830/008* (2013.01)

(58) Field of Classification Search
CPC ...... C12N 15/86; C12N 15/113; C12N 15/85; C12N 15/8645; C12N 2320/32; C12N 2750/14143; C12N 2830/008; A61K 48/0058; A61K 48/00; C07K 14/705; A01K 2217/052; A01K 2217/15; A01K 2227/105; A01K 2267/0312

USPC .................... 435/320.1; 536/24.1; 514/44 R; 424/199.1

See application file for complete search history.

(56) References Cited

U.S. PATENT DOCUMENTS

| | | | |
|---|---|---|---|
| 5,789,538 | A | 8/1998 | Rebar et al. |
| 5,925,523 | A | 7/1999 | Dove et al. |
| 6,007,988 | A | 12/1999 | Choo et al. |
| 6,013,453 | A | 1/2000 | Choo et al. |
| 6,140,081 | A | 10/2000 | Barbas |
| 6,180,613 | B1 | 1/2001 | Kaplitt et al. |
| 6,200,759 | B1 | 3/2001 | Dove et al. |
| 6,303,370 | B1 | 10/2001 | Kappen et al. |
| 6,372,500 | B1 | 4/2002 | Hu et al. |
| 6,436,708 | B1 | 8/2002 | Leone et al. |
| 6,453,242 | B1 | 9/2002 | Eisenberg et al. |
| 6,479,626 | B1 | 11/2002 | Kim et al. |
| 6,503,717 | B2 | 1/2003 | Case et al. |
| 6,503,888 | B1 | 1/2003 | Kaplitt et al. |
| 6,524,851 | B1 | 2/2003 | Ellis |
| 6,534,261 | B1 | 3/2003 | Cox, III et al. |
| 6,566,118 | B1 | 5/2003 | Atkinson et al. |
| 6,599,692 | B1 | 7/2003 | Case et al. |
| 6,607,882 | B1 | 8/2003 | Cox, III et al. |
| 6,649,371 | B1 | 11/2003 | Jentsch |
| 6,689,558 | B2 | 2/2004 | Case |
| 6,794,136 | B1 | 9/2004 | Eisenberg et al. |
| 6,812,339 | B1 | 11/2004 | Venter et al. |
| 6,903,185 | B2 | 6/2005 | Kim et al. |

(Continued)

FOREIGN PATENT DOCUMENTS

| | | |
|---|---|---|
| CA | 2985624 A1 | 6/2016 |
| CA | 3058189 A1 | 10/2018 |

(Continued)

OTHER PUBLICATIONS

Matsushita et al. (1998) Gene Therapy, vol. 5, 938-945.*

(Continued)

*Primary Examiner* — Anne Marie S Wehbe
(74) *Attorney, Agent, or Firm* — Wilson Sonsini Goodrich & Rosati

(57) ABSTRACT

Provided herein are compositions and methods for selective expression of a transgene. Compositions and methods for selective expression of a transgene comprise one or more human regulatory elements, which, when operably linked to a transgene, can facilitate selective expression of a transgene (for example, cell-type selective expression) in a target cell as compared to at least one or more non-target cells.

10 Claims, 14 Drawing Sheets

Specification includes a Sequence Listing.

(56)  References Cited

U.S. PATENT DOCUMENTS

| | | | |
|---|---|---|---|
| 6,933,113 B2 | 8/2005 | Case et al. | |
| 6,989,264 B2 | 1/2006 | Atkinson et al. | |
| 6,994,993 B2 | 2/2006 | Qin et al. | |
| 6,998,118 B2 | 2/2006 | Kaspar et al. | |
| 7,030,215 B2 | 4/2006 | Liu et al. | |
| 7,067,317 B2 | 6/2006 | Rebar et al. | |
| 7,070,934 B2 | 7/2006 | Cox, III et al. | |
| 7,094,600 B2 | 8/2006 | Wang | |
| 7,101,540 B2 | 9/2006 | Kaspar et al. | |
| 7,125,676 B2 | 10/2006 | George et al. | |
| 7,153,949 B2 | 12/2006 | Kim et al. | |
| 7,157,571 B2 | 1/2007 | Wang et al. | |
| 7,220,719 B2 | 5/2007 | Case et al. | |
| 7,253,273 B2 | 8/2007 | Collingwood | |
| 7,262,054 B2 | 8/2007 | Jamieson et al. | |
| 7,358,085 B2 | 4/2008 | Zhang et al. | |
| 7,361,635 B2 | 4/2008 | Miller et al. | |
| 7,534,775 B2 | 5/2009 | Zhang et al. | |
| 7,595,376 B2 | 9/2009 | Kim et al. | |
| 7,655,460 B2 | 2/2010 | Rouleau et al. | |
| 7,943,553 B2 | 5/2011 | Case et al. | |
| 7,947,837 B2 | 5/2011 | Marks et al. | |
| 8,137,948 B2 | 3/2012 | Qu et al. | |
| 8,143,005 B2 | 3/2012 | Rouleau et al. | |
| 8,304,235 B2 | 11/2012 | Passananti et al. | |
| 8,524,874 B2 | 9/2013 | Liu et al. | |
| 8,586,526 B2 | 11/2013 | Gregory et al. | |
| 8,772,453 B2 | 7/2014 | Paschon et al. | |
| 8,927,514 B2 | 1/2015 | Chatterjee et al. | |
| 8,969,077 B2 | 3/2015 | Head et al. | |
| 9,102,949 B2 | 8/2015 | Gao et al. | |
| 9,267,151 B2 | 2/2016 | Guerrero et al. | |
| 9,315,825 B2 | 4/2016 | Wilson et al. | |
| 9,624,498 B2 | 4/2017 | Froelich et al. | |
| 9,845,481 B2 | 12/2017 | Marengo et al. | |
| 10,000,757 B2 | 6/2018 | Naldini et al. | |
| 10,287,607 B2 * | 5/2019 | Tagliatela | A61P 25/28 |
| 10,287,608 B2 * | 5/2019 | Tagliatela | C12N 15/86 |
| 10,519,465 B2 * | 12/2019 | Tagliatela | A61P 25/28 |
| 12,083,188 B2 | 9/2024 | Tagliatela et al. | |
| 2002/0115215 A1 | 8/2002 | Wolffe et al. | |
| 2002/0165356 A1 | 11/2002 | Barbas et al. | |
| 2003/0017139 A1 | 1/2003 | Souza et al. | |
| 2003/0051266 A1 | 3/2003 | Serafini | |
| 2003/0082552 A1 | 5/2003 | Wolffe et al. | |
| 2004/0096885 A1 | 5/2004 | Rouleau et al. | |
| 2004/0191791 A1 | 9/2004 | Wallace et al. | |
| 2004/0258666 A1 | 12/2004 | Passini et al. | |
| 2005/0026169 A1 | 2/2005 | Cargill et al. | |
| 2005/0032219 A1 | 2/2005 | Aubourg et al. | |
| 2005/0064474 A1 | 3/2005 | Urnov et al. | |
| 2005/0196754 A1 | 9/2005 | Drmanac et al. | |
| 2005/0228172 A9 | 10/2005 | Wang | |
| 2005/0260576 A1 | 11/2005 | George, Jr. et al. | |
| 2005/0267061 A1 | 12/2005 | Martin | |
| 2006/0292572 A1 | 12/2006 | Stuart et al. | |
| 2007/0161031 A1 | 7/2007 | Trinklein et al. | |
| 2007/0218528 A1 | 9/2007 | Miller | |
| 2009/0018031 A1 | 1/2009 | Trinklein et al. | |
| 2009/0062135 A1 | 3/2009 | Delfour et al. | |
| 2009/0311222 A1 | 12/2009 | Baraban et al. | |
| 2010/0086532 A1 | 4/2010 | Barbas, III et al. | |
| 2010/0130594 A1 | 5/2010 | Barkats | |
| 2011/0015122 A1 | 1/2011 | Zimmerman et al. | |
| 2011/0065100 A1 | 3/2011 | Aldred et al. | |
| 2011/0135611 A1 | 6/2011 | Huang et al. | |
| 2011/0165129 A1 | 7/2011 | Kriegstein et al. | |
| 2011/0203007 A1 | 8/2011 | Klein et al. | |
| 2011/0268747 A1 | 11/2011 | Guerrero Martinez et al. | |
| 2013/0096183 A1 | 4/2013 | Collard et al. | |
| 2013/0224836 A1 | 8/2013 | Muramatsu | |
| 2013/0254909 A1 | 9/2013 | Marengo et al. | |
| 2014/0037585 A1 | 2/2014 | Wright et al. | |
| 2014/0142160 A1 | 5/2014 | Lee et al. | |
| 2014/0162894 A1 | 6/2014 | Hatchwell et al. | |
| 2015/0035917 A1 | 2/2015 | Asauchi | |
| 2015/0044187 A1 | 2/2015 | Visel et al. | |
| 2015/0071903 A1 | 3/2015 | Liu et al. | |
| 2015/0111955 A1 | 4/2015 | High et al. | |
| 2015/0253339 A1 | 9/2015 | Shekdar | |
| 2015/0273029 A1 | 10/2015 | Gruber et al. | |
| 2015/0353917 A1 | 12/2015 | Miller | |
| 2016/0032319 A1 | 2/2016 | Wright et al. | |
| 2016/0046681 A1 | 2/2016 | Neutzner et al. | |
| 2016/0120960 A1 | 5/2016 | Mcivor et al. | |
| 2017/0166903 A1 | 6/2017 | Zhang et al. | |
| 2017/0218037 A1 | 8/2017 | Passananti et al. | |
| 2018/0126003 A1 | 5/2018 | Hoerr | |
| 2019/0024118 A1 | 1/2019 | Tagliatela et al. | |
| 2019/0024119 A1 | 1/2019 | Tagliatela et al. | |
| 2019/0024120 A1 | 1/2019 | Tagliatela et al. | |
| 2019/0024121 A1 | 1/2019 | Tagliatela et al. | |
| 2020/0165628 A1 | 5/2020 | Tagliatela et al. | |
| 2022/0193264 A1 | 6/2022 | Wood et al. | |
| 2024/0408242 A1 | 12/2024 | Tagliatela et al. | |

FOREIGN PATENT DOCUMENTS

| | | |
|---|---|---|
| CL | 2014000550 A1 | 9/2014 |
| CN | 106170295 A | 11/2016 |
| CN | 107759673 A | 3/2018 |
| EP | 1590467 B1 | 10/2009 |
| EP | 2130838 A2 | 12/2009 |
| EP | 1747277 B1 | 8/2011 |
| EP | 2698163 A1 | 2/2014 |
| EP | 3119878 A2 | 1/2017 |
| JP | 2018088888 A | 6/2018 |
| KR | 20120087860 A | 8/2012 |
| TW | 201514202 A | 4/2015 |
| TW | 201925474 A | 7/2019 |
| WO | WO-9519431 A1 | 7/1995 |
| WO | WO-9606166 A1 | 2/1996 |
| WO | WO-9853057 A1 | 11/1998 |
| WO | WO-9853058 A1 | 11/1998 |
| WO | WO-9853059 A1 | 11/1998 |
| WO | WO-9853060 A1 | 11/1998 |
| WO | WO-9854311 A1 | 12/1998 |
| WO | WO-0027878 A1 | 5/2000 |
| WO | WO-0130843 A1 | 5/2001 |
| WO | WO-0136620 A2 | 5/2001 |
| WO | WO-0138362 A2 | 5/2001 |
| WO | WO-0160970 A2 | 8/2001 |
| WO | WO-0185938 A1 | 11/2001 |
| WO | WO-0188197 A2 | 11/2001 |
| WO | WO-0216536 A1 | 2/2002 |
| WO | WO-02057294 A2 | 7/2002 |
| WO | WO-02066640 A2 | 8/2002 |
| WO | WO-02099084 A2 | 12/2002 |
| WO | WO-03016496 A2 | 2/2003 |
| WO | WO-03066828 A2 | 8/2003 |
| WO | WO-03076601 A1 | 9/2003 |
| WO | WO-2005042728 A2 | 5/2005 |
| WO | WO-2006108846 A1 | 10/2006 |
| WO | WO-2007069666 A1 | 6/2007 |
| WO | WO-2007078599 A2 | 7/2007 |
| WO | WO-2008073303 A2 | 6/2008 |
| WO | WO-2008118820 A2 | 10/2008 |
| WO | WO-2008129058 A1 | 10/2008 |
| WO | WO-2008142124 A1 | 11/2008 |
| WO | WO-2009044383 A1 | 4/2009 |
| WO | WO-2009060316 A2 | 5/2009 |
| WO | WO-2010037143 A1 | 4/2010 |
| WO | WO-2010148143 A1 | 12/2010 |
| WO | WO-2012087983 A1 | 6/2012 |
| WO | WO-2013033627 A2 | 3/2013 |
| WO | WO-2013123503 A1 | 8/2013 |
| WO | WO-2014161884 A2 | 10/2014 |
| WO | WO-2015143046 A2 | 9/2015 |
| WO | WO-2015153760 A2 | 10/2015 |
| WO | WO-2016164609 A2 | 10/2016 |
| WO | WO-2016172155 A1 | 10/2016 |
| WO | WO-2016188112 A1 | 12/2016 |
| WO | WO-2017048466 A1 | 3/2017 |
| WO | WO-2017075335 A1 | 5/2017 |

(56) References Cited

FOREIGN PATENT DOCUMENTS

| WO | WO-2017075338 A2 | 5/2017 |
| WO | WO-2017106377 A1 | 6/2017 |
| WO | WO-2017151884 A1 | 9/2017 |
| WO | WO-2017180915 A2 | 10/2017 |
| WO | WO-2018049079 A1 | 3/2018 |
| WO | WO-2018126116 A1 | 7/2018 |
| WO | WO-2018148256 A1 | 8/2018 |
| WO | WO-2018187363 A1 | 10/2018 |
| WO | WO-2018213786 A1 | 11/2018 |
| WO | WO-2019109051 A1 | 6/2019 |
| WO | WO-2019224864 A1 | 11/2019 |
| WO | WO-2020243651 A1 | 12/2020 |

OTHER PUBLICATIONS

O'Connor et al. (2015) Trends Mol. Med., vol. 21(8), 504-512.*
Piguet et al. (2017) Human Gene Ther., vol. 28(11), 998-1003,.*
Gataullina et al. (2017) Seizure, vol. 44, 58-64.*
Grieger et al.: Production of Recombinant Adeno-associated Virus Vectors Using Suspension HEK293 Cells and Continuous Harvest of Vector From the Culture Media for GMP FIX and FLT1 Clinical Vector. Mol. Ther. 24(2):287-297 (2016).
Aach et al. CasFinder: Flexible algorithm for identifying specific Cas9 targets in genomes. BioRxiv, Cold Spring Harbor Labs. Posted May 12, 2014. doi: https://doi.org/10.1101/005074. Retrieved Sep. 10, 2020 at URL: https://doi.org/10.1101/005074. 8 pages.
Altschul, et al. Basic local alignment search tool. J Mol Biol. Oct. 5, 1990;215(3):403-410. doi: 10.1016/S0022-2836(05)80360-2.
Altschul, et al. Gapped BLAST and PSI-BLAST: a new generation of protein database search programs. Nucleic Acids Res. Sep. 1, 1997; 25(17):3389-3402. doi: 10.1093/nar/25.17.3389.
Anderson. Human gene therapy. Science. May 8, 1992;256(5058):808-13. doi: 10.1126/science.1589762.
Ayuso et al. Production, purification and characterization of adeno-associated vectors. Curr Gene Ther. Dec. 2010;10(6):423-36. doi: 10.2174/156652310793797685.
Bae et al. Cas-OFFinder: a fast and versatile algorithm that searches for potential off-target sites of Cas9 RNA-guided endonucleases. Bioinformatics, vol. 30, Issue 10, May 15, 2014, pp. 1473-1475, https://doi.org/10.1093/bioinformatics/btu048. Published online Jan. 24, 2014.
Bae et al.: Human zinc fingers as building blocks in the construction of artificial transcription factors. Nat Biotechnol. 21(3):275-280 doi: 10.1038/nbt796 (2003).
Bagot et al., Epigenetic signaling in psychiatric disorders: stress and depression, Dialogues Clin Neurosci., 16(3): 281-295 (2014).
Beerli, et al. Engineering polydactyl zinc-finger transcription factors. Nat Biotechnol. Feb. 2002;20(2):135-141. doi: 10.1038/nbt0202-135.
Beerli et al. Positive and negative regulation of endogenous genes by designed transcription factors. PNAS 97(4):1495-1500 (Feb. 15, 2000).
Bender et al.: SCN1A mutations in Dravet syndrome: impact of interneuron dysfunction on neural networks and cognitive outcome. Epilepsy Behav. 3(3):177-186 doi:10.1016/j.yebeh.2011.11.022 (2012).
Bezzina et al., Early Onset of Hypersynchronous Network Activity and Expression of a Marker of Chronic Seizures in the Tg2576 Mouse Model of Alzheimer's Disease, PLoS ONE 10(3): e0119910 (14 pages) (2015).
Blouin et al. Improving rAAV production and purification: towards the definition of a scaleable process. J Gene Med. Feb. 2004;6 Suppl 1:S223-8. doi: 10.1002/jgm.505.
Büning et a. Recent developments in adeno-associated virus vector technology. J Gene Med. Jul. 2008;10(7):717-33. doi: 10.1002/jgm. 1205.
Cermak, et al. Efficient design and assembly of custom TALEN and other TAL effector-based constructs for DNA targeting. Nucleic Acids Res. 39.12 (Jul. 2011): e82. doi: 10.1093/nar/gkr218. Epub Apr. 14, 2011.

Challis et al., Raphe GABAergic Neurons Mediate the Acquisition of Avoidance after Social Defeat, The Journal of Neuroscience, 33(35):13978-13988 (2013).
Cheah et al., Specific deletion of Nav1.1 sodium channels in inhibitory interneurons causes seizures and premature death in a mouse model of Dravet syndrome, Proc Natl Acad Sci, 109(36): 14646-14651 (2012).
Choo, et al. Advances in zinc finger engineering. Curr Opin Struct Biol. Aug. 2000;10(4):411-416. doi: 10.1016/s0959-440x(00)00107-x.
Colasante, et al. dCas9-Based Scn1a Gene Activation Restores Inhibitory Interneuron Excitability and Attenuates Seizures in Dravet Syndrome Mice. Mol Ther. Jan. 8, 2020;28(1):235-253. doi: 10.1016/j.ymthe.2019.08.018. Epub Sep. 3, 2019.
Connelly. Dravet Syndrome: Diagnosis and Long-Term Course. Can J Neurol Sci. 43: S3-S8 (2016).
Conway et al. Recombinant adeno-associated virus type 2 replication and packaging is entirely supported by a herpes simplex virus type 1 amplicon expressing Rep and Cap. J Virol. Nov. 1997; 71(11): 8780-8789.
CRISPR-Cas9 Epigenome Editing Screen Reveals Regulatory Elements. GenomeWeb. 3 pages. Apr. 3, 2017. Retrieved Nov. 6, 2018 at URL: https://www.genomeweb.com/epigenetics-research/crispr-cas9-epigenome-editing-screen- reveals-regulato . . . .
Desjarlais et al., Use of a Zinc-Finger Consensus Sequence Framework and Specificity Rules to Design Specific DNA Binding Proteins. Proceedings of the National Academy of Sciences of the United States of America, 90.6 (Mar. 1993): 2256-2260.
Dillon. Regulating gene expression in gene therapy. Trends Biotechnol 11(5):167-173 (1993).
Dimidschstein et al. A viral strategy for targeting and manipulating interneurons across vertebrate species. Nat Neurosci. 19(12): 1743-1749 (Dec. 2016). doi:10.1038/nn.4430.
Dingwall et al. The nucleoplasmin nuclear location sequence is larger and more complex than that of SV-40 large T antigen. J Cell Biol. Sep. 1, 1988; 107(3): 841-849. doi: 10.1083/jcb.107.3.841.
Doench et al. Optimized sgrNA design to maximize activity and minimize off-target effects of crisPr-cas9. Nature Biotechnology 34(2):184-191 (Feb. 2016). Advance Online Publication published online Jan. 18, 2016. doi: 10.1038/nbt/3437.
EBI. EMBOSS Needle. Available at http://www.ebi.ac.uk/Tools/psa/emboss_needle/. Accessed on Dec. 20, 2016.
Eguchi, et al. Reprogramming cell fate with a genome-scale library of artificial transcription factors. Proc Natl Acad Sci USA. Dec. 20, 2016;113(51):E8257-E8266. doi: 10.1073/pnas.1611142114. Epub Dec. 5, 2016.
EMBL-EBI. EMBOSS Water Pairwise Sequence Alignment. Smith-Waterman algorithm. Accessed on Sep. 30, 2020. 2 pages. Available at https://www.ebi.ac.uk/Tools/psa/emboss_water.
Eriksen, et al. Progranulin: normal function and role in neurodegeneration. J Neurochem. Jan. 2008;104(2):287-97. Epub Oct. 22, 2007.
European search report and opinion dated Nov. 26, 2020 for EP Application No. 18781685.5.
Feng et al. Imaging Neuronal Subsets in Transgenic Mice Expressing Multiple Spectral Variants of GFP. Neuron 28:41-51 (Oct. 2000).
Frye et al., Neuropathological Mechanisms of Seizures in Autism Spectrum Disorder, Frontiers in Neuroscience, 10:192 (9 pages) (2016).
Geißler, et al. Transcriptional activators of human genes with programmable DNA-specificity. PLoS One. 2011;6(5):e19509. doi: 10.1371/journal.pone.0019509. Epub May 19, 2011.
GenBank Accession No. GCA_000001405.27 (replaced). RefSeq Accession: GCF_000001405.38 (replaced). GRCh38.p12. Date: Dec. 21, 2017. 3 pages. Retrieved Feb. 10, 2021 at URL: https://www.ncbi.nlm.nih.gov/assembly/GCF_000001405.38/.
GenBank Accession No. NC_000017. Version No. NC_000017.11. *Homo sapiens* chromosome 17, GRCh38.p13 Primary Assembly. Record created Aug. 29, 2002. 2 pages. Retrieved Feb. 10, 2021 at URL: https://www.ncbi.nlm.nih.gov/nuccore/NC_000017.
GenBank Accession No. NM_001032221. Version No. NM_001032221.3. *Homo sapiens* syntaxin binding protein 1 (STXBP1), transcript

(56)        References Cited

OTHER PUBLICATIONS variant 2, mRNA. Record created Aug. 25, 2005. 5 pages. Retrieved Feb. 10, 2021 at URL: https://www.ncbi.nlm.nih.gov/nuccore/NM_001032221.3.

GenBank Accession No. NM_001037 XM_940055. Version No. NM_001037.4. *Homo sapiens* sodium voltage-gated channel beta subunit 1 (SCN1B), transcript variant a, mRNA. Record created Mar. 24, 1999. 4 pages. Retrieved Feb. 10, 2021 at URL: https://www.ncbi.nlm.nih.gov/nuccore/NM_001037.4.

GenBank Accession No. NM_001112741. Version No. NM_001112741.1. *Homo sapiens* potassium voltage-gated channel subfamily C member 1 (KCNC1), transcript variant 1, mRNA. Record created Dec. 20, 2007. 5 pages. Retrieved Feb. 10, 2021 at URL: https://www.ncbi.nlm.nih.gov/nuccore/NM_001112741.1.

GenBank Accession No. NM_001165963. Version No. NM_001165963.1. *Homo sapiens* sodium voltage-gated channel alpha subunit 1 (SCN1A), transcript variant 1, mRNA. Record created Oct. 1, 2009. 9 pages. Retrieved Feb. 10, 2021 at URL: https://www.ncbi.nlm.nih.gov/nuccore/NM_001165963.1.

GenBank Accession No. NM_002087. Version No. NM_002087.3. *Homo sapiens* granulin precursor (GRN), mRNA. Record created Mar. 24, 1999. 5 pages. Retrieved Feb. 10, 2021 at URL: https://www.ncbi.nlm.nih.gov/nuccore/NM_002087.3.

GenBank Accession No. NM_004588. Version No. NM_004588.4. *Homo sapiens* sodium voltage-gated channel beta subunit 2 (SCN2B), mRNA. Record created May 7, 1999. 5 pages. Retrieved Feb. 10, 2021 at URL: https://www.ncbi.nlm.nih.gov/nuccore/NM_004588.4.

GenBank Accession No. NM_004977. Version No. NM_004977.2. *Homo sapiens* potassium voltage-gated channel subfamily C member 3 (KCNC3), transcript variant 1, mRNA. Record created May 14, 1999. 5 pages. Retrieved Feb. 10, 2021 at URL: https://www.ncbi.nlm.nih.gov/nuccore/NM_004977.2.

GenBank Accession No. XM_005257253. Version No. XM_005257253.1. Predicted: *Homo sapiens* granulin precursor (GRN), transcript variant X1, mRNA. Record created Aug. 13, 2013. 2 pages. Retrieved Feb. 10, 2021 at URL: https://www.ncbi.nlm.nih.gov/nuccore/XM_005257253.1.

GenBank Accession No. AC007405. *Homo sapiens* BAC clone RP11-570C16 from 2, complete sequence. Washington University Genome Sequencing Center. Priority to at least Apr. 30, 2005.

Genome Reference Consortium Accession No. AL589692. Mouse DNA sequence from clone RP23-385C1 on chromosome 15, complete sequence. Wellcome Trust Sanger Institute. Submitted Dec. 13, 2012.

Gersbach et al. Synthetic Zinc Finger Proteins: The Advent of Targeted Gene Regulation and Genome Modification Technologies. Acc Chem Res. Aug. 19, 2014; 47(8): 2309-2318. Published online May 30, 2014. doi: 10.1021/ar500039w.

Ghidoni, et al. Circulating progranulin as a biomarker for neurodegenerative diseases. Am J Neurodegener Dis. 2012;1(2):180-90. Epub Aug. 2, 2012.

Gonzalez, et al. Modular system for the construction of zinc-finger libraries and proteins. Nat Protoc. Apr. 2010;5(4):791-810. doi: 10.1038/nprot.2010.34. Epub Apr. 1, 2010.

Gratz et al. Highly Specific and Efficient CRISPR/Cas9-Catalyzed Homology-Directed Repair in *Drosophila*. Genetics. Apr. 2014; 196(4): 961-971. Published online Jan. 29, 2014. doi: 10.1534/genetics.113.160713.

Gray et al., Optimizing Promoters for Recombinant Adeno-Associated Virus-Mediated Gene Expression in the Peripheral and Central Nervous System Using Self-Complementary Vectors, Human Gene Therapy, 22:1143-1153 (2011).

Grimm et al. Helper virus-free, optically controllable, and two-plasmid-based production of adeno-associated virus vectors of serotypes 1 to 6. Mol Ther. Jun. 2003;7(6):839-50. doi: 10.1016/s1525-0016(03)00095-9.

Haddada, et al. Gene therapy using adenovirus vectors. The Molecular Repertoire of Adenoviruses III. Curr Top Microbiol Immunol. 1995;199 (Pt 3):297-306. doi: 10.1007/978-3- 642-79586-2_14.

Han et al., Autistic behavior in Scn1a+/- mice and rescue by enhanced GABAergic transmission, Nature, 489(7416): 385-390 (2012).

Han et al., Enhancement of Inhibitory Neurotransmission by GABAA Receptors Having α2,3-Subunits Ameliorates Behavioral Deficits in a Mouse Model of Autism, Neuron, 81(6): 1282-1289 (2014).

Hawkins et al. The synthetic neuroactive steroid SGE-516 reduces seizure burden and improves survival in a Dravet syndrome mouse model. Scientific Reports 7:15327. Published online Nov. 10, 2017. 8 pages. DOI: 10.1038/s41598-017-15609-w.

Hedrich et al., Impaired Action Potential Initiation in GABAergic Interneurons Causes Hyperexcitable Networks in an Epileptic Mouse Model Carrying a Human Nav1.1 Mutation, The Journal of Neuroscience, 34(45): 14874-14889 (2014).

Heigwer et al. E-CRISP: fast CRISPR target site identification. Nat Methods. Feb. 2014;11(2):122-3. doi: 10.1038/nmeth.2812.

Heilbronn, et al. Viral vectors for gene transfer: current status of gene therapeutics. Handb Exp Pharmacol. 2010;(197):143-170. doi: 10.1007/978-3-642-00477-3_5.

Hocquemiller et al. Adeno-Associated Virus-Based Gene Therapy for CNS Diseases. Human Gene Therapy 27(7):478-496 (2016).

Hossain et al.: Artificial zinc finger DNA binding domains: versatile tools for genome engineering and modulation of gene expression. J Cell Biochem. 116(11):2435-2444 doi:10.1002/jcb.25226 (2015).

International search report with written opinion dated Feb. 14, 2019 for PCT/US2018/063498.

International search report with written opinion dated Aug. 28, 2020 for PCT/US2020/035431.

Irizarry et al., Incidence of New-Onset Seizures in Mild to Moderate Alzheimer Disease, Arch Neurol., 69(3): 368-372 (2012).

Isalan, et al. A rapid, generally applicable method to engineer zinc fingers illustrated by targeting the HIV-1 promoter. Nat Biotechnol. Jul. 2001;19(7):656-660. doi: 10.1038/90264.

Karlin, et al. Applications and statistics for multiple high-scoring segments in molecular sequences. PNAS USA 90:5873-5877 (1993).

Karlin, et al. Applications and statistics for multiple high-scoring segments in molecular sequences. Proc Natl Acad Sci USA. Jun. 15, 1993; 90(12):5873-5877. doi: 10.1073/pnas.90.12.5873.

Karlin et al. Methods for assessing the statistical significance of molecular sequence features by using general scoring schemes. PNAS USA 87:2264-2268 (1990).

Karlin, et al. Methods for assessing the statistical significance of molecular sequence features by using general scoring schemes. Proc Natl Acad Sci USA. Mar. 1990; 87(6): 2264-2268. doi: 10.1073/pnas.87.6.2264.

Khan et al. Computational tools and resources for prediction and analysis of gene regulatory regions in the chick genome. Genesis 51(5):311-324 (May 2013).

Kovacs et al., Alzheimer's secretases regulate voltage-gated sodium channels, Neurosci Lett., 486(2): 68-72 (2010).

Kremer et al. Adenovirus and adeno-associated virus mediated gene transfer. Br Med Bull. 51(1):31-44 (1995).

Kurien, et al. A brief review of other notable protein detection methods on acrylamide gels. Methods Mol Biol. 2012;869:617-620. doi: 10.1007/978-1-61779-821-4_56.

Lambert et al. The Human Transcription Factors. Cell 172:650-665 (Feb. 8, 2018).

Ledri et al. Global Optogenetic Activation of Inhibitory Interneurons during Epileptiform Activity. Journal of Neuroscience 34(9):3364-3377 (Feb. 26, 2014). DOI: https://doi.org/10.1523/JNEUROSCI.2734-13.2014.

Lee et al. Transcriptional Regulation and its Misregulation in Disease. Cell 152(6):1237-1251. doi: 10.1016/j.cell.2013.02.014.

Lee et al. The Largest Group of Superficial Neocortical GABAergic Interneurons Expresses Ionotropic Serotonin Receptors. Journal of Neuroscience 30(50):16796-16808 (Dec. 15, 2010). DOI: https://doi.org/10.1523/JNEUROSCI.1869-10.2010.

Li et al. Modularly assembled designer TAL effector nucleases for targeted gene knockout and gene replacement in eukaryotes. Nucleic Acids Res. Aug. 2011; 39(14): 6315-6325. Published online Mar. 31, 2011. doi: 10.1093/nar/gkr188.

(56)          References Cited

OTHER PUBLICATIONS

Liu, et al. CRISPR-ERA: a comprehensive design tool for CRISPR-mediated gene editing, repression and activation. Bioinformatics. 31 (22). 2015. pp. 3676-3678.

Liu et al. Design of polydactyl zinc-finger proteins for unique addressing within complex genomes. Proc Natl Acad Sci U S A. May 27, 1997;94(11):5525-30. doi: 10.1073/pnas.94.11.5525.

Lock et al. Absolute determination of single-stranded and self-complementary adeno-associated viral vector genome titers by droplet digital PCR. Hum Gene Ther Methods 25(2):115-125 (2014).

Lock et al. Characterization of a recombinant adeno-associated virus type 2 Reference Standard Material. Hum Gene Ther. Oct. 2010;21(10):1273-85. doi: 10.1089/hum.2009.223.

Ma, et al. A guide RNA sequence design platform for the CRISPR/Cas9 system for model organism genomes. Biomed Res Int. 2013;2013:270805. doi: 10.1155/2013/270805. Epub Oct. 3, 2013. 4 pages.

Maguire et al. Gene Therapy for the Nervous System: Challenges and New Strategies. Neurotherapeutics 11:817-839 (Aug. 27, 2014). DOI: 10.1007/s13311-014-0299-5.

Makkerh et al.: Comparative mutagenesis of nuclear localization signals reveals the importance of neutral and acidic amino acids. Curr Biol. Aug. 1, 1996;6(8):1025-1027. doi: 10.1016/s0960-9822(02)00648-6.

Mandell, et al. Zinc Finger Tools: custom DNA-binding domains for transcription factors and nucleases. Nucleic Acids Res. Jul. 1, 2006;34(Web Server issue):W516-W523. doi: 10.1093/nar/gkl209.

Marini et al. The genetics of Dravet syndrome. Epilepsia 52(Suppl. 2):24-29 (2011).

McLean et al., Widespread neuron-specific transgene expression in brain and spinal cord following synapsin promoter-driven AAV9 neonatalintracerebroventricular injection, Neuroscience Letters, 576: 73-78 (2014).

Meyer et al. In vivo labeling of parvalbumin-positive interneurons and analysis of electrical coupling in identified neurons. J Neurosci 22(16):7055-7064 (Aug. 15, 2002).

Miller, et al. From Gene Replacement to Gene Regulation: Developing a Disease-Modifying AAV Gene Therapy Vector for SCN1A-Positive (SCN1A+) Pediatric Epilepsy. American Epilepsy Association Annual Meeting Abstracts. Abstract 1.091. Published Nov. 2019. (online journal) Retrieved from the internet on Feb. 10, 2021. URL: https://www.aesnet.org/meetings_events/annual_meeting_abstracts/view/2421087.

Miller et al. Mapping genetic modifiers of survival in a mouse model of Dravet syndrome. Genes, Brain and Behavior 13:163-172 (Feb. 2014). First published Oct. 23, 2013. doi: 10.1111/gbb.12099.

Miller. Human gene therapy comes of age. Nature 357:455-460 (1992).

Mitani et al. Delivering therapeutic genes-matching approach and application Trends Biotechnol 11:162-166 (1993).

Mo et al. Epigenomic Signatures of Neuronal Diversity in the Mammalian Brain. Neuron 86:1369-1384 (Jun. 17, 2015).

Mo et al. Supplemental Information: Epigenomic Signatures of Neuronal Diversity in the Mammalian Brain. Neuron 86(6) (Jun. 17, 2015). 30 pages.

Montague et al. CHOPCHOP: a CRISPR/Cas9 and TALEN web tool for genome editing. Nucleic Acids Res. Jul. 1, 2014; 42(Web Server issue): W401-W407. Published online May 26, 2014. doi: 10.1093/nar/gku410.

Morbitzer et al. Assembly of custom TALE-type DNA binding domains by modular cloning. Nucleic Acids Res. Jul. 2011; 39(13): 5790-5799. Published online Mar. 1, 20118. doi: 10.1093/nar/gkr151.

Nabel, et al. Direct gene transfer for immunotherapy and immunization. Trends Biotechnol. May 1993;11(5):211-215. doi: 10.1016/0167-7799(93)90117-R.

Narlikar et al. Identifying regulatory elements in eukaryotic genomes. Briefings in Functional Genomics and Proteomics 8(4):215-230 (Jun. 4, 2009).

Nathanson et al., Short promoters in viral vectors drive selective expression in mammalian inhibitory neurons, but do not restrict activity to specifi c inhibitory cell-types, Frontiers in Neural Circuits, 3(19): 1-24 (2009).

NCBI. Basic Local Alignment Search Tool. BLAST algorithm. Available at https://blast.ncbi.nlm.nih.gov/Blast.cgi. Accessed on Jan. 3, 2017.

Nguyen, et al. Progranulin: at the interface of neurodegenerative and metabolic diseases. Trends Endocrinol Metab. Dec. 2013;24(12):597-606. doi: 10.1016/j.tem.2013.08.003. Epub Sep. 10, 2013.

Niels Van Tol et al. Artificial transcription factor-mediated regulation of gene expression. Plant Science 225:58-67 (2014).

Oakley, et al. Temperature- and age-dependent seizures in a mouse model of severe myoclonic epilepsy in infancy. Proc Natl Acad Sci USA. Mar. 10, 2009;106(10):3994-9. doi: 10.1073/pnas.0813330106. Epub Feb. 20, 2009.

Ogiwara et al., Nav1.1 haploinsufficiency in excitatory neurons ameliorates seizure-associated sudden death in a mouse model of Dravet syndrome, Human Molecular Genetics, 22(23): 4784-4804 (2013).

Ogiwara et al. Nav1.1 Localizes to Axons of Parvalbumin-Positive Inhibitory Interneurons: A Circuit Basis for Epileptic Seizures in Mice Carrying an Scn1a Gene Mutation. The Journal of Neuroscience 27(22):5903-5914 (May 30, 2007).

Oliva Jr. et al. Novel Hippocampal Interneuronal Subtypes Identified Using Transgenic Mice That Express Green Fluorescent Protein in GABAergic Interneurons. The Journal of Neuroscience 20(9):3354-3368 (May 1, 2000).

Onori et al. UtroUp is a novel six zinc finger artificial transcription factor that recognises 18 base pairs of the utrophin promoter and efficiently drives utrophin upregulation. BMC Molecular Biology 14:3 (2013). 9 pages.

Pabo, et al. Design and selection of novel Cys2His2 zinc finger proteins. Annu Rev Biochem. 2001;70:313-340. doi: 10.1146/annurev.biochem.70.1.313.

Palop et al., Aberrant Excitatory Neuronal Activity and CompensatoryRemodelingof InhibitoryHippocampal Circuits in MouseModels of Alzheimer's Disease, Neuron, 55: 697-711 (2007).

Palop et al., Epilepsy and Cognitive Impairments in Alzheimer Disease, Arch Neurol., 66(4): 435 (11 pages) (2009).

Papworth et al. Designer zinc-finger proteins and their applications. Gene 366:27-38 (2006).

PCT/US2018/025940 International Search Report and Written Opinion dated Aug. 23, 2018.

Pelkey et al. Hippocampal GABAergic Inhibitory Interneurons. Physiol Rev 97(4):1619-1747 (Oct. 1, 2017). DOI: 10.1152/physrev.00007.2017.

Puts et al., Reduced GABA and Altered Somatosensory Function in Children with Autism Spectrum Disorder, Autism Res., 10(4): 608-619 (2017).

PVALB (main page). The Human Protein Atlas. Available at https://www.proteinatlas.org/ENSG00000100362-PVALB/tissue. Accessed on Sep. 27, 2018.

Radde et al. Aβ42-driven cerebral amyloidosis in transgenic mice reveals early and robust pathology. EMBO reports 7(9):940-946 (Sep. 1, 2006). Published online Aug. 11, 2006. DOI 10.1038/sj.embor.7400784.

Ran et al. In vivo genome editing using *Staphylococcus aureus* Cas9. Nature. 520(7546):186-191 (2015).

Ray et al. Quantitative tracking of protein trafficking to the nucleus using cytosolic protein delivery by nanoparticle-stabilized nanocapsules. Bioconjug Chem. Jun. 17, 2015; 26(6): 1004-1007. Published online Jun. 2, 2015. doi: 10.1021/acs.bioconjchem.5b00141.

Reetz et al, Development of Adenoviral Delivery Systems to Target Hepatic Stellate Cells In Vivo, PLoS ONE 8(6): e67091, 14 pages (2013).

Ritter et al., Lentiviral expression of GAD67 and CCK promoterdriven opsins to target interneurons in vitro and in vivo, J Gene Med, 18: 27-37 (2016).

(56)            References Cited

OTHER PUBLICATIONS

Sander, et al. Zinc Finger Targeter (ZiFIT): an engineered zinc finger/target site design tool. Nucleic Acids Res. Jul. 2007;35(Web Server issue):W599-W605. doi: 10.1093/nar/gkm349. Epub May 25, 2007.
Schleef et al. The structure of the mouse parvalbumin gene. Mammalian Genome 3:217-225 (1992).
Scott et al. Targeted genome regulation and modification using transcription activator-like effectors. FEBS Journal 281:4583-4597 (2014). doi: 10.1111/febs.12973.
Segal, et al. Custom DNA-binding proteins come of age: polydactyl zinc-finger proteins. Curr Opin Biotechnol. Dec. 2001;12(6):632-637. doi: 10.1016/s0958-1669(01)00272-5.
Shevtsova et al., Promoters and serotypes: targeting of adeno-associated virus vectors for gene transfer in the rat central nervous system in vitro and in vivo, Exp Physiol 90.1 pp. 53-59 (2004).
Snowden, et al. Progranulin gene mutations associated with frontotemporal dementia and progressive non-fluent aphasia. Brain. Nov. 2006;129(Pt 11):3091-102. Epub Sep. 26, 2006.
Sohn et al., A Single Vector Platform for High-Level Gene Transduction of Central Neurons: Adeno-Associated Virus Vector Equipped with the Tet-Off System, PLoS ONE 12(1): e0169611, 22 pages, (2017).
Soukupova et al., Impairment of GABA release in the hippocampus at the time of the first spontaneous seizure in the pilocarpine model of temporal lobe epilepsy, Experimental Neurology, 257: 39-49 (2014).
Strimpakos et al. Novel Adeno-Associated Viral Vector Delivering the Utrophin Gene Regulator Jazz Counteracts Dystrophic Pathology in mdx Mice. J Cell Physiol 229:1283-1291 (2014).
Sun et al., SCN1A, SCN1B, and GABRG2 gene mutation analysis in Chinese families with generalized epilepsy with febrile seizures plus, J Hum Genet, 53:769-774 (2008).
Tai et al., Impaired excitability of somatostatin- and parvalbumin-expressing cortical interneurons in a mouse model of Dravet Syndrome, Proc Natl Acad Sci, 111(30): E3139-3148 (2014).
Tamamaki et al. Green flourescent protein expression and colocalization with calretinin, parvalbumin, and somatostatin in the GAD67-GFP knock-in mouse. J Comp Neurol 467(1):60-79 (Dec. 1, 2003).
Taniguchi et al., A Resource of Cre Driver Lines for Genetic Targeting of GABAergic Neurons in Cerebral Cortex, Neuron, 71: 995-1013 (2011).
Taniguchi, Genetic dissection of GABAergic neural circuits in mouse neocortex. Front Cell Neurosci vol. 8, Article 8 (Jan. 27, 2014). 22 pages. DOI: .https://doi.org/10.3389/fncel.2014.00008.
Uil et al. Therapeutic modulation of endogenous gene function by agents with designed DNA-sequence specificities. Nucleic Acids Research 31(21):6064-6078 (2003). DOI: 10.1093/nar/gkg815.
Urabe et al. Insect cells as a factory to produce adeno-associated virus type 2 vectors. Hum Gene Ther. Nov. 1, 2002;13(16):1935-43. doi: 10.1089/10430340260355347.
U.S. Appl. No. 16/670,996 Final Office Action dated Jun. 17, 2022.
U.S. Appl. No. 16/670,996 Non-Final Office Action mailed Dec. 8, 2021.
U.S. Appl. No. 16/153,401 Notice of Allowance dated Feb. 21, 2019.
U.S. Appl. No. 16/153,401 Office Action dated Jan. 11, 2019.
U.S. Appl. No. 16/153,420 Notice of Allowance dated Feb. 21, 2019.
U.S. Appl. No. 16/153,420 Office Action dated Dec. 14, 2018.
U.S. Appl. No. 16/153,433 Notice of Allowance dated Oct. 11, 2019.
U.S. Appl. No. 16/153,433 Office Action dated Dec. 31, 2018.
U.S. Appl. No. 16/153,433 Office Action dated Jul. 1, 2019.
U.S. Appl. No. 16/153,443 Office Action dated Jan. 11, 2019.
U.S. Appl. No. 16/153,443 Office Action dated Jul. 29, 2019.
U.S. Appl. No. 16/153,443 Office Action dated Mar. 5, 2020.
Van Brunt. Molecular Farming: Transgenic Animals as Bioreactors. Biotechnology (NY). 1988;6(10):1149-1154. doi: 10.1038/nbt1088-1149.
Van Den Pol et al. Selective neuronal expression of green fluorescent protein with cytomegalovirus promoter reveals entire neuronal arbor in transgenic mice. J Neurosci 18(24):10640-10651 (Dec. 15, 1998).
Verret et al., Inhibitory Interneuron Deficit Links Altered Network Activity and Cognitive Dysfunction in Alzheimer Model, Cell, 149(3): 708-721 (2012).
Vigne et al. Third-generation adenovectors for gene therapy. Restor Neurol Neurosci 8(1):35-36 (1995).
Weber, et al. Assembly of Designer TAL Effectors by Golden Gate Cloning, PLoS ONE, 6:e19722 (2001).
Wootton et al. Statistics of local complexity in amino acid sequences and sequence databases. Computers & Chemistry 17(2):149-163 (Jun. 1993).
Wright et al. Standardized reagents and protocols for engineering zinc finger nucleases by modular assembly. Nat Protoc. 2006;1(3):1637-52. doi: 10.1038/nprot.2006.259.
Wu et al. Target specificity of the CRISPR-Cas9 system. Quantitative Biology, vol. 2, pp. 59-70 (2014). Published: Aug. 26, 2014. DOI 10.1007/s40484-014-0030-x.
Xiao et al. CasOT: a genome-wide Cas9/gRNA off-target searching tool. Bioinformatics. Apr. 15, 2014;30(8):1180-1182.
Xiao, et al. Production of high-titer recombinant adeno-associated virus vectors in the absence of helper adenovirus. J Virol. Mar. 1998;72(3):2224-2232.
Xie et al., MicroRNA-regulated, Systemically Delivered rAAV9: A Step Closer to CNS-restricted Transgene Expression, Mol Ther., 19(3):526-535 (2011).
Xu et al. Immunochemical characterization of inhibitory mouse cortical neurons: Three chemically distinct classes of inhibitory cells. J Comp Neurol 518(3):389-404 (Feb. 1, 2010). doi: 10.1002/cne.22229.
Yan et al., Targeting the β secretase BACE1 for Alzheimer's disease therapy, Lancet Neurol., 13(3): 319-329 (2014).
Young et al. 915—a GABA-Selective AAV Vector-Based Approach to Up-Regulate Endogenous Scn1a Expression reverses key Phenotypes in a Mouse Model of Dravet Syndrome. 22nd Annual Meeting American Society of Gene & Cell Therapy. Washington, D.C. Apr. 29-May 2, 2019 (Abstract).
Young, et al. A GABA-Selective AAV Vector Upregulates Endogenous SCN1A Expression and Reverses Multiple Phenotypes in a Mouse Model of Dravet Syndrome. American Epilepsy Association Annual Meeting Abstracts. Abstract 3.1. Published Nov. 2019. (online journal) Retrieved from the Internet on Feb. 10, 2021. URL: https://www.aesnet.org/meetings_events/annual_meeting_abstracts/view/2421999.
Yu et al. Progress towards gene therapy for HIV infection. Gene Ther 1(1):13-26 (1994).
Yu, et al. The spectrum of mutations in progranulin: a collaborative study screening 545 cases of neurodegeneration. Arch Neurol. Feb. 2010;67(2):161-70. doi: 10.1001/archneurol.2009.328.
Zetsche, et al. Cpf1 is a single RNA-guided endonuclease of a class 2 CRISPR-Cas system. Cell. Oct. 22, 2015;163(3):759-771. doi: 10.1016/j.cell.2015.09.038. Epub Sep. 25, 2015.
Zhang et al. Efficient construction of sequence-specific TAL effectors for modulating mammalian transcription. Nature Biotechnology vol. 29, pp. 149-153 (Jan. 19, 2011).
Zuris et al. Efficient Delivery of Genome-Editing Proteins In Vitro and In Vivo, Nat Biotechnol., 33(1): 73-80 (Jan. 2015).
Sahenk et al. Systemic delivery of AAVrh74.tMCK.hCAPN3 rescues the phenotype in a mouse model for LGMD2A/R1. Mol Ther Methods Clin Dev 22:401-414 (2021).
PCT/US2018/025940 International Preliminary Report on Patentability dated Oct. 17, 2019.
Hsiao, J. et al., "Upregulation of Haploinsufficient Gene Expression in the Brain by Targeting a Long Non-coding RNA Improves Seizure Phenotype in a Model of Dravet Syndrome," EBioMedicine, 2016, vol. 9, pp. 257-277.
Fenzi Shengwuxue: Chapter 5 Protein Structure and Functions—Transcriptional Factors. Molecular Biology, Ed. Yu Duowei, Gong Zhunan, Liu Ping—Nanjing: Nanjing Normal University Press, College Teaching Materials, pp. 100-107 [English Translation provided] (2007).

(56) References Cited

OTHER PUBLICATIONS

Li et al.: The zinc-sensing mechanism of mouse MTF-1 involves linker peptides between the zinc fingers. Mol Cell Biol. 26(15):5580-5587 doi:10.1128/MCB.00471-06 (2006).

EP Serial No. 24175675.8 Extended European Search Report dated Sep. 5, 2024.

Chillon, Miguel, and A. Bosch. Adenovirus: Methods and Protocols, Third. Edition. Humana Press (2014).

Choi et al., A Generic Intron Increases Gene Expression in Transgenic Mice. Mol. Cell. Biol., 11(6):3070-3074 (1991).

Definition of Eukaryotic Expression Cassette (2023).

EP Serial No. 18803184 Extended European Search Report dated Feb. 22, 2021.

EP18803184.3 Partial Supplementary European Search Report dated Feb. 22, 2021.

EP18803184.3 Supplementary European Search Report dated May 26, 2021.

EP20815541.6 Supplementary European Search Report dated Jun. 13, 2023.

Furger et al.: Promoter proximal splice sites enhance transcription. Genes Dev. 16(21):2792-2799 doi:10.1101/gad.983602 (2002).

GenBank Accession: AAA52484 factor (1994).

GenBank Accession: K01740.1 Human coagulation factor (1994).

Le et al.: Classifying Promoters by Interpreting the Hidden Information of DNA Sequences via Deep Learning and Combination of Continuous FastText N-Grams. Front Bioeng Biotechnol. 7:305:1-9 doi:10.3389/fbioe.2019.00305 (2019).

Li et al., A small regulatory element from chromosome 19 enhances liver-specific gene expression. Gene Therapy 16:43-51 (2009).

Mcintosh et al., Therapeutic levels of FVIII following a single peripheral vein administration of rAAV vector encoding a novel human factor VIII variant. Blood 121(17):3335-3344 (2013).

Merten, Otto-Wilhelm, and Mohamed Al-Rubeai. Viral vectors for gene therapy: methods and protocols. Humana Press 737 (2011).

Morello et al.: Testing the IMEter on rice introns and other aspects of intron-mediated enhancement of gene expression. J Exp Bot. 62(2):533-544 doi:10.1093/jxb/erq273 (2011).

Ostedgaard, Lynda S. et al. A shortened adeno-associated virus expression cassette for CFTR gene transfer to cystic fibrosis airway epithelia. PNAS USA 102(8):2952-2957 (2005).

PCT/US2018/033515 International Preliminary Reporton Patentability dated Nov. 28, 2019.

PCT/US2018/033515 International Search Report and Written Opinion dated Oct. 22, 2018.

PCT/US2018/063498 International Preliminary Report on Patentability dated Jun. 11, 2020.

Rose Intron-mediated regulation of gene expression. Curr Top Microbiol Immunol., 326:277-290 (2008).

Sakharkar et al.: Distributions of exons and introns in the human genome. In Silico Biol. 4(4):387-393 (2004).

Samadder et al.: Transcriptional and post-transcriptional enhancement of gene expression by the 5' UTR intron of rice rubi3 gene in transgenic rice cells. Mol Genet Genomics. 279(4):429-439 doi:10.1007/s00438-008-0323-8 (2008).

SEQ ID 1 and 2 sequence alignment (2023).

Sequence alignment for exemplar sequences SEQ ID No. 1, 2, 13 and 22 (2023).

Shaul: How introns enhance gene expression. Int J Biochem Cell Biol. 91(Pt B):145-155 doi:10.1016/j.biocel.2017.06.016 (2017).

Snyder, Richard O, and Philippe Moullier. Adeno-Associated Virus: Methods and Protocols. Humana Press (2011).

Tanenhaus, Annie. et al. Cell-selective adeno-associated virus-mediated SCN1A gene regulation therapy rescues mortality and seizure phenotypes in a Dravet syndrome mouse model and is well tolerated in nonhuman primates. Human gene therapy 33(11-12):579-597 (2022).

U.S. Appl. No. 16/687,426 Notice of Allowance dated Jun. 12, 2024.

U.S. Appl. No. 16/687,426 Office Action dated Jul. 6, 2022.

U.S. Appl. No. 16/687,426 Office Action dated Mar. 27, 2023.

U.S. Appl. No. 16/687,426 Office Action dated Nov. 22, 2022.

U.S. Appl. No. 16/687,426 Office Action dated Nov. 3, 2023.

U.S. Appl. No. 16/886,129 Notice of Allowance dated Feb. 27, 2024.

U.S. Appl. No. 16/886,129 Notice of Allowance dated May 2, 2024.

U.S. Appl. No. 17/523,627 Notice of Allowance dated Jun. 13, 2025.

U.S. Appl. No. 17/523,627 Office Action dated Apr. 17, 2025.

Willyard: New human gene tally reignites debate. Nature. 558(7710):354-355 doi:10.1038/d41586-018-05462-w (2018).

Wu et al., Optimization of Self-complementary AAV Vectors for Liver-directed Expression Results in Sustained Correction of Hemophilia B at Low Vector Dose, Molecular Therapy, 16(2): 280-289 (2008).

Yan et al. Optimization of Recombinant Adeno-Associated Virus-Mediated Expression for Large Transgenes, Using a Synthetic Promoter and Tandem Array Enhancers. Human Gene Therapy 26:334-346 (Jun. 2015). DOI: 10.1089/hum.2015.001.

Zetsche, Bernd. et al. Cpf1 is a single RNA-guided endonuclease of a class 2 CRISPR-Cas system. Cell 163(3):759-771 (2015).

Zhang, Weifeng, et al., Rescue the Failed Half-ZFN by a Sensitive Mammalian Cell-Based Luciferase Reporter System. Plos One 7(9):1-9 (2012).

* cited by examiner

SEQUENCE LISTING

```
Sequence total quantity: 43
SEQ ID NO: 1              moltype = DNA  length = 681
FEATURE                   Location/Qualifiers
source                    1..681
                          mol_type = genomic DNA
                          organism = Homo sapiens
SEQUENCE: 1
ggaggaagcc atcaactaaa ctacaatgac tgtaagatac aaaattggga atggtaacat  60
attttgaagt tctgttgaca taaagaatca tgatattaat gcccatggaa atgaaagggc  120
gatcaacact atggtttgaa aaggggaaa ttgtagagca cagatgtgtt cgtgtggcag  180
tgtgctgtct ctagcaatac tcagagaaga gagagaacaa tgaaattctg attggcccca  240
gtgtgagccc agatgaggtt cagctgccaa ctttctcttt cacatcttat gaaagtcatt  300
taagcacaac taactttttt tttttttttt ttttttttgag acagagtctt gctctgttgc  360
ccaggacaga gtgcagtagt gactcaatct cggctcactg cagcctccac ctcctaggct  420
caaacggtcc tcctgcatca gcctcccaag tagctggaat tacaggagtg gcccaccatg  480
cccagctaat ttttgtattt ttaatagata cgggggtttc accatatcac ccaggctggt  540
ctcgaactcc tggcctcaag tgatccacct gcctcggcct cccaaagtgc tgggattata  600
ggcgtcagcc actatgccca acccgaccaa ccttttttaa aataaatatt taaaaaattg  660
gtatttcaca tatatactag t                                            681

SEQ ID NO: 2              moltype = DNA  length = 502
FEATURE                   Location/Qualifiers
source                    1..502
                          mol_type = genomic DNA
                          organism = unidentified
SEQUENCE: 2
agtttggaca agaactatag ttctagcttt ctctgggtct ccaccttgca gagaatgcag  60
ctttcattat ctcatgagcc aaactctcat catctctttc catatatctg tcggtgctct  120
tccatgagta ctctaacaca cacagaagga gcacttacac aggctgttgt ttttctctta  180
ttatcatagc tgttgttcag acatgtgcat tctgttcttg ttgcttcaat gctaaaggag  240
tctcaggata tgagaactgt accagccgag gcatcaggaa acatgggtgg aaattcccac  300
agtactattt gttcactgtg tgaccttggg ccagtcacat ccctttcctg aggcttcgat  360
tccccaagct ataaaagaag catctcttaa ccttttttta ggtcatgagt caggcccagc  420
acactctcag ggagactcat gagagtacag atcatttccc atagaaaaac catagtttta  480
tatccagagg cttttctgta ag                                           502

SEQ ID NO: 3              moltype = DNA  length = 823
FEATURE                   Location/Qualifiers
source                    1..823
                          mol_type = genomic DNA
                          organism = unidentified
SEQUENCE: 3
ggttccagtt cagaggcaga gcatttgggg ttcccagtca ggagctttcc tctctccgct  60
```

-continued

```
ccttagtttc ctctctttaa aaaaaaatgg gtgatagtat agaaaggaag ctctgggctc    120
ggggaccagg gccctgggat ccccgctccc agccactcgc tcctgaccct tccagggaca    180
agctccccc caccccgtcc tttccaggct gccactagaa gagatgggga cgcgtggtca    240
gccgcttctg tcgccccca gggaacggtc tcacgctgga gggggcagtg ccctcggaac    300
aggacagtca gcccaagcca gccaagcgcg cgcggacgtc cttcaccgca gagcaattgc    360
aggtaccccg ggcaagcccc gaagcgtgtg ggcggggctt cggagtgggc gtggttgttc    420
gggacttgtg actccgcccc ttgtgcgggg acccgcgtga ggccgctcca aggatgaagc    480
tgcctggggc gtggcctcgg accctgagcc tctgattggg cggaggtctc agggcccttc    540
tgcgccccac aggttatgca ggcgcagttc gcgcaggaca acaacccgga cgcgcagacg    600
ctgcagaagc tggcggacat gacgggcctc agtcgcaggg tcatccaggt ggggctccgg    660
ggtctcggcc ttcaggtcta gggtgaacct tagggaagcg ctgaagctcg tagtggtacg    720
gatggtcgcg cgtgcacgtg gccgccctc tccagtgtgg cctaaggacc ccagtcggca    780
cggggttgacc cttttccttg attactgaga gtgcagaggc tgt    823
```

SEQ ID NO: 4                moltype = DNA   length = 633
FEATURE                    Location/Qualifiers
source                     1..633
                           mol_type = genomic DNA
                           organism = unidentified
SEQUENCE: 4

```
tggtgggaag acatgtccag ggaagaaatg gcctccagag gcctgaggtg gggaaatgct    60
ggaggtggag agaggaacaa ctgactgaaa atgagcttcc actgtggctt agtagcctat    120
accaagtcta gagtataggg taggagaaga ttaggaaagc gatgggtctg agaatgatgt    180
ggcctgttga cttttgtaaa cccaaagcac cttggactaa accctatgaa cagtgtggtg    240
ccaccaaaga ctataatgag ctcagggaac agaattctgt gtgcatggtg attttttttt    300
ttttttctg ctaactgcag tctgggtgat gcattgacaa accaatcctg gaaagtaaga    360
ggcaagggca gctgggacgg tgagaggagc ctgatgggaa ccaggccaag cagggcagca    420
gaggcgatga agaggatgtg gtgcatccag agactcactt cattagctgg aggcactgct    480
ggatagggtc tgaaggttct ggtatctgag ttggcgggct gggtgagtgg tggctctgct    540
tcctgaacag tgtgtgcaag aggaaacagg gttaagggct aggacagtca caggtgagtc    600
agcctcacaa gagcaacctt cccctagtgc aga    633
```

SEQ ID NO: 5                moltype = DNA   length = 670
FEATURE                    Location/Qualifiers
source                     1..670
                           mol_type = genomic DNA
                           organism = unidentified
SEQUENCE: 5

```
ggaggtctcc ttttgccccg gttccaacaa gagaatgcaa ggctgtatct caatttcctt    60
gagcctctct gtattataga agaaaagtag ggaagccata cgcccttct gagcttcagt    120
gtctctctgt ctctgcaaat gaggctgggg aggctggggg cgggcgtgaa agaggcccgc    180
gccaagccga cccccacctc tgcccctcc ccaggtcaac aacctcatct ggcacgtgcg    240
gtgcctcgag tgctccgtgt gtcgcacatc gctgaggcag cagaatagct gctacatcaa    300
gaacaaggag atctactgca agatggacta cttcaggtag gcagcggcca tcccgccagc    360
aagcgctgga gcatgaacgc cttgcacacg cgtgcctagg ccacttgtgt ggcctgtgct    420
ctccaattcc tgagccctgc tgttcagagt gcacaacgcg gctcagcgca ctggcccggc    480
cctcctactc agcacgtctt acacagaagg gagcgccagt ctcagcctga gttctggcgg    540
gggatctgcc tcgggttcct ccgatctgac aggcgctggc cacgggtctg gttccatctc    600
tggtcttttc tggccccgag caccagtgtg ttctgttgag ctctgatgtc cgaggctctg    660
gcccggatca    670
```

SEQ ID NO: 6                moltype = DNA   length = 1043
FEATURE                    Location/Qualifiers
source                     1..1043
                           mol_type = genomic DNA
                           organism = unidentified
SEQUENCE: 6

```
ctctggctac ctcttatctt gggcattcac gacaatttct aattgcaggt agtttgtgtg    60
tgtgcgcgtg ttttttttcc ccctcagagg cttggattgc aaaggaacta agcgattact    120
tcaagagcca cgggttaagt gcagggagag ggggagagag agggaaaaaa acccaatcca    180
aattcaaatt gcttcattag agagacaccg cttttgtggg gaagggcttt aaatgcccac    240
tacaaagtta ggactcattg ttcagcgccg gtttatataa caggcgaggg gaggcgctgg    300
gctctgcacag ctccgagcca gttcagcagc cgccgtcgcc tgcattccct cccccctccc    360
caggtgatgg cccagccagg gtccggctgc aaagcgacca cccgctgtct cgaagggacc    420
gctccgcctg ccatggtgag tccttcggt cctgctttcg gccccgagtc cccccaacag    480
cacaggccag ggcttctggc tcagccttcc ggctaccaac ctctaccct gcgctggaaa    540
actgccgata ggagccgcct ctcgttgagc cttggttttt ctggcctgga atgtgagctt    600
tggctgcttc ctgcacccag gatgcgctgt gttaaaagtt gggggccgtc ccttcttctc    660
caataggtcc tttcattctt gtactccagc ctagggcgcg acatccctgg cacatttcgg    720
tgtcagtcgg tgcgcgagga aaccagattc aactctgagt actcggctaa gcgcttcgct    780
gttcctctct cccatttcag gctcagtcag acgcagaggc cttggcaggc gctctggaca    840
aggacgaagg tagagcctcc ccatgtacgc ccagcacacc gtctgtctgc tcgccgccct    900
ctgctgcctc ttccgtgccg tctgccggca agaatatctg ctccagttgc ggtctggaga    960
tcctggaccg gtatctgctc aaggtgagtc agggtaggtg tgcctgcttg cccacgggtg    1020
tggtttgcag ccccaagagc tgt    1043
```

SEQ ID NO: 7                moltype = DNA   length = 507
FEATURE                    Location/Qualifiers
source                     1..507

```
                         mol_type = genomic DNA
                         organism = unidentified
SEQUENCE: 7
caagactttt aaaagtttag ataaataaac aaacatttga cggctttcca tcacatctag    60
actataatcc aaagatctat atggtcccaa acgacttaca cttaactacc gtctcccata   120
tggcttcttc ccccatcagt cattgtcctc agccatagtg gcctccctgt tcctttgggt   180
acaagggaac aactccctga gaggttccat tagctgctgt tgcctgagat gctcttgagc   240
ccacaccatc tgctcatttc tctcctcacg tgtcagtgat taagaggctg tccttggcct   300
cccgtcaaaa ttacatccct gccgctttcc acttcttgcc ttcttatttt ctaaatagaa   360
ctaactcacc actacccaac attctatata attggatatc tgtcctctgt ttaaatataa   420
tgttgacttc aagaaagaac gttgtcactg ccctgtcacc agacttttaa acagtgccta   480
tcgtgtggca catgctcagt gaaattg                                        507

SEQ ID NO: 8          moltype = DNA   length = 502
FEATURE               Location/Qualifiers
source                1..502
                      mol_type = genomic DNA
                      organism = unidentified
SEQUENCE: 8
tcaacagggg gacacttggg aaagaaggat ggggacagag ccgagaggac tgttacacat    60
tagagaaaca tcagtgactg tgccagcttt ggggtagact gcacaaaagc cctgaggcag   120
cacaggcagg atccagtctg ctggtcccag gaagctaacc gtctcagaca gagcacaaag   180
caccgagaca tgtgccacaa ggcttgtgta gagaggtcag aggacagcgt acaggtccca   240
gagatcaaac tcaacctcac caggcttggc agcaagcctt taccaaccca cccccacccc   300
acccaccctg cacgcgcccc tctcccctcc ccatggtctc ccatggctat ctcacttggc   360
cctaaaatgt ttaaggatga cactggctgc tgagtggaaa tgagacagca gaagtcaaca   420
gtagattta  ggaaagccag agaaaaaggc ttgtgctgtt tttagaaagc caagggacaa   480
gctaagatag ggcccaagta at                                             502

SEQ ID NO: 9          moltype = DNA   length = 788
FEATURE               Location/Qualifiers
source                1..788
                      mol_type = genomic DNA
                      organism = unidentified
SEQUENCE: 9
aaatagaact gtgagatagg gggagagggg gcaggaagga caagagaccc ctgtctcatt    60
gtgatcccca cctgtctgct ctgtgggagg gtacccatga gggccagccc acagcccta    120
ggtggacatt gtctggtcct gtctcactgt ccctcccagc agcccagag gccaggagac    180
aggggtctca gtcctcactg agagatgtgt aaactgaggc ccagtgaatg ttgagggcca   240
gggcatgccc ttggtgggat gtgacctggg tctccttcgc acgggcttcc tccccgaagc   300
cgagctgagc atttggagtt tgaaatgttt ccgtacttag caatctgctc ctctattccc   360
gggcggactt ccgatagctc cggccttatg ctgcactaga taagatggag caggagagg    420
acacggcact acttatgtaa ccggcctctt gaaaaatgga gcaggcggtca gggcggaaca   480
agacgtcctc tctctacgca tccctctcct ttccctgcta aggctgcagc tggagtcaga   540
ggcagggctg ttccaatctg tctttgatca gtaacgcagc cagcctccag cctccgtcag   600
cctcctcatg gctgagaccc ggcctcagtt tcccccactt acatcccgag gatcagagcc   660
tgtgaggatg aaatgggata aggtagctgg aaccgtctgg cagagagcga gtcctcagga   720
ctgttgatgc ctgtggctgc ctggcttgac cccaagtgac cccgcctcct catcctgcag   780
caggagaa                                                             788

SEQ ID NO: 10         moltype = DNA   length = 502
FEATURE               Location/Qualifiers
source                1..502
                      mol_type = genomic DNA
                      organism = unidentified
SEQUENCE: 10
tctatagaat gtgtccccag ccttgttttc cacacttgat acgcaaggaa tgcataccac    60
agagagggat gagggtagca tccagcctgc ttcctgtgtg tcggggcgct acagccacat   120
ctccccagtc catctcagac cgtcacagag cttcgccgaa tgtatagctt tgttctctgt   180
gcagacaggg agacagagcc ttgggaagca taggtgcttg cttctttgcc cactgagtct   240
tagctggact tgcacaccac atgcctcaca gccgggcgca cttgcatttg tcacccaggc   300
ccagtgatga tggctctgct tgctttgtgc tttgtgccaa ctacagctcc agcacctgtg   360
ccctgggttt tcactccttt agttgaacac gtagttactg gggttgtagg gatggagcct   420
ttctgcttcc ttctggcaaa gtccttagcg gcctgctgcg ggggtggggg gtgttcaggg   480
gagtggtgat gaagtatgac ag                                             502

SEQ ID NO: 11         moltype = DNA   length = 533
FEATURE               Location/Qualifiers
source                1..533
                      mol_type = genomic DNA
                      organism = unidentified
SEQUENCE: 11
tctccagttg gagaaacaga tgctgtaact ggggccacag tataaagaga gcccagacat    60
tgaactgtca acacagaagc ctggcacact ggaactggca gtccagctgg gaacaagggg   120
tagaggctga ggccactaag tcaactgagg caggagacat aggagctaaa gcagctgaag   180
ggtgcaggac agctgggggg tctgaagtgg gcctcatgcc cagagctatg aagtcagggg   240
ctgtagccta ggagccttgg aagccagctg gcaagctgtg gcccaaagac gctgactcac   300
caggaggggg cagctggagc caggcactcc taaggtttcc aggaagggca gccttccagg   360
gctcagctag gggagacagt gttgacagca agttgtcagg caacttgagc tactgggcag   420
```

-continued

```
ctgggaagct gtcccttggt ccccagtatc atcatcaccc cagacgctgc ccacctgcct   480
caggtcccac acagtgatcc tcccatcttt aacacaacac atgaccagag aga           533

SEQ ID NO: 12          moltype = DNA   length = 524
FEATURE                Location/Qualifiers
source                 1..524
                       mol_type = genomic DNA
                       organism = unidentified
SEQUENCE: 12
gtcaccctcc ccccaaacaa cccccttcttc tctggttcga gaaattacag gcatgaaaga   60
tataaatcgg gatgcttgac ttgggaatat aaatcactaa agcttggggg caggggtggg   120
cgacctttgt gaccgtcctt gtgcgtgcca gtaaatcctg tggtccaggg gagaagaaaa   180
ggctgtgtgg cttctgctca caaagctgca gaaaccattc tttaagccca aaagcacttc   240
cagagagagc agagcatccc caggctgctg gctcagcaag ttcactgtgc tcaatctcag   300
gaagtgagga taagagcagt gcctggagag tgcctggtgc tgagctgagg gtttctgaac   360
acattaaagc ggggagcatg gaccgggcct caggaggggt gttgaacatc cctaggcaga   420
ggagtctagc ttcctgggaa aagatatcag gttaagcaca cacatgtcct ctggaataag   480
ataatctttc tgatcacaca ctatacacac acaaaagcct gctc                    524

SEQ ID NO: 13          moltype = DNA   length = 509
FEATURE                Location/Qualifiers
source                 1..509
                       mol_type = genomic DNA
                       organism = unidentified
SEQUENCE: 13
gccctctagg ccacctgacc aggtcccctc agtccccccc ttcccacact cccacactca   60
gccccctcc ccccccccg acccctgcag gattatcctg tctgtgttcc tgactcagcc    120
tgggagccac ctgggcagca ggggccaagg gtgtcctaga agggacctgg agtccacgct   180
gggccaagc tgcccttct ccctctgtct tccgtccctg cttgcggttc tgctgaatgt    240
ggttatttct ctggctcctt ttacagagaa tgctgctgct aatttatgt ggagctctga    300
ggcagtgtaa ttggaagcca gacaccctgt cagcagtggg ctcccgtcct gagctgccat   360
gcttcctgct ctcctcccgt cccggctcct catttcatgc agccacctgt cccagggaga   420
gaggagtcac ccaggcccct cagtccgccc cttaaataag aaagcctccg ttgctcggca   480
cacataccaa gcagccgctg gtgcaatct                                     509

SEQ ID NO: 14          moltype = DNA   length = 398
FEATURE                Location/Qualifiers
source                 1..398
                       mol_type = genomic DNA
                       organism = unidentified
SEQUENCE: 14
gtgttcttcc cttccccttt ggacccccga gacaagccaa taaaatactc ggcagggtgg   60
cttctctcct ttttttgcca gtaataaaca gactcagagc aagttaaggg tctggtccaa   120
ggtcatggct gggatcagtg acagagccca gaagagaacc tgagacttct tgctgagcca   180
agctggagag gacagaaagg aatgcgtcta ctccatgcat gaccctctgc cagctttgct   240
ccttcctaag ggaccatgaa cgatatgtgc acaccgctca tacgtatgtg cacacctgca   300
agaggaggca tcccatgtac acctatgaga cgcacagaga aacatatatg tagccatagg   360
ctagaaattc tttctctttc taggtctgcc cctctgca                           398

SEQ ID NO: 15          moltype = DNA   length = 810
FEATURE                Location/Qualifiers
source                 1..810
                       mol_type = genomic DNA
                       organism = unidentified
SEQUENCE: 15
ggaccactca gtgtacacgg aatgtagaat tgagtctgcc attggtcttc cctcaaagtc   60
ttggaggctt gggactgata ttgggagcat ctgggcagag aaggccacaa agacagggtg   120
gttttttctac actgggacat actcgtgagc atgcacagag gcgtgtcccc aacttccctg   180
tcacccctgt cctctgccgg ctagagggga tgcgggggtg gacatatgct gctattgggc   240
agatatcaca tgttaagagg tggggggggg ctcaagaggc ggaggggctag gagcatccca   300
tggggagagg ttctggtttt cttgctgcct ctagctgcta taaatacgtt agcacttgag   360
caactggaaa gctctgagta atttaggatg cacaaagctg taatttaact ccagcatctc   420
agtgtgcgag agcattaaag atgtaattaa gatgtttaca caaagagatt ggagtctgtg   480
acacttgggg tgcaaaaccc caggaaggga cacaatgggt gaggtgagga tctgtgaggaa   540
gcctggggac agtcacttgg atcccagcta tgagatggca ggccacccag ctgtttctcc   600
ttggaaatgt tttggcctgg gggttggggg tggggcatca cactttgata tggagatggg   660
gcaacaaagc ctgcaatatc tggggtgtgga gaggtcaagt ggatggagtc ttttgagatc   720
atgtcaggaa gagggctcga tcccccaaaa tcatggtgac atatggtgtc tcggggttca   780
caggagctat gtctaaaata caaaagtaaa                                    810

SEQ ID NO: 16          moltype = DNA   length = 202
FEATURE                Location/Qualifiers
source                 1..202
                       mol_type = genomic DNA
                       organism = unidentified
SEQUENCE: 16
tctgcagaag cctgccattc caccatttaa acctgtgact ccaggcctta agcctgttga   60
aggtcgagtc ccagaagggt catatgtgca actgcctagg gagagttccc actcgcaggg   120
ccaagaggag tccccggtc tgaggtgtgg gggcggggac gtgcactggg cgctgggacc    180
```

```
acggctgggg ctcaggactc gc                                             202

SEQ ID NO: 17          moltype = DNA   length = 937
FEATURE                Location/Qualifiers
source                 1..937
                       mol_type = genomic DNA
                       organism = unidentified
SEQUENCE: 17
tgcctcagtt tcttcgccta gaaagccggg tctaagggta catgccctga ttcttttctg   60
gggtgtctcg aattttaaac aacacatact gttctgggct gatgacaaga ggaagtactg   120
gtcggtggct gatggacatc caccatggtg gcaactggag ggaggggggaa cggacgttga   180
aaccctgccc tcctggaatc tgtcgcatgc acgcacgttg acaatgcttg gcactgggga   240
caggctggga tggatggagc ggagcgtgag gaggagtggg catgcaggcc cgagtgtctg   300
ttttgctgat tgctcctttt gctttcaagg agattaaact atttttagtc catgcctact   360
gctggtgaga cgctggagga agcctttcca tcgttgagat tttctggaag ctgccaagtg   420
tggtcttcag ctcaattctg ggagcctccc agagtgggag ggaggaacat ttccatctgg   480
gggcttcggg gacaggctaa gatcttccct ggggtccttg ctgcgctggc ctcctcaaac   540
cacgctgcct cggcctgcat aaagcagtaa tctgatgtgc ccgatgtttg taacgctgga   600
tttaaaaaaa gtaatttatt ttctaattat tccttgtctt gcataaccat gcattgccaa   660
agtgtcgcta tttaaaatat ttatctctcc acgccgcagg agcagctctg gagcgtggag   720
ggggaagaaa taaaagtccg cgtgccagtc gcaggcatat tactttgact cgtcctggtg   780
gctttgacgt ctccctgtaa atacatttat ttttcattag gacgttttctg agcttgtggc   840
ccccggagag cggagtgatt acgctgttca tctgcaagcg atgcaataga ggggtactcg   900
cagaatgact tccgcccaga gcatcctgcg cctgtct                             937

SEQ ID NO: 18          moltype = DNA   length = 922
FEATURE                Location/Qualifiers
source                 1..922
                       mol_type = genomic DNA
                       organism = unidentified
SEQUENCE: 18
taaaatacct tatttttttc cagtctctaa actgctaatc tcccaggcta agggattctg   60
ggacaaaggc aaggcctgga agtggaaatc tgtaaaatta gcttcagcgg tattagtgtt   120
tgcagttgaa gattgaaaaa ctgctttccc agggcctgat tggaggctcc actctcctcc   180
aggaagaggc aaggactctg ggctggcact gaggacaaat cctgggaggc tgctatgggg   240
cctgggagcc aggctgcctt gtgctagagg cctagagagt gtctgtgtcc caagtcccaa   300
gctaccccca gcagctaaca gcttttccag ttctcaggca cagcaggtgc caagatcacg   360
ctctggagtc cagctgggcc ccttcctctt cttttttttt tttttttttt aagacctcct   420
ggacactgtt cctctccccc ccccccgtgac ccccccccctc agttctcaaa cacgtgaggg   480
ttgggggagg gttccacagc cagagagagg ggccagctct ggtgcctgtg ggtacgcccg   540
cccgtatggc ccatcaggcc tcttgtgtgc ttgattgcct ctgattggct gcagctgaat   600
tcagcaaaag ctattatttg cccttgatga gccaatcaga tggcctcatt ggccattcag   660
agcaggcacc ggaacctgag ggtggggtgg ggggtgggg atggagatgg gactcagtga   720
ggggggtggga agctctaaaa cagatgcagg acctgagcct gtctgtgtcc accacgacct   780
tcacacaggt cacaccccct tcccctgact tgtcacccca aaccagggct tgttgcccaa   840
ccccacctca caattccctc actctgtaac acctttccat atacctctgc atgtctaaac   900
ccaagacttg ctctatgaaa tc                                            922

SEQ ID NO: 19          moltype = DNA   length = 639
FEATURE                Location/Qualifiers
source                 1..639
                       mol_type = genomic DNA
                       organism = unidentified
SEQUENCE: 19
agaccctgct tagcacagct cttagcgggt cctttagggg gtctcccagc gggcccagtg   60
ggaatgagat aaggaaggac acagctgtcc attctcccgt gcctgctaag gaggaaatgg   120
ggccgcctta cataattggg gcaatttgtt ccactcttgt cctcctggta tcatggctat   180
caccccctcc ttgctcaggg agtccttgat tgagcgagaa gctcaggcct ccctctctcc   240
ctcctgctgg gggttgctga acagagggtg taggagccat aggctctgtc actgctgaga   300
tctgccagat gtctaggcca ggagaaaatg gaaagggcta agtcacagca tatgtggcca   360
ctcaggccta tagccccaaa tctgcctggt aacccattat gtcccagag aatttgcatg    420
ggcggacacc ctcatgccgg gtctcagtaa gggaagggggt gggaggcaaa aatatccctc    480
cccaccctga atctccaccc cctcccccca gaaactgaca cttggccttg tctaaggatg    540
ggttttccca aaatccttct gaaaaaaaca gaatttcaag agtcactccc tccgggtctc    600
agcctagaac atatgcagta tccctgacg tccataggg                            639

SEQ ID NO: 20          moltype = DNA   length = 716
FEATURE                Location/Qualifiers
source                 1..716
                       mol_type = genomic DNA
                       organism = unidentified
SEQUENCE: 20
aaactggcac agtaatggcg ggctgacaga caagggagtc tgtagcaccc gctgcctccg   60
cccacccctt ctccgagcaa ttaaaaggtg tttatgtggg gctggcagtg gcttctgcct   120
cccttccatt acgaacatta agagatcttg acccttccac tttcccgct cttgaaagga    180
gctgcagaca cgtggagcca attaggcgca cgcgtgggcg ccaagggcct gagcagcttt   240
ttctccctga ttgcggcgtt tacagctgat tattctcccc tcaccaaac agtgctgctt    300
cctgcaagg tgccacccag aggagccggc tggggggcccc tggggacagg ggaggactgg    360
attagtaaat gggcatctat cgaatggctt tcatatgtgt ggctggaagg gagaagggta   420
```

-continued

```
gggccaggaa tggtggcagc aagggcccag gtagcaatga gggttcttct aacccaccat    480
ttagggatag cgatcagaaa agggccctcg aggaggtgac ctaaatgtgt gtagaagctg    540
acggccacta cacacacaca cacacacaca cacacacata cacaagcatc cttgtccttg    600
gagtcggtca gcatgagcaa gagaaagatg ttcccagtgg ccatgagagt ggagccctcc    660
tccctactta catccaggtt ggatggccag gagatcctga gatccttcaa gactcc        716

SEQ ID NO: 21           moltype = DNA   length = 147
FEATURE                 Location/Qualifiers
source                  1..147
                        mol_type = genomic DNA
                        organism = unidentified
SEQUENCE: 21
aagccacatc ctgggtggaa atatatggct tcaattccca ctcttccgga tgacctctgt    60
ggggagccct ggcttcacct tggtccagct tcatcccta gcctcgctgc caggaaggca     120
gtgaggtcag aggctggtgc tggcgtg                                        147

SEQ ID NO: 22           moltype = DNA   length = 297
FEATURE                 Location/Qualifiers
source                  1..297
                        mol_type = genomic DNA
                        organism = unidentified
SEQUENCE: 22
cctacctggt gcccgccaac atctgggggc catcctggcc agcgccagcg tggtggtgaa    60
ggcactgtgc gccgtggtac tgtttctcta cctgctttcc ttcgctgtgg acacgggctg    120
cctgccgtc accccaggct accttttccc acccaacttc tggatctgga ccctggccac      180
ccacgggctc atggaacagc acgtgtggga cgtggccatt agcctggcca cagtggttgt    240
ggccgggcga ttactggagc ccctctgggg agccttggag ctgctcatct tcttctc       297

SEQ ID NO: 23           moltype = DNA   length = 101
FEATURE                 Location/Qualifiers
source                  1..101
                        mol_type = genomic DNA
                        organism = Homo sapiens
SEQUENCE: 23
aaacggacgg gcctccgctg aaccagtgag gccccagacg tgcgcataaa taacccctgc    60
gtgctgcacc acctggggag aggggagga ccacggtaaa t                         101

SEQ ID NO: 24           moltype = DNA   length = 101
FEATURE                 Location/Qualifiers
source                  1..101
                        mol_type = genomic DNA
                        organism = Homo sapiens
SEQUENCE: 24
ggagcgagcg catagcaaaa gggacgcggg gtccttttct ctgccggtgg cactgggtag    60
ctgtggccag gtgtggtact ttgatggggc ccagggctgg a                        101

SEQ ID NO: 25           moltype = DNA   length = 101
FEATURE                 Location/Qualifiers
source                  1..101
                        mol_type = genomic DNA
                        organism = Homo sapiens
SEQUENCE: 25
gctcaaggaa gcgtcgcagg gtcacagatc tgggggaacc ccggggaaaa gcactgaggc    60
aaaaccgccg ctcgtctcct acaatatatg ggagggggag g                        101

SEQ ID NO: 26           moltype = DNA   length = 547
FEATURE                 Location/Qualifiers
source                  1..547
                        mol_type = genomic DNA
                        organism = Homo sapiens
SEQUENCE: 26
ttgagtacgt tctggattac tcataagacc tttttttttt ccttccgggc gcaaaaccgt    60
gagctggatt tataatcgcc ctaaaagct ccagaggcgg tcaggcacct gcagaggagc      120
cccgccgctc cgccgactag ctgccccgc gagcaaccgc ctcgtgattt ccccgccgat     180
ccggtccccg cctccccact ctgcccccgc ctaccccgga gccgtgcagc cgcctctccg    240
aatctctctc ttctcctggc gctcgcgtgc gagaggggaac tagcgagaac gaggaagcag   300
ctggaggtga cgccgggcag attacgcctg tcagggccga gccgagcgga tcgctgggcg    360
ctgtgcagag gaaaggcggg agtgcccggc tcgctgtcgc agagccgagg tgggtaagct    420
agcgaccacc tggacttccc agcgcccaac cgtggctttt cagccaggtc ctctcctccc    480
gcggcttctc aaccaacccc atcccagcgc cggccaccca acctccgaa atgagtgctt     540
cctgccc                                                             547

SEQ ID NO: 27           moltype = DNA   length = 101
FEATURE                 Location/Qualifiers
source                  1..101
                        mol_type = genomic DNA
                        organism = Homo sapiens
SEQUENCE: 27
cagcagccga aggcgctact aggaacggta acctgttact tttccagggg ccgtagtcga    60
```

-continued

```
cccgctgccc gagttgctgt gcgactgcgc gcgcggggct a                101

SEQ ID NO: 28          moltype = DNA   length = 201
FEATURE                Location/Qualifiers
source                 1..201
                       mol_type = genomic DNA
                       organism = Homo sapiens
SEQUENCE: 28
gagtgcaagg tgactgtggt tcttctctgg ccaagtccga gggagaacgt aaagatatgg   60
gccttttttcc ccctctcacc ttgtctcacc aaagtcccta gtccccggag cagttagcct  120
ctttctttcc agggaattag ccagacacaa caacgggaac cagacaccga accagacatg  180
cccgccccgt gcgccctccc c                                            201

SEQ ID NO: 29          moltype = DNA   length = 199
FEATURE                Location/Qualifiers
source                 1..199
                       mol_type = genomic DNA
                       organism = Homo sapiens
SEQUENCE: 29
gctcgctgcc tttcctccct cttgtctctc cagagccgga tcttcaaggg gagcctccgt   60
gcccccggct gctcagtccc tccggtgtgc aggaccccgg aagtcctccc cgcacagctc  120
tcgcttctct ttgcagcctg tttctgcgcc ggaccagtcg aggactctgg acagtagagg  180
ccccgggacg accgagctg                                              199

SEQ ID NO: 30          moltype = DNA   length = 1351
FEATURE                Location/Qualifiers
source                 1..1351
                       mol_type = genomic DNA
                       organism = Homo sapiens
SEQUENCE: 30
aaacggacgg gcctccgctg aaccagtgag gccccagacg tgcgcataaa taaccccctgc   60
gtgctgcacc acctggggag aggggggagga ccacggtaaa tggagcgagc gcatagcaaa  120
agggacgcgg ggtcctttttc tctgccggtg gcactgggta gctgtggcca ggtgtggtac  180
tttgatgggg cccagggctg gagctcaagg aagcgtcgca gggtcacaga tctggggggaa  240
ccccgggggaa aagcactgag gcaaaaccgc cgctcgtctc ctacaatata tgggaggggg  300
aggttgagta cgttctggat tactcataag accttttttt tttccttccg ggcgcaaaac  360
cgtgagctgg atttataatc gccctataaa gctccagagg cggtcaggca cctgcagagg  420
agccccgccg ctccgccgac tagctgcccc cgcgagcaac ggcctcgtga tttccccgcc  480
gatccggtcc ccgcctcccc actctgcccc cgcctaccc ggagccgtgc agccgcctct  540
ccgaatctct ctcttctcct ggcgctcgcg tgcgagaggg aactagcgag aacgaggaag  600
cagctggagg tgacgccggg cagattacgc ctgtcagggc cgagccgagc ggatcgctgg  660
gcgctgtgca gaggaaaggc gggagtgccc ggctcgctgt cgcagagccg aggtgggtaa  720
gctagcgacc acctggactt cccagcgccc aaccgtggct tttcagccag gtcctctcct  780
cccgcggctt ctcaaccaac cccatcccag cgccggccac ccaacctccc gaaatgagtg  840
cttcctgccc cagcagccga aggcgctact aggaacggta acctgttact tttccagggg  900
ccgtagtcga cccgctgccc gagttgctgt gcgactgcgc gcgcggggct agagtgcaag  960
gtgactgtgg ttcttctctg gccaagtccg aggggagaacg taaagatatg ggccttttttc 1020
ccctctcac cttgtctcac caaagtccct agtccccgga gcagttagcc tcttttctttc 1080
cagggaatta gccagacaca acaacgggaa ccagacaccg aaccagacat gcccgccccg 1140
tgcgccctcc ccgctcgctg cctttcctcc ctcttgtctc tccagagccg gatcttcaag 1200
gggagcctcc gtgccccggg ctgctcagtc cctccggtgt gcaggacccc ggaagtcctc 1260
cccgcacagc tctcgcttct ctttgcagcc tgtttctgcg ccggaccagt cgaggactct 1320
ggacagtaga ggccccggga cgaccgagct g                                1351

SEQ ID NO: 31          moltype = DNA   length = 2051
FEATURE                Location/Qualifiers
source                 1..2051
                       mol_type = genomic DNA
                       organism = Homo sapiens
SEQUENCE: 31
ggaggaagcc atcaactaaa ctacaatgac tgtaagatac aaaattggga atggtaacat   60
attttgaagt tctgttgaca taaagaatca tgatattaat gcccatggaa atgaaagggc  120
gatcaacact atggtttgaa aaggggggaaa ttgtagagca cagatgtgtt cgtgtggcag  180
tgtgctgtct ctagcaatac tcagagaaga gagagaaca tgaaattcgt attggcccca  240
gtgtgagccc agatgaggtt cagctgccaa cttttctcttt cacatcttat gaaagtcatt  300
taagcacaac taactttttt tttttttttt tttttttgag acagagtctt gctctgttgc  360
ccaggacaga gtgcagtagt gactcaatct cggctcactg cagcctccac ctcctaggct  420
caaacggtcc tcctgcatca gcctcccaag tagctggaat tacaggagtg gcccaccatg  480
cccagctaat ttttgtattt ttaatagata cggggggttttc accatatcac ccaggctggt  540
ctcgaactcc tggcctcaag tgatccacct gcctcggcct cccaaagtgc tgggattata  600
ggcgtcagcc actatgccca acccgaccaa ccttttttttaa aataaatatt taaaaaattg  660
gtatttcaca tatatactag tatttacatt tatccacaca aaacggacgg gcctccgctg  720
aaccagtgag gccccagacg tgcgcataaa taaccccctgc gtgctgcacc acctggggag  780
agggggggagga ccacggtaaa tggagcgagc gcatagcaaa agggacgcgg ggtcctttttc  840
tctgccggtg gcactgggta gctgtggcca ggtgtggtac tttgatgggg cccagggctg  900
gagctcaagg aagcgtcgca gggtcacaga tctggggggaa ccccgggggaa aagcactgag  960
gcaaaaccgc cgctcgtctc ctacaatata tgggaggggg aggttgagta cgttctggat 1020
tactcataag accttttttt tttccttccg ggcgcaaaac cgtgagctgg atttataatc 1080
gccctataaa gctccagagg cggtcaggca cctgcagagg agccccgccg ctccgccgac 1140
```

```
tagctgcccc cgcgagcaac ggcctcgtga tttccccgcc gatccggtcc ccgcctcccc    1200
actctgcccc cgcctacccc ggagccgtgc agccgcctct ccgaatctct ctcttctcct    1260
ggcgctcgcg tgcgagaggg aactagcgag aacgaggaag cagctggagg tgacgccggg    1320
cagattacgc ctgtcagggc cgagccgagc ggatcgctgg gcgctgtgca gaggaaaggc    1380
gggagtgccc ggctcgctgt cgcagagccg aggtgggtaa gctagcgacc acctggactt    1440
cccagcgccc aaccgtgggt tttcagccag gtcctctcct cccgcggctt ctcaaccaac    1500
cccatcccag cgccggccac ccaacctccc gaaatgagtg cttcctgccc cagcagccga    1560
aggcgctact aggaacggta acctgttact tttccagggg ccgtagtcga cccgctgccc    1620
gagttgctgt gcgactgcgc gcgcggggct agagtgcaag gtgactgtgg ttcttctctg    1680
gccaagtccg agggagaacg taaagatatg ggccttttc ccctctcac cttgtctcac     1740
caaagtccct agtccccgga gcagttagcc tctttcttc cagggaatta gccagacaca     1800
acaacgggaa ccagacaccg aaccagacat gcccgccccg tgcgcctcc ccgctcgctg      1860
cctttcctcc ctcttgtctc tccagagccg gatcttcaag gggagcctcc gtgccccgg      1920
ctgctcagtc cctccggtgt gcaggacccc ggaagtcctc cccgcacagc tctcgcttct     1980
ctttgcagcc tgtttctgcg ccggaccagt cgaggactct ggacagtaga ggccccggga     2040
cgaccgagct g                                                         2051
```

SEQ ID NO: 32            moltype = DNA  length = 1878
FEATURE                  Location/Qualifiers
source                   1..1878
                         mol_type = genomic DNA
                         organism = unidentified
SEQUENCE: 32

```
tcaacagggg gacacttggg aaagaaggat ggggacagag ccgagaggac tgttacacat     60
tagagaaaca tcagtgactg tgccagcttt ggggtagact gcacaaaagc cctgaggcag     120
cacaggcagg atccagtctg ctggtcccag gaagctaacc gtctcagaca gagcacaaag     180
caccggagac tgtgccacaa ggcttgtgta gagaggtcag aggacagcgt acaggtccca     240
gagatcaaac tcaacctcac caggcttggc agcaagcctt taccaaccca cccccacccc     300
acccaccctg cacgcgcccc tctcccctcc ccatggtctc ccatggctat ctcacttggc     360
cctaaaatgt ttaaggatga cactggctgc tgagtggaaa tgagacagca gaagtcaaca     420
gtagattta ggaaagccag agaaaaaggc ttgtgctgtt tttagaaagc caagggacaa      480
gctaagatag ggcccaagta atgctagtat ttacatttat ccacacaaaa cggacgggcc     540
tccgctgaac cagtgaggcc ccagacgtgc gcataaataa cccctgcgtg ctgcaccacc     600
tggggagagg gggaggacca cggtaaatgg agcgagcgca tagcaaaagg gacgcggggt     660
cctttctct gccggttggca ctgggtagct gtggccaggt gtggtacttt gatggggccc      720
agggctggag ctcaaggaag cgtcgcaggg tcacagatct gggggaaccc cggggaaaag     780
cactgaggca aaaccgccgc tcgtctccta caatatatgg gaggggggagg ttgagtacgt     840
tctggattac tcataagacc ttttttttt ccttccgggc gcaaaaccgt gagctggatt       900
tataatcgcc ctataaagct ccagagcgg tcaggcacct gcagaggagc cccgccgctc       960
cgccgactag ctgccccgc gagcaacggc ctcgtgattt ccccgccgat ccggtccccg       1020
cctccccact ctgccccgc ctaccccgga gccgtgcagc cgcctctccg aatctctctc       1080
ttctcctggc gctcgcgtgc gagagggaac tagcgagaac gaggaagcag ctggaggtga     1140
cgccgggcag attacgcctg tcagggccga gccgagcggat cgctggcgct gtgcagag      1200
gaaaggcggg agtgcccggc tcgctgtcgc agagccgagg tgggtaagct agcgaccacc     1260
tggacttccc agcgcccaac cgtggctttt cagccaggtc ctcctcccc gcggcttctc       1320
aaccaacccc atcccagcgc cggccaccca acctcccgaa atgagtgctt cctgccccag     1380
cagccgaagg cgctactagg aacggtaacc tgttactttt ccaggggccg tagtcgaccc     1440
gctgcccgag ttgctgtgcg actgcgcgcg cggggctaga gtgcaaggtg actgtggttc     1500
ttctctggcc aagtccgagg gagaacgtaa agatatgggc cttttcccc ctctcacctt      1560
gtctcaccaa agtccctagt ccccggagca gttagcctct ttcttccag ggaattagcc      1620
agacacaaca acgggaacca gacaccgaac cagacatgcc cgccccgtgc gcctccccc      1680
ctcgctgcct ttcctcctc ttgtctctcc agaccggat cttcaagggg agcctccgtg       1740
ccccggctg ctcagtccct ccggtgtgca ggaccccgga agtcctcccc gcacagctct       1800
cgcttctctt tgcagcctgt ttctgcgccg accagtcga ggactctgga cagtagaggc       1860
cccgggacga ccgagctg                                                  1878
```

SEQ ID NO: 33            moltype = DNA  length = 19
FEATURE                  Location/Qualifiers
source                   1..19
                         mol_type = genomic DNA
                         organism = Homo sapiens
SEQUENCE: 33

```
atttacattt atccacaca                                                  19
```

SEQ ID NO: 34            moltype = DNA  length = 800
FEATURE                  Location/Qualifiers
source                   1..800
                         mol_type = genomic DNA
                         organism = unidentified
SEQUENCE: 34

```
tgccgctgga ctctcttcca aggaactagg agaaccaaga tccgtttttc tgccaagggc     60
tgcccccccc acgcccccaa cccctcacc ccgatcccca cagaaagaaa tcttgaggta      120
gctggagctt cttctgtggg tgtgacagga ctgccattct cctctgtagt ctgcagaagc     180
ctgccattcc accatttaaa cctgtgactc caggccttaa gcctgttgaa ggtcgagtcc     240
cagaagggtc atatgtgcaa ctgcctaggg agagttccca ctcgcagggc caagaggagt     300
cccccggtct gaggtgtggg ggcgggacg tgcactgggc gctgggacca cggctgggc       360
tcaggactcg cgagcttgga ttcggatcgg tttgcgcgag ccagtagggc aggtccgggg     420
gtgaacgggg acgaggggcg cgcggcacac ggcgggcgcg tgaccgcggc ggggcgcgc      480
ggaggcgggc cggccaagga gagggaggga gggaatgagg gagggagcga caggggaggg     540
```

```
cggcgccggc aggttggcgg cggccgctat ttgagcgcag gtcccgggcc aggcgctcaa   600
agcgcttgga gccagcgcgg cggggagatc gctgcgcgca gcccgcagag gcgctgcggc   660
cagtgcagcc ccggaggccc cgcgcggaga aggaggtgga gaagaggccg gctttccgcc   720
cgccgcccgc gccccccac ctccatcccg ccgccgccgt cccccctccc tccccgcggc    780
gccgcatctt gaatggaaac                                                800

SEQ ID NO: 35          moltype = DNA  length = 1335
FEATURE                Location/Qualifiers
source                 1..1335
                       mol_type = genomic DNA
                       organism = unidentified SEQUENCE: 35
gagtaattca tacaaaagga ctcgcccctg ccttggggaa tcccagggac cgtcgttaaa   60
ctcccactaa cgtagaaccc agagatcgct gcgttcccgc cccctcaccc gcccgctctc   120
gtcatcactg aggtggagaa gagcatgcgt gaggctccgg tgcccgtcag tgggcagagc   180
gcacatcgcc cacagtcccc gagaagttgg ggggaggggt cggcaattga accggtgcct   240
agagaaggtg gcgcggggta aactgggaaa gtgatgtcgt gtactggctc cgcctttttc   300
ccgagggtgg gggagaaccg tatataagtg cagtagtcgc cgtgaacgtt cttttttcgca  360
acgggtttgc cgccagaaca caggtaagtg ccgtgtgtgg ttcccgcggg cctggcctct   420
ttacgggtta tggcccttgc gtgccttgaa ttacttccac gccccctggct gcagtacgtg   480
attcttgatc ccgagcttcg ggttggaagt gggtgggaga gttcgaggcc ttgcgcttaa   540
ggagcccctt cgcctcgtgc ttgagttgag gcctggcttg gcctgctgggg ccgccgcgttg  600
cgaatctggt ggcaccttcg cgcctgtctc gctgctttcg ataagtctct agccatttaa   660
aattttttgat gacctgctgc gacgctttt ttctggcaag atagtcttgt aaatgcgggc   720
caagatctgc acactggtat ttcggtttt ggggccgcgg gcggcgacgg ggcccgtgcg    780
tcccagcgca catgttcggc gaggcggggc ctgcgagcgag aatcggacgg                840
gggtagtctc aagctggccg gcctgctctg gtgcctggcc tcgcgccgcc gtgtatcgcc   900
ccgccctggg cggcaaggct ggcccggtcg gcaccagttg cgtgagcgga aagatggccg    960
cttcccggcc ctgctgcagg gagctcaaaa tggaggacgc ggcgctcggg agagcgggcg   1020
ggtgagtcac ccacacaaag gaaaaagggcc tttccgtcct cagccgtcgc ttcatgtgac  1080
tccacggagt accgggcgcc gtccaggcac ctcgattagt tctcgagctt ttggagtacg   1140
tcgtctttag gttggggggga ggggtttat gcgatggagt ttccccacac tgagtgggtg   1200
gagactgaag ttaggccagc ttggcacttg atgtaattct ccttggaatt tgcccttttt   1260
gagtttggat cttggttcat tctcaagcct cagacagtgg ttcaaagttt ttttcttcca   1320
tttcaggtgt cgtga                                                    1335

SEQ ID NO: 36          moltype = AA  length = 222
FEATURE                Location/Qualifiers
source                 1..222
                       mol_type = protein
                       organism = unidentified SEQUENCE: 36
MVSKGEELFT GVVPILVELD GDVNGHKFSV SGEGEGDATY GKLTLKFICT TGKLPVPWPT   60
LVTTLTYGVQ CFSRYPDHMK QHDFFKSAMP EGYVQERTIF FKDDGNYKTR AEVKFEGDTL   120
VNRIELKGID FKEDGNILGH KLEYNYNSHN VYIMADKQKN GIKVNFKIRH NIEDGSVQLA   180
DHYQQNTPIG DGPVLLPDNH YLSTQSALSK DPNEKRDHMV LL                       222

SEQ ID NO: 37          moltype = AA  length = 218
FEATURE                Location/Qualifiers
source                 1..218
                       mol_type = protein
                       organism = unidentified SEQUENCE: 37
MGTLLALVVG AALVSSAWGG CVEVDSDTEA VYGMTFKILC ISCKRRSETT AETFTEWTFR   60
QKGTEEFVKI LRYENEVLQL EEDERFEGRV VWNGSRGTKD LQDLSIFITN VTYNHSGDYE   120
CHVYRLLFFD NYEHNTSVVK KIHLEVVDKA NRDMASIVSE IMMYVLIVVL TIWLVAEMVY   180
CYKKIAAATE AAAQENASEY LAITSESKEN CTGVQVAE                            218

SEQ ID NO: 38          moltype = AA  length = 215
FEATURE                Location/Qualifiers
source                 1..215
                       mol_type = protein
                       organism = unidentified SEQUENCE: 38
MHRDAWLPRP AFSLTGLSLF FSLVPPGRSM EVTVPATLNV LNGSDARLPC TFNSCYTVNH   60
KQFSLNWTYQ ECNNCSEEMF LQFRMKIINL KLERFQDRVE FSGNPSKYDV SVMLRNVQPE   120
DEGIYNCYIM NPPDRHRGHG KIHLQVLMEE PPERDSTVAV IVGASVGGFL AVVILVLMVV   180
KCVRRKKEQK LSTDDLKTEE EGKTDGEGNP DDGAK                               215

SEQ ID NO: 39          moltype = AA  length = 2009
FEATURE                Location/Qualifiers
source                 1..2009
                       mol_type = protein
                       organism = unidentified SEQUENCE: 39
MEQTVLVPPG PDSFNFFTRE SLAAIERRIA EEKAKNPKPD KKDDDENGPK PNSDLEAGKN   60
LPFIYGDIPP EMVSEPLEDL DPYYINKKTF IVLNKGKAIF RFSATSALYI LTPFNPLRKI   120
AIKILVHSLF SMLIMCTILT NCVFMTMSNP PDWTKNVEYT FTGIYTFESL IKIIARGFCL   180
EDFTFLRDPW NWLDFTVITF AYVTEFVDLG NVSALRTFRV LRALKTISVI PGLKTIVGAL   240
```

-continued

```
IQSVKKLSDV MILTVFCLSV FALIGLQLFM GNLRNKCIQW PPTNASLEEH SIEKNITVNY  300
NGTLINETVF EFDWKSYIQD SRYHYFLEGF LDALLCGNSS DAGQCPEGYM CVKAGRNPNY  360
GYTSFDTFSW AFLSLFRLMT QDFWENLYQL TLRAAGKTYM IFFVLVIFLG SFYLINLILA  420
VVAMAYEEQN QATLEEAEQK EAEFQQMIEQ LKKQQEAAQQ AATATASEHS REPSAAGRLS  480
DSSSEASKLS SKSAKERRNR RKKRKQKEQS GGEEKDEDEF QKSESEDSIR RKGFRFSIEG  540
NRLTYEKRYS SPHQSLLSIR GSLFSPRRNS RTSLFSFRGR AKDVGSENDF ADDEHSTFED  600
NESRRDSLFV PRRHGERRNS NLSQTSRSSR MLAVFPANGK MHSTVDCNGV VSLVGGPSVP  660
TSPVGQLLPE VIIDKPATDD NGTTTETEMR KRRSSSFHVS MDFLEDPSQR QRAMSIASIL  720
TNTVEELEES RQKCPPCWYK FSNIFLIWDC SPYWLKVKHV VNLVVMDPFV DLAITICIVL  780
NTLFMAMEHY PMTDHFNNVL TVGNLVFTGI FTAEMFLKII AMDPYYYFQE GWNIFDGFIV  840
TLSLVELGLA NVEGLSVLRS FRLLRVFKLA KSWPTLNMLI KIIGNSVGAL GNLTLVLAII  900
VFIFAVVGMQ LFGKSYKDCV CKIASDCQLP RWHMNDFFHS FLIVFRVLCG EWIETMWDCM  960
EVAGQAMCLT VFMMVMVIGN LVVLNLFLAL LLSSFSADNL AATDDDNEMN NLQIAVDRMH  1020
KGVAYVKRKI YEFIQQSFIR KQKILDEIKP LDDLNNKKDS CMSNHTAEIG KDLDYLKDVN  1080
GTTSGIGTGS SVEKYIIDES DYMSFINNPS LTVTVPIAVG ESDFENLNTE DFSSESDLEE  1140
SKEKLNESSS SSEGSTVDIG APVEEQPVVE PEETLEPEAC FTEGCVQRFK CCQINVEEGR  1200
GKQWWNLRRT CFRIVEHNWF ETFIVFMILL SSGALAFEDI YIDQRKTIKT MLEYADKVFT  1260
YIFILEMLLK WVAYGYQTYF TNAWCWLDFL IVDVSLVSLT ANALGYSELG AIKSLRTLRA  1320
LRPLRALSRF EGMRVVVNAL LGAIPSIMNV LLVCLIFWLI FSIMGVNLFA GKFYHCINTT  1380
TGDRFDIEDV NNHTDCLKLI ERNETARWKN VKVNFDNVGF GYLSLLQVAT FKGWMDIMYA  1440
AVDSRNVELQ PKYEESLYMY LYFVIFIIFG SFFTLNLFIG VIIDNFNQQK KKFGGQDIFM  1500
TEEQKKYYNA MKKLGSKKPQ KPIPRPGNKF QGMVFDFVTR QVFDISIMIL ICLNMVTMMV  1560
ETDDQSEYVT TILSRINLVF IVLFTGECVL KLISLRHYYF TIGWNIFDFV VVILSIVGMF  1620
LAELIEKYFV SPTLFRVIRL ARIGRILRLI KGAKGIRTLL FALMMSLPAL FNIGLLLFLV  1680
MFIYAIFGMS NFAYVKREVG IDDMFNFETF GNSMICLFQI TTSAGWDGLL APILNSKPPD  1740
CDPNKVNPGS SVKGDCGNPS VGIFFFVSYI IISFLVVVNM YIAVILENFS VATEESAEPL  1800
SEDDFEMFYE VWEKFDPDAT QFMEFEKLSQ FAAALEPPLN LPQPNKLQLI AMDLPMVSGD  1860
RIHCLDILFA FTKRVLGESG EMDALRIQME ERFMASNPSK VSYQPITTTL KRKQEEVSAV  1920
IIQRAYRRHL LKRTVKQASF TYNKNKIKGG ANLLIKEDMI IDRINENSIT EKTDLTMSTA  1980
ACPPSYDRVT KPIVEKHEQE GKDEKAKGK                                    2009

SEQ ID NO: 40             moltype = AA  length = 603
FEATURE                   Location/Qualifiers
source                    1..603
                          mol_type = protein
                          organism = unidentified
SEQUENCE: 40
MAPIGLKAVV GEKIMHDVIK KVKKKGEWKV LVVDQLSMRM LSSCCKMTDI MTEGITIVED  60
INKRREPLPS LEAVYLITPS EKSVHSLISD FKDPPTAKYR AAHVFFTDSC PDALFNELVK  120
SRAAKVIKTL TEINIAFLPY ESQVYSLDSA DSFQSFYSPH KAQMKNPILE RLAEQIATLC  180
ATLKEYPAVR YRGEYKDNAL LAQLIQDKLD AYKADDPTMG EGPDKARSQL LILDRGFDPS  240
SPVLHELTFQ AMSYDLLPIE NDVYKYETSG IGEARVKEVL LDEDDDLWIA LRHKHIAEVS  300
QEVTRSLKDF SSSKRMNTGE KTTMRDLSQM LKKMPQYQKE LSKYSTHLHL AEDCMKHYQG  360
TVDKLCRVEQ DLAMGTDAEG EKIKDPMRAI VPILLDANVS TYDKIRIILL YIFLKNGITE  420
ENLNKLIQHA QIPPEDSEII TNMAHLGVPI VTDSTLRRRS KPERKERISE QTYQLSRWTP  480
IIKDIMEDTI EDKLDTKHYP YISTRSSASF STTAVSARYG HWHKNKAPGE YRSGPRLIIF  540
ILGGVSLNEM RCAYEVTQAN GKWEVLIGST HILTPTKFLM DLRHPDFRES SRVSFEDQAP  600
TME                                                               603

SEQ ID NO: 41             moltype = AA  length = 511
FEATURE                   Location/Qualifiers
source                    1..511
                          mol_type = protein
                          organism = unidentified
SEQUENCE: 41
MGQGDESERI VINVGGTRHQ TYRSTLRTLP GTRLAWLAEP DAHSHFDYDP RADEFFFDRH  60
PGVFAHILNY YRTGKLHCPA DVCGPLYEEE LAFWGIDETD VEPCCWMTYR QHRDAEEALD  120
SFGGAPLDNS ADDADADGPG DSGDGEDELE MTKRLALSDS PDGRPGGFWR RWQPRIWALF  180
EDPYSSRYAR YVAFASLFFI LVSITTFCLE THERFNPIVN KTEIENVRNG TQVRYYREAE  240
TEAFLTYIEG VCVVWFTFEF LMRVIFCPNK VEFIKNSLNI IDFVAILPFY LEVGLSGLSS  300
KAAKDVLGFL RVVRFVRILR IFKLTRHFVG LRVLGHTLRA STNEFLLLII FLALGVLIFA  360
TMIYYAERIG AQPNDPSASE HTHFKNIPIG FWWAVVTMTT LGYGDMYPQT WSGMLVGALC  420
ALAGVLTIAM PVPVIVNNFG MYYSLAMAKQ KLPKKKKKHI PRPPQLGSPN YCKSVVNSPH  480
HSTQSDTCPL AQEEILEINR AGRKPLRGMS I                                 511

SEQ ID NO: 42             moltype = AA  length = 639
FEATURE                   Location/Qualifiers
source                    1..639
                          mol_type = protein
                          organism = unidentified
SEQUENCE: 42
MGKIESNERV ILNVGGTRHE TYRSTLKTLP GTRLALLASS EPQGDCLTAA GDKLQPLPPP  60
LSPPPRPPPL SPVPSGCFEG GAGNCSSHGG NGGNGGSDHP GGGREFFFDR HPGVFAYVLN  120
YYRTGKLHCP ADVCGPLFEE ELAFWGIDET DVEPCCWMTY RQHRDAEEAL DIFETPDLIG  180
GDPGDDEDLA AKRLGIEDAA GLGGPDGKSG RWRKLQPRMW ALFEDPYSSR AARFIAFASL  240
FFILVSITTF CLETHEAFNI VKNKTEPVIN GTSPVLQYEI ETDPALTYVE GVCVVWFTFE  300
FLVRIVFSPN KLEFIKNLLN IIDFVAILPF YLEVGLSGLS SKAAKDVLGF LRVVRFVRIL  360
RIFKLTRHFV GLRVLGHTLR ASTNEFLLLI IFLALGVLIF ATMIYYAERV GAQPNDPSAS  420
EHTQFKNIPI GFWWAVVTMT TLGYGDMYPQ TWSGMLVGAL CALAGVLTIA MPVPVIVNNF  480
```

-continued

```
GMYYSLAMAK QKLPRKRKKH IPPAPLASSP TFCKTELNMA CNSTQSDTCL GKENRLLEHN   540
RSVLSGDDST GSEPPLSPPE RLPIRRSSTR DKNRRGETCF LLTTGDYTCA SDGGIRKAST   600
LEPMESTAQT KGDTRPEAHW NCAHLLNFGC PTGSSFPTL                          639

SEQ ID NO: 43              moltype = AA  length = 757
FEATURE                    Location/Qualifiers
source                     1..757
                           mol_type = protein
                           organism = unidentified
SEQUENCE: 43
MLSSVCVSSF RGRQGASKQQ PAPPPQPPES PPPPPLPPQQ QQPAQPGPAA SPAGPPAPRG    60
PGDRRAEPCP GLPAAAMGRH GGGGGDSGKI VINVGGVRHE TYRSTLRTLP GTRLAGLTEP   120
EAAARFDYDP GADEFFFDRH PGVFAYVLNY YRTGKLHCPA DVCGPLFEEE LGFWGIDETD   180
VEACCWMTYR QHRDAEEALD SFEAPDPAGA ANAANAAGAH DGGLDDEAGA GGGGLDGAGG   240
ELKRLCFQDA GGGAGGPPGG AGGAGGTWWR RWQPRVWALF EDPYSSRAAR YVAFASLFFI   300
LISITTFCLE THEGFIHISN KTVTQASPIP GAPPENITNV EVETEPFLTY VEGVCVVWFT   360
FEFLMRITFC PDKVEFLKSS LNIIDCVAIL PFYLEVGLSG LSSKAAKDVL GFLRVVRFVR   420
ILRIFKLTRH FVGLRVLGHT LRASTNEFLL LIIFLALGVL IFATMIYYAE RIGADPDDIL   480
GSNHTYFKNI PIGFWWAVVT MTTLGYGDMY PKTWSGMLVG ALCALAGVLT IAMPVPVIVN   540
NFGMYYSLAM AKQKLPKKKN KHIPRPPQPG SPNYCKPDPP PPPPPHPHHG SGGISPPPPI   600
TPPSMGVTVA GAYPAGPHTH PGLLRGGAGG LGIMGLPPLP APGEPCPLAQ EEVIEINRAD   660
PRPNGDPAAA ALAHEDCPAI DQPAMSPEDK SPITPGSRGR YSRDRACFLL TDYAPSPDGS   720
IRKATGAPPL PPQDWRKPGP PSFLPDLNAN AAAWISP                           757
```

TISSUE SELECTIVE TRANSGENE EXPRESSION

CROSS-REFERENCE

This application is a continuation application of U.S. patent application Ser. No. 16/670,996, filed Oct. 31, 2019, which is a continuation application of U.S. patent application Ser. No. 16/153,433, filed Oct. 5, 2018, now U.S. Pat. No. 10,519,465, issued Dec. 31, 2019, which is a continuation application of International Application No. PCT/US2018/025940, filed Apr. 3, 2018, which claims the benefit of U.S. Provisional Application No. 62/480,998, filed on Apr. 3, 2017, which are incorporated herein by reference in their entireties.

SEQUENCE LISTING

The instant application contains a Sequence Listing which has been submitted electronically in XML format and is hereby incorporated by reference in its entirety. Said XML copy, created on Oct. 6, 2022, is named 46482-704-306_SL.xml and is 65,057 bytes in size.

BACKGROUND OF THE DISCLOSURE

Gene therapy has long been recognized for its enormous potential in how we approach and treat human diseases. Instead of relying on drugs or surgery, patients, especially those with underlying genetic factors, can be treated by directly targeting the underlying cause. Furthermore, by targeting the underlying genetic cause, gene therapy has the potential to effectively cure patients or provide sustained treatment over a longer period of time. Yet, despite this, clinical applications of gene therapy still require improvement in several aspects. One area of concern is off target effects. An attractive approach to address off target effects is to target gene expression of gene therapy to cell type(s) or tissue(s) of interest, or the target cell type(s) or tissue(s). As such, there is a need to identify elements and methods of use thereof for targeting gene therapy or gene expression to a tissue or cell type of interest.

SUMMARY OF THE DISCLOSURE

There exists a considerable need for targeting gene therapy and gene/transgene expression thereof to the desired tissue and/or cell type in vivo, which can decrease off-target effects, increase therapeutic efficacy in the target tissue and/or cell type, and increase patient safety and tolerance by lowering the effective dose needed to achieve efficacy.

Provided herein are compositions and methods for selective expression of a transgene in a target tissue or cell type over one or more non-target tissue or cell types. Compositions and methods for selective expression of a transgene comprise one or more regulatory elements (REs) which, when operably linked to a transgene (e.g., an ion channel subunit or a neurotransmitter regulator, or a syntaxin-binding protein), can facilitate or result in selective or preferential expression of the transgene in a target tissue or cell type (e.g., parvalbumin (PV) neurons) as compared to one or more non-target cell types (e.g., non-PV cells). In some cases, the REs are non-naturally occurring sequences. In some cases, the REs are human-derived regulatory elements. In some cases, the REs comprise a sequence from a non-human species, such as a monkey, a dog, a rabbit, or a mouse. In some cases, the compositions described herein are delivered into a cell in vivo, ex vivo, or in vitro using a viral vector and/or virus particles, such as adeno-associated virus (AAV) or lentivirus. In some cases, the compositions described herein are delivered into a cell as gene therapy. Also contemplated herein are methods and compositions for treating a neurological condition or disorder associated with a genetic defect in the CNS. In some cases, the relevant cell type or tissue affected by the genetic defect is a PV cell. In some instances, the neurological condition or disease is Dravet syndrome, Alzheimer's disease, epilepsy, epilepsy-related disorder, and/or seizures. In some cases, the neurological condition or disease is a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, the neurological condition or disease is any seizure and/or epilepsy related condition or disease wherein PV neurons are implicated.

In one aspect, the present disclosure contemplates a nucleic acid cassette comprising one or more regulatory elements operably linked to a transgene that results in selective expression in any target cell type, e.g., PV neurons in the CNS, over one or more non-target cell types, or non-PV cells in the CNS. In some cases, each regulatory element comprises (i) a sequence of SEQ ID NOS: 1-32, (ii) a functional fragment or a combination thereof, or (iii) a sequence with at least 80%, at least 85%, at least 90%, at least 91%, at least 92%, at least 93%, at least 94%, at least 95%, at least 96%, at least 97%, at least 98%, or at least 99% sequence identity to (i) or (ii). In some cases, sequence identity is determined using BLAST. In some cases, at least one of the regulatory elements is human derived. In some cases, at least one of the regulatory elements is derived from a non-human mammal. In some cases, the regulatory elements are non-naturally occurring. In some cases, the regulatory elements result in selective expression of the transgene in PV neurons that is greater than expression of the same transgene when operably linked to a non-selective regulatory element, as measured by a co-localization assay. In some cases, the non-selective regulatory element is a constitutive promoter. In some cases, the non-selective regulatory element is any one of CAG, EF1α, SV40, CMV, UBC, PGK, and CBA. In some instances, the regulatory element results in selective expression of the transgene in PV neurons at a level that is at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, or at least 20 fold as compared to selective expression of the transgene in PV neurons when operably linked to a non-selective regulatory element, as measured by the co-localization assay. In some cases, the regulatory element results in selective expression in PV neurons that is at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% higher than expression in PV neurons when the transgene is operably linked to a non-selective regulatory element. In some cases, the regulatory element results in selective expression in PV neurons that is about 1.5 times, 2 times, 2.5 times, 3 times, 3.5 times, 4 times, 4.5 times, 5 times, 5.5 times, 6 times, 6.5 times, 7 times, 7.5 times, 8 times, 8.5 times, 9 times, 9.5 times, 10 times, 15 times, 20 times, 25 times, 30 times, 40 times, 50 times, or 100 times higher than expected for natural distribution of PV neurons in the CNS. In some cases, the co-localization assay is an immunohistochemical assay. In some cases, the immunohistochemical assay comprises an anti-PV antibody. In some cases, the co-localization assay is performed as shown in Example 5 below. In some cases, the transgene encodes an ion channel subunit, a neurotransmitter regulator, a DNA binding domain, a gene editing protein, or a variant or a functional fragment thereof. In some cases, the ion channel subunit is an alpha subunit or a beta subunit of a sodium ion channel or a subunit of a potassium ion channel. In some cases, the transgene encodes any one of (i) amino acid sequences SEQ ID NOS: 37-43; (ii) a functional fragment thereof; or (iii) a sequence having at least 80% sequence identity to (i) or (ii). In some cases, sequence identity is determined using BLAST. In some cases, the transgene comprises (i) SCN1A, SCN2A, SCN8A, SCN1B, SCN2B, KV3.1, or KV3.3; (ii) a functional fragment thereof; or (iii) a sequence having at least 80% sequence identity to (i) or (ii). In some cases, the transgene encodes a neurotransmitter regulator that comprises (i) STXBP1, (ii) a functional fragment thereof, or (iii) a sequence having at least 80% sequence identity to (i) or (ii). In some cases, the transgene comprises a DNA-binding protein that modulates expression of an endogenous gene. In some cases, the endogenous gene is SCN1A, SCN2A, SCN8A, SCN1B, SCN2B, KV3.1, KV3.2, KV3.3, or STXBP1. In some cases, the transgene encodes a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the transgene comprises a DNA-binding domain linked to a transcriptional modulating domain (e.g., a transcriptional activator or repressor domain). In some cases, the gene editing protein is a Cas protein. In some cases, the regulatory elements combined are less than 2.5 kb, less than 2 kb, less than 1.5 kb, less than 1 kb, or less than 500 bp in size. In some cases, the non-PV cells comprise one or more of non-PV cell types in the CNS. In some cases, the non-PV cells comprise one or more of excitatory neurons, dopaminergic neurons, astrocytes, microglia, and motor neurons. In some cases, the nucleic acid cassette is a linear construct. In some cases, the nucleic acid cassette is a vector. In some cases, the vector is a plasmid. In some cases, the vector is a viral vector. In some cases, the viral vector is an adeno-associated virus (AAV) vector. In some cases, the AAV vector is AAV1, AAV8, AAV9, scAAV1, scAAV8, or scAAV9. In some cases, the viral vector is a lentiviral vector.

In one aspect, regulatory elements of any of the nucleic acid cassettes disclosed herein contain less than 600 bp of contiguous sequence from within 10 kb of the transcription start site of GAD2, GAD1, SYN1, NKX2.1, DLX1, DLX5/6, SST, PV, and/or VIP.

In one aspect, a method of treating a neurological disorder or condition in a subject in need thereof comprises delivering a therapeutically effective amount of any of the nucleic acid cassette disclosed herein. In some cases, the neurological disorder or condition is a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., chronic traumatic encephalopathy, generalized epilepsy with febrile seizures plus (GEFS+), epileptic encephalopathy, temporal lobe epilepsy, focal epilepsy, tuberous sclerosis); or a neurodegenerative disease (e.g., Alzheimer's disease, Parkinson's disease). In some cases, the neurological disorder or condition is Dravet syndrome or Alzheimer's disease. In some cases, the neurological condition or disease is any seizure and/or epilepsy related condition or disease wherein PV neurons are implicated.

In one aspect, a method of increasing selective expression of a transgene in PV neurons in CNS comprises contacting a cell with a nucleic acid cassette disclosed herein.

In some aspects, the present disclosure contemplates a method of targeting expression of any transgene to PV neurons in the CNS, the method comprising operably linking one or more PV neuron selective regulatory elements to a transgene. In some cases, each of the regulatory elements comprises (i) a sequence of any one of SEQ ID NOS: 1-32, (ii) a functional fragment or a combination thereof, or (iii) a sequence with at least 80%, at least 85%, at least 90%, at least 91%, at least 92%, at least 93%, at least 94%, at least 95%, at least 96%, at least 97%, at least 98%, or at least 99% sequence identity to (i) or (ii). In some cases, sequence identity is determined using BLAST. In some cases, the regulatory elements result in selective expression of the transgene in PV neurons that is greater than expression of the same transgene when operably linked to a non-selective regulatory element, as measured by a co-localization assay. In some cases, the immunohistochemical assay comprises an anti-PV antibody (e.g., as described in Example 5 below). In some cases, the non-selective regulatory element is a constitutive promoter. In some cases, the non-selective regulatory element is any one of CAG, EF1a, SV40, CMV, UBC, PGK, and CBA. In some cases, the regulatory elements result in selective expression of the transgene in PV neurons at a level that is at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, or at least 20 fold as compared to a non-selective regulatory element when operably linked to the transgene, as measured by a co-localization assay. In some cases, the regulatory elements result in selective expression in PV neurons that is at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% higher than expression in PV neurons when the transgene is operably linked to a non-selective regulatory element. In some cases, the regulatory elements result in selective expression in PV neurons that is about 1.5 times, 2 times, 2.5 times, 3 times, 3.5 times, 4 times, 4.5 times, 5 times, 5.5 times, 6 times, 6.5 times, 7 times, 7.5 times, 8 times, 8.5 times, 9 times, 9.5 times, 10 times, 15 times, 20 times, 25 times, 30 times, 40 times, 50 times, or 100 times higher than expected for natural distribution of PV neurons in CNS. In some cases, the transgene is any one of SCN1A, SCN2A, SCN8A, SCN1B, SCN2B, KV3.1, KV3.3, STXBP1, a DNA binding protein, a gene editing protein, or a functional fragment thereof. In some cases, the regulatory elements and the transgene are in an AAV. In some cases, the AAV is AAV1, AAV8, AAV9, scAAV1, scAAV8, or scAAV9.

In another aspect, the present disclosure contemplates a method of treating a neurological condition or disorder in a subject in need thereof, the method comprising contacting a cell with a nucleic acid cassette comprising: one or more regulatory elements operably linked to a transgene that result in selective expression of the transgene in PV neurons over one or more non-PV cells in CNS. In some cases, each of the regulatory elements comprises (i) a sequence of SEQ ID NOS: 1-32, (ii) a functional fragment or a combination thereof, or (iii) a sequence with at least 80%, at least 85%, at least 90%, at least 91%, at least 92%, at least 93%, at least 94%, at least 95%, at least 96%, at least 97%, at least 98%, or at least 99% sequence identity to (i) or (ii). In some cases, sequence identity is determined using BLAST. In some cases, the transgene is a voltage-gated ion channel subunit, or a variant or a functional fragment thereof. In some cases, the subunit is a beta subunit of a sodium ion channel. In some cases, the subunit is an alpha subunit of a sodium ion channel. In some cases, the subunit is of a potassium ion channel. In some cases, the transgene is any one of (i) SCN1A, SCN1B, SCN2B, KV3.1, or KV3.3; (ii) a functional fragment thereof; or (iii) a sequence having at least 80% sequence identity to (i) or (ii). In some cases, the transgene is a DNA binding protein. In some cases, the DNA binding protein modulates an endogenous gene. In some cases, the endogenous gene is SCN1A, SCN2A, SCN8A, SCN1B, SCN2B, KV3.1, KV3.3, or STXBP1. In some cases, the transgene is a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the transgene comprises a DNA binding domain linked to a transcriptional modulating domain (e.g., a transcriptional activator or repressor domain). In some cases, the transgene is a gene-editing protein. In some cases, the gene editing protein is a Cas protein, e.g., Cas9. In some cases, the neurological condition or disorder is associated with a haploinsufficiency or a mutation in any of SCN1A, SCN2A, SCN8A, SCN1B, SCN2B, KV3.1, KV3.3, or STXBP1. In some cases, the neurological condition or disorder is epilepsy, neurodegeneration, tauopathy, or neuronal hypoexcitability. In some cases, the neurological condition or disorder is Dravet syndrome. In some cases, the neurological condition or disorder is Alzheimer's disease. In some cases, the neurological condition or disease is a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, the neurological condition or disease is any seizure and/or epilepsy related condition or disease wherein PV neurons are implicated. In some cases, the regulatory elements of this disclosure result in selective expression of the transgene in PV neurons that is greater than expression of the same transgene when operably linked to a non-selective regulatory element, as measured by a co-localization assay. In some cases, the non-selective regulatory element is a constitutive promoter. In some cases, the non-selective regulatory element is any one of CAG, EF1a, SV40, CMV, UBC, PGK, and CBA. In some cases, the regulatory elements result in selective expression in PV neurons at a level that is at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, or at least 20 fold as compared to a non-selective regulatory element when operably linked to the transgene, as measured by a co-localization assay. In some cases, the regulatory elements result in selective expression in PV neurons that is at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% higher than expression in PV neurons when the transgene is operably linked to a non-selective regulatory element. In some cases, the regulatory elements result in selective expression in PV neurons that is about 1.5 times, 2 times, 2.5 times, 3 times, 3.5 times, 4 times, 4.5 times, 5 times, 5.5 times, 6 times, 6.5 times, 7 times, 7.5 times, 8 times, 8.5 times, 9 times, 9.5 times, 10 times, 15 times, 20 times, 25 times, 30 times, 40 times, 50 times, or 100 times higher than expected for natural distribution of PV neurons in CNS. In some cases, the nucleic acid cassette is in an AAV. In some cases, the AAV is AAV1, AAV8, AAV9, scAAV1, scAAV8, or scAAV9.

In one aspect, the present disclosure provides a method of treating Dravet syndrome, comprising contacting a cell with an AAV comprising a transgene, wherein the transgene is any one of (i) SCN1A, SCN2A, SCN8A, SCN1B, SCN2B, or a DNA binding protein, (ii) a functional fragment thereof, or (iii) a sequence having at least 80%, at least 85%, at least 90%, at least 91%, at least 92%, at least 93%, at least 94%, at least 95%, at least 96%, at least 97%, at least 98%, or at least 99% sequence identity to (i) or (ii). In some cases, sequence identity is measured using BLAST. In some cases, the DNA binding protein modulates an endogenous gene. In some cases, the DNA binding protein is a transcriptional modulator. In some cases, the transgene is a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene comprises a gene editing protein, e.g., a Cas protein, Cas9. In some cases, the endogenous gene is SCN1A, SCN2A, SCN8A, SCN1B, or SCN2B. In some cases, the AAV further comprises one or more PV neuron selective regulatory elements or one or more regulatory elements disclosed herein operably linked to the transgene. In some cases, each of the regulatory elements independently comprises (i) a sequence of any one of SEQ ID NOS: 1-32, (ii) a functional fragment or a combination thereof, or (iii) a sequence with at least 80%, at least 85%, at least 90%, at least 91%, at least 92%, at least 93%, at least 94%, at least 95%, at least 96%, at least 97%, at least 98%, or at least 99% sequence identity to (i) or (ii).

In another aspect, the present disclosure provides a method of treating Alzheimer's disease, comprising contacting a cell with an AAV comprising a transgene, wherein the transgene is any one of (i) SCN1A, SCN2A, SCN8A, SCN1B, SCN2B, KV3.1, KV3.3, STXBP1, or a nucleic acid sequence encoding a DNA binding protein; (ii) a functional fragment thereof; or (iii) a sequence having at least 80%, at least 85%, at least 90%, at least 91%, at least 92%, at least 93%, at least 94%, at least 95%, at least 96%, at least 97%, at least 98%, or at least 99% sequence identity to (i) or (ii). In some cases, sequence identity is measured using BLAST. In some cases, the DNA binding protein modulates an endogenous gene. In some cases, the endogenous gene is SCN1A, SCN2A, SCN8A, SCN1B, SCN2B, KV3.1, KV3.3, or STXBP1. In some cases, the transgene is a DNA-binding protein comprising a transcriptional modulator. In some cases, the transgene is a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene comprises a gene editing protein, e.g., a Cas protein, Cas9. In some cases, the AAV further comprises one or more PV neuron selective regulatory elements or one or more regulatory elements disclosed herein operably linked to the transgene. In some cases, each of the regulatory elements independently comprises each of the regulatory elements independently comprises (i) a sequence of any one of SEQ ID NOS: 1-32, (ii) a functional fragment or a combination thereof, or (iii) a sequence with at least 80%, at least 85%, at least 90%, at least 91%, at least 92%, at least 93%, at least 94%, at least 95%, at least 96%, at least 97%, at least 98%, or at least 99% sequence identity to (i) or (ii).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5A illustrates the immunofluorescence co-localization assay performed with AAVDJ comprising one of SEQ ID NO: 2, SEQ ID NO: 3, SEQ ID NO: 4, and SEQ ID NO: 5 operably linked to eGFP. FIG. 5B illustrates the immunofluorescence co-localization assay performed with AAVDJ comprising one of SEQ ID NO: 6, SEQ ID NO: 7, and SEQ ID NO: 9 operably linked to eGFP. FIG. 5C illustrates the immunofluorescence co-localization assay performed with AAVDJ comprising one of SEQ ID NO: 10, SEQ ID NO: 11, SEQ ID NO: 12, and SEQ ID NO: 13 operably linked to eGFP. FIG. 5D illustrates the immunofluorescence co-localization assay performed with AAVDJ comprising one of SEQ ID NO: 14, SEQ ID NO: 15, SEQ ID NO: 16, and SEQ ID NO: 17 operably linked to eGFP. FIG. 5E illustrates the immunofluorescence co-localization assay performed with AAVDJ comprising one of SEQ ID NO: 18, SEQ ID NO: 19, SEQ ID NO: 20, and SEQ ID NO: 21 operably linked to eGFP. FIG. 5F illustrates the immunofluorescence co-localization assay performed with AAVDJ comprising SEQ ID NO: 22 or SEQ ID NO: 34 operably linked to eGFP, wherein SEQ ID NO: 34 is a previously characterized non-selective regulatory element and was used as a control for comparison.

DETAILED DESCRIPTION OF THE DISCLOSURE

Figure 1:
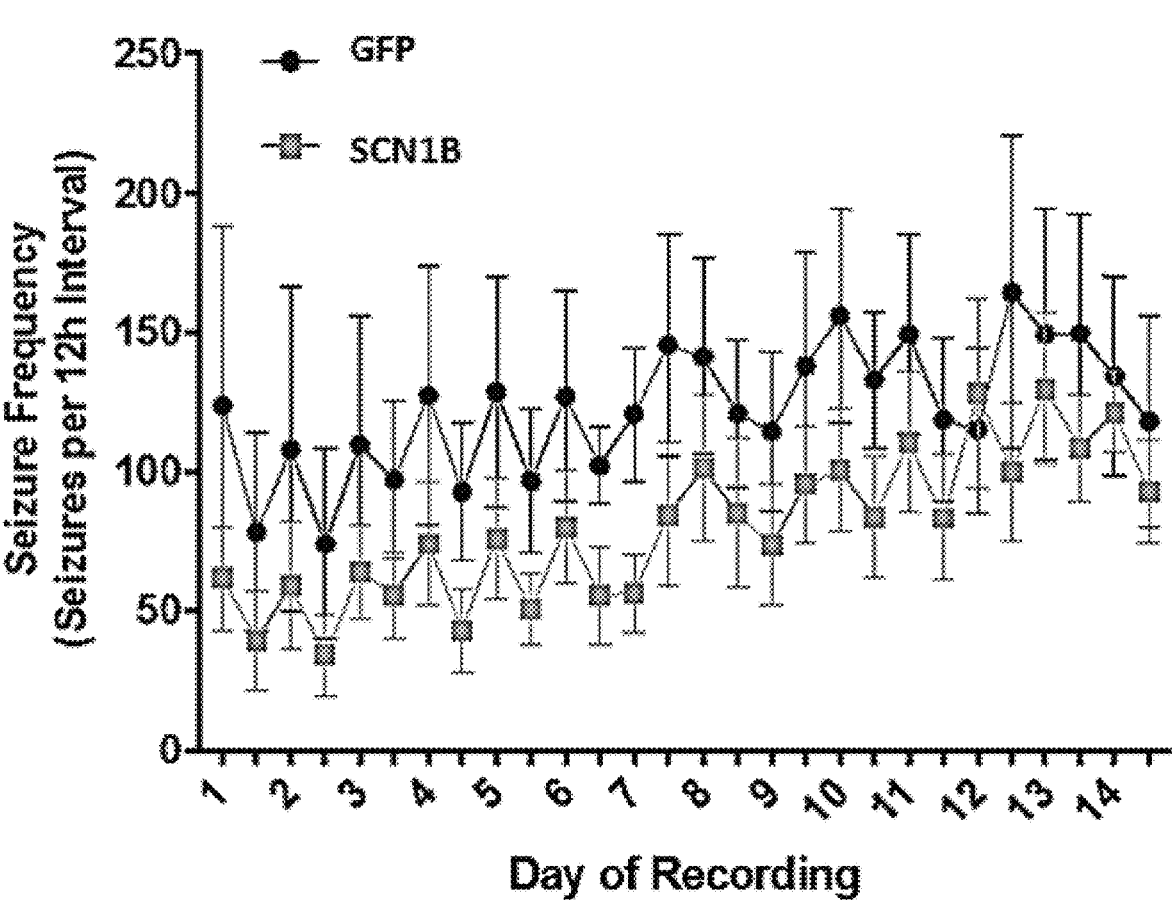
FIG. 1 illustrates the frequency of seizures (seizures per 12 hr interval) in SCN1A heterozygous mice after treatment with a recombinant AAVDJ vector comprising either SCN1B or eGFP operably linked to a regulatory element comprising a sequence of SEQ ID NO: 32. The graph illustrates the mean values at each day of recording with error bars representing the standard error of the mean.

The present disclosure contemplates compositions and methods of using such compositions in gene therapy to treat a disease or condition associated with the central nervous system (CNS), e.g., Dravet syndrome, Alzheimer's disease, epilepsy, and/or seizures.

Gene therapy can replace, modify, delete, or add a gene or a specific nucleic acid sequence, such as an expression cassette, to impart a therapeutic effect in a cell. In some cases, gene therapy is used to deliver an expression cassette into a cell that produces or results in a therapeutic effect. In some cases, a virus, such as AAV, comprising a viral vector that comprises an expression cassette can be used to deliver a transgene into a cell. The expression cassette can contain a transgene that provides a therapeutic effect when expressed in a cell.

One challenge in gene therapy is ensuring that the transgene is expressed in an appropriate cell type of interest, or the target cell type, to effect or target gene expression. Traditional methods for targeting gene therapy have often relied on delivery methods and/or vehicles (e.g., varying the viruses used or capsid sequences of viruses). In addition to targeting, or selective expression, of an expression cassette in the target cell type over one or more non-target cell types, another challenge in the field is increasing gene expression, especially when the gene is large, in a target cell type or tissue to exert a therapeutic effect.

The present disclosure provides a plurality of regulatory elements, which are non-coding nucleotide sequences, that can be operably linked to any transgene to increase or to improve selectivity of the transgene expression in the CNS, e.g., in PV neurons. By increasing selectivity of gene expression using one or more regulatory elements disclosed herein, one can improve the efficacy of a gene therapy, decrease the effective dose needed to result in a therapeutic effect, minimize adverse effects or off-target effect, and/or increase patient safety and/or tolerance.

In one aspect, one or more regulatory elements can be operably linked to any transgene in an expression cassette to modulate gene expression in a cell, such as targeting expression of the transgene in a target cell type or tissue (e.g., PV cells) over one or more non-target cell type or tissue (e.g., non-PV CNS cell-types). In some cases, targeting expression of the transgene in a target cell type or tissue includes increased gene expression in the target cell type or tissue. One or more regulatory elements operably linked to a transgene can be part of an expression cassette, which can be a linear or a circular construct, a plasmid, a vector, a viral vector, e.g., a vector of an adeno-associated virus (AAV). Such expression cassette can be adapted for gene therapy or delivery into a subject (e.g., a human, a patient, or a mammal). In some cases, operably linking one or more regulatory elements to a gene results in targeted expression of the gene in a target tissue or cell type in the CNS, such as a parvalbumin (PV) neuron. In some cases, one or more regulatory elements (e.g., SEQ ID NOS: 1-32, or a functional fragment or a combination thereof, or sequences having at least 80%, at least 90%, at least 95%, or at least 99% sequence identity thereto) increase selectivity of gene expression in a target tissue or cell type in the CNS, such as PV neurons. In some cases, a gene therapy comprises one or more regulatory elements disclosed herein, wherein the regulatory elements are operably linked to a transgene and drive selective expression of the transgene in PV neurons.

In some cases, selective expression of a gene in PV neurons is used to treat a disease or condition associated with a haploinsufficiency and/or a genetic defect in an endogenous gene, wherein the genetic defect can be a mutation in the gene or dysregulation of the gene. Such genetic defect can result in a reduced level of the gene product and/or a gene product with impaired function and/or activity. In some cases, an expression cassette comprises a gene, a subunit, a variant or a functional fragment thereof, wherein gene expression from the expression cassette is used to treat the disease or condition associated with the genetic defect, impaired function and/or activity, and/or dysregulation of the endogenous gene. In some cases, the disease or condition is Dravet syndrome, Alzheimer's disease, epilepsy, neurodegeneration, tauopathy, neuronal hypoexcitability and/or seizures.

In some cases, the transgene encodes an ion channel or a neurotransmitter regulator, a DNA binding protein, or a subunit, variant, or functional fragment thereof. In some cases, the transgene is a sodium ion channel alpha subunit, sodium ion channel beta subunit, or a variant or functional fragment thereof. In some cases, the transgene is a potassium ion channel or a subunit thereof. In some cases, the transgene is SCN1A, SCN2A, SCN8A, SCN1B, SCN2B, KV3.1, KV3.2, KV3.3, STXBP1, or nucleic acid sequence encoding a DNA binding protein (e.g., a DNA binding protein that modulates expression of an endogenous gene), or a variant or functional fragment thereof. In some cases, the transgene comprises a sequence having at least 80%, at least 85%, at least 90%, at least 95%, at least 96%, at least 97%, at least 98%, or at least 99% sequence identity to any one of SCN1A, SCN2A, SCN8A, SCN1B, SCN2B, KV3.1, KV3.2, KV3.3, STXBP1, a nucleic acid sequences encoding a DNA binding protein, or a variant or functional fragment thereof. In some cases, the transgene encodes a DNA binding protein that modulates expression of an endogenous gene, such as any one of SCN1A, SCN2A, SCN8A, SCN1B, SCN2B, KV3.1, KV3.2, KV3.3, and STXBP1.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, up to 15%, up to 10%, up to 5%, or up to 1%) of a given value.

The terms "determining", "measuring", "evaluating", "assessing", "assaying", "analyzing", and their grammatical equivalents can be used interchangeably herein to refer to any form of measurement, and include determining if an element is present or not (for example, detection). These terms can include both quantitative and/or qualitative determinations. Assessing may be relative or absolute.

The term "expression" refers to the process by which a nucleic acid sequence or a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "operably linked", "operable linkage", "operatively linked", or grammatical equivalents thereof refer to juxtaposition of genetic elements, e.g., a promoter, an enhancer, a polyadenylation sequence, etc., wherein the elements are in a relationship permitting them to operate in the expected manner. For instance, a regulatory element, which can comprise promoter and/or enhancer sequences, is operatively linked to a coding region if the regulatory element helps initiate transcription of the coding sequence. There may be intervening residues between the regulatory element and coding region so long as this functional relationship is maintained.

A "vector" as used herein refers to a macromolecule or association of macromolecules that comprises or associates with a polynucleotide and which can be used to mediate delivery of the polynucleotide to a cell. Examples of vectors include plasmids, viral vectors, liposomes, and other gene delivery vehicles. The vector generally comprises genetic elements, e.g., regulatory elements, operatively linked to a gene to facilitate expression of the gene in a target. The combination of regulatory elements and a gene or genes to which they are operably linked for expression is referred to as an "expression cassette".

The term "AAV" is an abbreviation for adeno-associated virus, and may be used to refer to the virus itself or a derivative thereof. The term covers all serotypes, subtypes, and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV1, AAV2, AAV3, AAV4, AAV5, AAV6, AAV7, AAV8, AAV9, AAV10, AAV11, AAV12, rh10, and hybrids thereof, avian AAV, bovine AAV, canine AAV, equine AAV, primate AAV, non-primate AAV, and ovine AAV. The genomic sequences of various serotypes of AAV, as well as the sequences of the native terminal repeats (TRs), Rep proteins, and capsid subunits are known in the art. Such sequences may be found in the literature or in public databases such as GenBank. An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs). The term rAAV vector encompasses both rAAV vector particles and rAAV vector plasmids. An rAAV vector may either be single-stranded (ssAAV) or self-complementary (scAAV). An "AAV virus" or "AAV viral particle" or "rAAV vector particle" refers to a viral particle composed of at least one AAV capsid protein and an encapsidated polynucleotide rAAV vector. If the particle comprises a heterologous polynucleotide (i.e., a polynucleotide other than a wild-type AAV genome such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

As used herein, the terms "treat", "treatment", "therapy" and the like refer to obtaining a desired pharmacologic and/or physiologic effect, including, but not limited to, alleviating, delaying or slowing the progression, reducing the effects or symptoms, preventing onset, inhibiting, ameliorating the onset of a diseases or disorder, obtaining a beneficial or desired result with respect to a disease, disorder, or medical condition, such as a therapeutic benefit and/or a prophylactic benefit. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some cases, for prophylactic benefit, the compositions are administered to a subject at risk of developing a particular disease, or to a subject reporting one or more of the physiological symptoms of a disease, even though a diagnosis of this disease may not have been made. The methods of the present disclosure may be used with any mammal. In some cases, the treatment can result in a decrease or cessation of symptoms (e.g., a reduction in the frequency or duration of seizures). A prophylactic effect includes delaying or eliminating the appearance of a disease or condition, delaying or eliminating the onset of symptoms of a disease or condition, slowing, halting, or reversing the progression of a disease or condition, or any combination thereof.

The term "effective amount" or "therapeutically effective amount" refers to that amount of a composition described herein that is sufficient to affect the intended application, including but not limited to disease treatment, as defined below. The therapeutically effective amount may vary depending upon the intended treatment application (in vivo) or the subject and disease condition being treated, e.g., the weight and age of the subject, the severity of the disease condition, the manner of administration and the like, which can readily be determined by one of ordinary skill in the art. The term also applies to a dose that will induce a particular response in a target cell. The specific dose will vary depending on the particular composition chosen, the dosing regimen to be followed, whether it is administered in combination with other compounds, timing of administration, the tissue to which it is administered, and the physical delivery system in which it is carried.

A "fragment" of a nucleotide or peptide sequence is meant to refer to a sequence that is less than that believed to be the "full-length" sequence.

A "variant" of a molecule refers to allelic variations of such sequences, that is, a sequence substantially similar in structure and biological activity to either the entire molecule, or to a fragment thereof.

The term "functional fragment" is intended to include the "fragments", "variants", "analogues", or "chemical derivatives" of a molecule.

A "functional fragment" of a DNA or protein sequence possesses at least a biologically active fragment of the sequence, which refers to a fragment that retains a biological activity (either functional or structural) that is substantially similar to a biological activity of the full-length DNA or protein sequence. A biological activity of a DNA sequence can be its ability to influence expression in a manner known to be attributed to the full-length sequence. For example, a functional fragment of a regulatory element will retain the ability to influence transcription as the full-length RE.

The terms "subject" and "individual" are used interchangeably herein to refer to a vertebrate, preferably a mammal, more preferably a human. "Subject" refers to an animal, such as a mammal, for example a human. The methods described herein can be useful in human therapeutics, veterinary applications, and/or preclinical studies in animal models of a disease or condition. In some case, the subject is a mammal, and in some cases, the subject is human.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells, alive or dead, are employed. In vitro assays also encompass a cell-free assay in which no intact cells are employed.

Sequence comparisons, such as for the purpose of assessing identities, mutations, or where one or more positions of a test sequence fall relative to one or more specified positions of a reference sequence, may be performed by any suitable alignment algorithm, including but not limited to the Needleman-Wunsch algorithm (see, e.g., the EMBOSS Needle aligner available at www.ebi.ac.uk/Tools/psa/emboss_needle/, optionally with default settings), the BLAST algorithm (see, e.g., the BLAST alignment tool available at blast.ncbi.nlm.nih.gov/Blast.cgi, optionally with default settings), and the Smith-Waterman algorithm (see, e.g., the EMBOSS Water aligner available at www.ebi.ac.uk/Tools/psa/emboss_water/, optionally with default settings). Optimal alignment may be assessed using any suitable parameters of a chosen algorithm, including default parameters.

In general, "sequence identity" or "sequence homology", which can be used interchangeably, refer to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity", also referred to as "percent homology". The percent identity to a reference sequence (e.g., nucleic acid or amino acid sequences), which may be a sequence within a longer molecule (e.g., polynucleotide or polypeptide), may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, *Proc. Natl. Acad. Sci. USA* 87:2264-2268 (1990) and as discussed in Altschul, et al., *J. Mol. Biol.* 215:403-410 (1990); Karlin and Altschul, *Proc. Natl. Acad. Sci. USA*

90:5873-5877 (1993); and Altschul et al., *Nucleic Acids Res.* 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, *Computers and Chemistry* 17: 149-163 (1993). Ranges of desired degrees of sequence identity are approximately 80% to 100% and integer values there between. Typically, the percent identities between a disclosed sequence and a claimed sequence are at least 80%, at least 85%, at least 90%, at least 95%, at least 98%, or at least 99%. In general, an exact match indicates 100% identity over the length of the reference sequence. In some cases, reference to percent sequence identity refers to sequence identity as measured using BLAST (Basic Local Alignment Search Tool). In other cases, ClustalW can be used for multiple sequence alignment.

Unless otherwise indicated, all terms used herein have the same meaning as they would to one skilled in the art and the practice of the present invention will employ, conventional techniques of molecular biology, microbiology, and recombinant DNA technology, which are within the knowledge of those of skill of the art.

Regulatory Elements

Regulatory elements are nucleic acid sequences or genetic elements which are capable of influencing (e.g., increasing or decreasing) expression of a gene and/or confer selective expression of a gene (e.g., a reporter gene such as eGFP, a transgene, or a therapeutic gene) in a particular tissue or cell type of interest. In some cases, a regulatory element can be a transgene, an intron, a promoter, an enhancer, UTR, insulator, a repressor, an inverted terminal repeat (ITR) sequence, a long terminal repeat sequence (LTR), stability element, posttranslational response element, or a polyA sequence, or a combination thereof. In some cases, the regulatory element is a promoter or an enhancer, or a combination thereof. In some cases, the regulatory element is derived from a human sequence.

In some cases, the cell type of interest is a PV neuron. Regulatory elements can function at the DNA and/or the RNA level. Regulatory elements can function to modulate gene expression selectivity in a cell type of interest. Regulatory elements can function to modulate gene expression at the transcriptional phase, post-transcriptional phase, or at the translational phase of gene expression. Regulatory elements include, but are not limited to, promoter, enhancer, repressor, silencer, and insulator sequences. At the RNA level, regulation can occur at the level of translation (e.g., stability elements that stabilize mRNA for translation), RNA cleavage, RNA splicing, and/or transcriptional termination. In some cases, regulatory elements can recruit transcriptional factors to a coding region that increase gene expression selectivity in a cell type of interest. In some cases, regulatory elements can increase the rate at which RNA transcripts are produced, increase the stability of RNA produced, and/or increase the rate of protein synthesis from RNA transcripts. In some cases, regulatory elements can prevent RNA degradation and/or increase its stability to facilitate protein synthesis. In some cases, regulatory elements suppress transcription and/or translation processes in off-target cell-types. In some cases, off-target cell-types include, but are not limited to, excitatory neurons, non-PV CNS cell types, and non-neuronal CNS cell types.

Various assays including, but not limited to, DNAase hypersensitivity, ATAC-Seq, and ChIP-Seq can be used to identify putative non-coding regulatory elements (REs). The enzymatic reaction in each of these assays preferentially targets open/accessible chromatin states, a state which is thought to be predictive of regulatory elements. To discover cell-type-selective regulatory elements, one can assay for open chromatin sequence for target cell-type of interest (e.g., parvalbumin neurons) and compare that to open chromatin sequences for non-target cell types (e.g., excitatory neurons). Additional filters can be applied to further refine target selection, including proximity to a cell-type selective gene, species conservation, and/or sequence motifs, such as transcription factor binding sites. DNA sequences that are uniquely identified in the target cell type can be synthesized and cloned into an expression vector. The selectivity of a regulatory element can be determined using immunohistochemical methods to quantify co-localization to known cell-type selective proteins.

For example, one method of isolating a cell-type-selective regulatory element includes isolating nuclei from a brain tissue or cell type of interest from an animal model, which can be achieved by using an affinity purification method that isolates the tissue or cell type of interest (e.g., using beads coated to an anti-PV antibody for isolating PV neurons), using high-throughput natural priming and DNA synthesis to generate a pool of sequences from open chromatin regions in the nuclei, sequencing the pool of sequences to identify putative sequences that drive gene expression in the tissue or cell type of interest, and verifying selective expression in a reporter system in a cell line in vitro and/or in an animal model.

Another method for identifying candidate regulatory elements that are selective in a tissue or cell type of interest include using R26-CAG-LSL-Sun1-sfGFP-Myc knock-in mouse for harvesting the tissue or cell type of interest, isolating GFP+/Myc+ nuclei from the mouse neocortex of this strain using affinity purification, e.g., using anti-GFP or anti-Myc antibodies and protein G-coated magnetic beads to isolate nuclei from the neocortex. Nuclear RNA from purified nuclei or whole neocortical nuclei can be converted to cDNA and amplified with the Nugen Ovation RNA-seq System V2 (Nugen 7102), followed by sequencing using the Illumina HISEQ® 2500. Genomic DNA from purified nuclei can be fragmented and used to make MethylC-seq libraries, which can be sequenced using the Illumina HISEQ® 2000. To generate an ATAC-seq library, nuclei bound to beads are transposed using Tn5 transposase (Illumina FC-121-1030). After 9-12 cycles of PCR amplification, libraries are sequenced using an Illumina HISEQ® 2500. To generate a ChIP-seq library, excitatory neuron nuclei can be digested to mononucleosomes using micrococcal nuclease, followed by salt extraction of chromatin, and native ChIP and library construction, which can be sequenced on an Illumina HISEQ® 2500. After sequencing these libraries, the sequences are mapped to identify, for example, correlation in cell-type-specific hypo-methylation in CG-rich regions, histone modifications, transcription factor binding sites, and patterns associated with highly expressed transcriptional factors. Overlapping features and correlations from multiple assays and/or libraries described above provide evidence for identifying candidate sequences within such genomic regions as potential regulatory elements associated with selective expression and/or high expression in the cells isolated from the neocortex. For example, a genomic region characterized by a strong overlap between hypomethylation detected in the methyl C-seq library, ChIP assay, and an enrichment in transcription factor binding motifs in the same region provide convergent data that indicate the genomic region contains a sequence of a putative regulatory element selective for the tissue or cell type isolated. As another example, to identify candidate PV neuron selective regulatory elements, one can isolate PV neurons and purify nuclei from the isolated PV cells so that genomic sequences that are identified as active in multiple sequencing assays described above have a high likelihood of being PV cell-selective regulatory elements, e.g., a genomic region that is identified as active in an ATAC-seq assay (corresponding to regions of open chromatin), active in RNA-seq (indicative of active gene expression and low DNA methylation patterns in the region), and active in methylC-seq assay (which generates single-base resolution methylome maps from a cell type of interest).

Once candidate genomic regions are identified as selectively active in a cell type of interest, sequences within the region can be generated using PCR methods and tested in additional assays in vitro and/or in vivo to validate tissue or cell type selectivity of the sequences. Such validation assays include immunohistochemical co-localization assay, wherein an antibody or any detectable marker is used to label the cell type of interest and a second detectable marker, e.g., a fluorescent transgene, is operably linked to the putative regulatory elements. Expression cassettes comprising such elements are delivered into cells in vitro and/or in vivo. Selective expression driven by one or more putative regulatory elements can be validated by measuring the overlap between the cell type of interest (as measured by the detectable signal or fluorescence from its labeled marker, e.g., an anti-PV antibody) and the second detectable marker corresponding to expression of the transgene (e.g., eGFP or RFP) operably linked to the regulatory elements. An overlap in the signals from both detectable markers indicates cell-type selectivity in the labeled cell type if the amount of overlap observed is higher than the overlap observed when the regulatory elements are replaced with a control, such as CAG, EF1a, a constitutive promoter (e.g., SV40, CMV, UBC, PGK, and CBA), a non-selective regulatory element, or a previously characterized non-selective regulatory element. Various mouse strains adapted for expressing a detectable marker in a cell type of interest allows validation of cell type selectivity of a regulatory element in vivo. For example, a number of mouse lines that express Cre in a particular cell type can be used because cell-type selective Cre expression can drive Cre-induced expression of a fluorescent protein, such as red fluorescent protein (RFP), in a cell type of interest. Labeling such cell type of interest in vivo allows one to determine level of cell-type-selective expression that is associated with a putative regulatory element operably linked to a fluorescent or reporter transgene in the same mouse. Similar to the co-localization assay, an overlap of the signals from both markers that exceeds the overlap detected for CAG, EF1a, a constitutive promoter (e.g., SV40, CMV, UBC, PGK, and CBA), or a non-selective regulatory element is indicative of cell-type selectivity for the regulatory elements tested. In some cases, the mouse strain used is B6 PV-Cre mouse (Jackson Laboratory), which is a B6 PV-Cre knock-in mouse that expresses Cre recombinase in parvalbumin-expressing neurons (e.g., interneurons in the brain and proprioceptive afferent sensory neurons in the dorsal root ganglia), without disrupting endogenous PV expression.

Upon validation of cell type selectivity of a regulatory element for a particular cell type, sequences of such regulatory elements can be varied using various mutagenesis methods, e.g., error-prone PCR methods, to improve its selectivity. In some cases, two or more regulatory elements having cell selectivity can be combined. In some cases, combined regulatory elements exhibit enhanced cell-type selectivity in driving gene expression in the cell type of interest. In some instances, such regulatory elements are truncated one or more bases at a time to determine the minimal amount of sequence that retains its cell type selectivity. Smaller regulatory elements that retain cell type selectivity are helpful for making gene therapy comprising a large transgene or where the cloning capacity of a vector or plasmid is limited in view of the size of a transgene that one wishes to deliver using gene therapy.

The present disclosure provides a plurality of nucleotide sequences that are regulatory elements. In some cases, any one or more of the regulatory elements disclosed herein result in increased selectivity in gene expression in a parvalbumin cell. In some cases, regulatory elements disclosed herein are PV-cell-selective. In some cases, PV cell selective regulatory elements are associated with selective gene expression in PV cells more than expression in non-PV CNS cell types. In some cases, PV-cell-selective regulatory elements are associated with reduced gene expression in non-PV CNS cell types.

Non-limiting examples of regulatory elements include SEQ ID NOS: 1-32, as provided in TABLE 1 below.

TABLE 1

| | List of nucleic acid sequences disclosed herein. | |
|---|---|---|
| SEQ ID NO: | Nucleic Acid Sequence | Source/ Genomic Location |
| 1 | GGAGGAAGCCATCAACTAAACTACAATGACTGTAAGATACAAA ATTGGGAATGGTAACATATTTTGAAGTTCTGTTGACATAAAGAA TCATGATATTAATGCCCATGGAAATGAAAGGGCGATCAACACT ATGGTTTGAAAAGGGGGAAATTGTAGAGCACAGATGTGTTCGT GTGGCAGTGTGCTGTCTCTAGCAATACTCAGAGAAGAGAGAGA ACAATGAAATTCTGATTGGCCCCAGTGTGAGCCCAGATGAGGTT CAGCTGCCAACTTTCTCTTTCACATCTTATGAAAGTCATTTAAGC ACAACTAACTTTTTTTTTTTTTTTTTTTTTTTGAGACAGAGTCTTG CTCTGTTGCCCAGGACAGAGTGCAGTAGTGACTCAATCTCGGCT CACTGCAGCCTCCACCTCCTAGGCTCAAACGGTCCTCCTGCATC AGCCTCCCAAGTAGCTGGAATTACAGGAGTGGCCCACCATGCC CAGCTAATTTTTGTATTTTTAATAGATACGGGGGTTTCACCATAT CACCCAGGCTGGTCTCGAACTCCTGGCCTCAAGTGATCCACCTG CCTCGGCCTCCCAAAGTGCTGGGATTATAGGCGTCAGCCACTAT GCCCAACCCGACCAACCTTTTTTAAAATAAATATTTAAAAAATT GGTATTTCACATATATACTAGT | Human; hg19: chr2: 171621900- 171622580 |
| 2 | AGTTTGGACAAGAACTATAGTTCTAGCTTTCTCTGGGTCTCCAC CTTGCAGAGAATGCAGCTTTCATTATCTCATGAGCCAAACTCTC ATCATCTCTTTCCATATATCTGTCGGTGCTCTTCCATGAGTACTC TAACACACACAGAAGGAGCACTTACACAGGCTGTTGTTTTTCTC TTATTATCATAGCTGTTGTTCAGACATGTGCATTCTGTTCTTGTT GCTTCAATGCTAAAGGAGTCTCAGGATATGAGAACTGTACCAG CCGAGGCATCAGGAAACATGGGTGGAAATTCCCACAGTACTAT TTGTTCACTGTGTGACCTTGGGCCAGTCACATCCCTTTCCTGAG GCTTCGATTCCCCAAGCTATAAAGAAGCATCTCTTAACCTTTT TTTAGGTCATGAGTCAGGCCCAGCACACTCTCAGGGAGACTCAT GAGAGTACAGATCATTTCCCATAGAAAAACCATAGTTTTATATC CAGAGGCTTTTCTGTAAG | Mouse; mm10: chr2: 36053858- 36054359 |
| 3 | GGTTCCAGTTCAGAGGCAGAGCATTTGGGGTTCCCAGTCAGGA GCTTTCCTCTCTCCGCTCCTTAGTTTCCTCTCTTTAAAAAAAAAT GGGTGATAGTATAGAAAGGAAGCTCTGGGCTCGGGGACCAGGG CCCTGGGATCCCCGCTCCCAGCCACTCGCTCCTGACCCTTCCAG GGACAAGCTCCCCCCCACCCCGTCCTTTCCAGGCTGCCACTAGA AGAGATGGGGACGCGTGGTCAGCCGCTTCTGTCGCCCCCCAGG GAACGGTCTCACGCTGGAGGGGGCAGTGCCCTCGGAACAGGAC AGTCAGCCCAAGCCAGCCAAGCGCGCGCGGACGTCCTTCACCG CAGAGCAATTGCAGGTACCCCGGGCAAGCCCCGAAGCGTGTGG GCGGGGCTTCGGAGTGGGCGTGGTTGTTCGGGACTTGTGACTCC GCCCCTTGTGCGGGGACCCGCGTGAGGCCGCTCCAAGGATGAA GCTGCCTGGGGCGTGGCCTCGGACCCTGAGCCTCTGATTGGGCG GAGGTCTCAGGGCCCTTCTGCGCCCCACAGGTTATGCAGGCGCA GTTCGCGCAGGACAACAACCCGGACGCGCAGACGCTGCAGAAG CTGGCGGACATGACGGGCCTCAGTCGCAGGGTCATCCAGGTGG GGCTCCGGGGTCTCGGCCTTCAGGTCTAGGGTGAACCTTAGGGA AGCGCTGAAGCTCGTAGTGGTACGGATGGTCGCGCGTGCACGT | Mouse; chr2: 36,091,144- 36,091,966 |

TABLE 1-continued

List of nucleic acid sequences disclosed herein.

| SEQ ID NO: | Nucleic Acid Sequence | Source/ Genomic Location |
|---|---|---|
| | GGCCGCCCCTCTCCAGTGTGGCCTAAGGACCCCAGTCGGCACG GGTTGACCCTTTTCCTTGATTACTGAGAGTGCAGAGGCTGT | |
| 4 | TGGTGGGAAGACATGTCCAGGGAAGAAATGGCCTCCAGAGGCC TGAGGTGGGGAAATGCTGGAGGTGGAGAGAGGAACAACTGACT GAAAATGAGCTTCCACTGTGGCTTAGTAGCCTATACCAAGTCTA GAGTATAGGGTAGGAGAAGATTAGGAAAGCGATGGGTCTGAGA ATGATGTGGCCTGTTGACTTTTGTAAACCCAAAGCACCTTGGAC TAAACCCTATGAACAGTGTGGTGCCACCAAAGACTATAATGAG CTCAGGGAACAGAATTCTGTGTGCATGGTGATTTTTTTTTTTTT TTCTGCTAACTGCAGTCTGGGTGATGCATTGACAAACCAATCCT GGAAAGTAAGAGGCAAGGGCAGCTGGGACGGTGAGAGGAGCC TGATGGGAACCAGGCCAAGCAGGGCAGCAGAGGCGATGAAGA GGATGTGGTGCATCCAGAGACTCACTTCATTAGCTGGAGGCACT GCTGGATAGGGTCTGAAGGTTCTGGTATCTGAGTTGGCGGGCTG GGTGAGTGGTGGCTCTGCTTCCTGAACAGTGTGTGCAAGAGGA AACAGGGTTAAGGGCTAGGACAGTCACAGGTGAGTCAGCCTCA CAAGAGCAACCTTCCCCTAGTGCAGA | Mouse; chr2: 36,095,396- 36,096,028 |
| 5 | GGAGGTCTCCTTTTGCCCCGGTTCCAACAAGAGAATGCAAGGCT GTATCTCAATTTCCTTGAGCCTCTCTGTATTATAGAAGAAAAGT AGGGAAGCCATACGCCCCTTCTGAGCTTCAGTGTCTCTCTGTCT CTGCAAATGAGGCTGGGGAGGCTGGGGCGGGCGTGAAAGAG GCCCGCGCCAAGCCGACCCCCACCTCTGCCCCCTCCCCAGGTCA ACAACCTCATCTGGCACGTGCGGTGCCTCGAGTGCTCCGTGTGT CGCACATCGCTGAGGCAGCAGAATAGCTGCTACATCAAGAACA AGGAGATCTACTGCAAGATGGACTACTTCAGGTAGGCAGCGGC CATCCCGCCAGCAAGCGCTGGAGCATGAACGCCTTGCACACGC GTGCCTAGGCCACTTGTGTGGCCTGTGCTCTCCAATTCCTGAGC CCTGCTGTTCAGAGTGCACAACGCGGCTCAGCGCACTGGCCCG GCCCTCCTACTCAGCACGTCTTACACAGAAGGGAGCGCCAGTCT CAGCCTGAGTTCTGGCGGGGGATCTGCCTCGGGTTCCTCCGATC TGACAGGCGCTGGCCACGGGTCTGGTTCCATCTCTGGTCTTTTC TGGCCCCGAGCACCAGTGTGTTCTGTTGAGCTCTGATGTCCGAG GCTCTGGCCCGGATCA | Mouse; mm10: chr2 36102524- 36103193 |
| 6 | CTCTGGCTACCTCTTATCTTGGGCATTCACGACAATTTCTAATTG CAGGTAGTTTGTGTGTGTGCGCGTGTTTTTTTTCCCCCTCAGAGG CTTGGATTGCAAAGGAACTAAGCGATTACTTCAAGAGCCACGG GTTAAGTGCAGGGAGAGGGGGAGAGAGAGGGAAAAAAACCCA ATCCAAATTCAAATTGCTTCATTAGAGAGACACCGCTTTTGTGG GGAAGGGCTTTAAATGCCCACTACAAAGTTAGGACTCATTGTTC AGCGCCGGTTTATATAACAGGCGAGGGGAGGCGCTGGGCTCTG ACAGCTCCGAGCCAGTTCAGCAGCCGCCGTCGCCTGCATTCCCT CCCCCTCCCCCAGGTGATGGCCCAGCCAGGGTCCGGCTGCAAA GCGACCACCCGCTGTCTCGAAGGGACCGCTCCGCCTGCCATGGT GAGTCCTTTCGGTCCTGCTTTCGGCCCCGAGTCCCCCCAACAGC ACAGGCCAGGGCTTCTGGCTCAGCCTTCCGGCTACCAACCTCTA CCCCTGCGCTGGAAAACTGCCGATAGGAGCCGCCTCTCGTTGAG CCTTGGTTTTTCTGGCCTGGAATGTGAGCTTTGGCTGCTTCCTGC ACCCAGGATGCGCTGTGTTAAAAGTTGGGGGCCGTCCCTTCTTC TCCAATAGGTCCTTTCATTCTTGTACTCCAGCCTAGGGCGCGAC ATCCCTGGCACATTTCGGTGTCAGTCGGTGCGCGAGGAAACCA GATTCAACTCTGAGTACTCGGCTAAGCGCTTCGCTGTTCCTCTCT CCCATTTCAGGCTCAGTCAGACGCAGAGGCCTTGGCAGGCGCTC TGGACAAGGACGAAGGTAGAGCCTCCCCATGTACGCCCAGCAC ACCGTCTGTCTGCTCGCCGCCCTCTGCTGCCTCTTCCGTGCCGTC TGCCGGCAAGAATATCTGCTCCAGTTGCGGTCTGGAGATCCTGG ACCGGTATCTGCTCAAGGTGAGTCAGGGTAGGTGTGCCTGCTTG CCCACGGGTGTGGTTTGCAGCCCCAAGAGCTGT | Mouse; mm10: chr2 36103286- 36104328 |
| 7 | CAAGACTTTTAAAAGTTTAGATAAATAAACAAACATTTGACGGC TTTCCATCACATCTAGACTATAATCCAAAGATCTATATGGTCCC AAACGACTTACACTTAACTACCGTCTCCCATATGGCTTCTTCCC CCATCAGTCATTGTCCTCAGCCATAGTGGCCTCCCTGTTCCTTTG GGTACAAGGGAACAACTCCCTGAGAGGTTCCATTAGCTGCTGTT GCCTGAGATGCTCTTGAGCCCACACCATCTGCTCATTTCTCTCCT CACGTGTCAGTGATTAAGAGGCTGTCCTTGGCCTCCCGTCAAAA TTACATCCCTGCCGCTTTCCACTTCTTGCCTTCTTATTTTCTAAAT AGAACTAACTCACCACTACCCAACATTCTATATAATTGGATATC TGTCCTCTGTTTAAATATAATGTTGACTTCAAGAAAGAACGTTG TCACTGCCCTGTCACCAGACTTTTAAACAGTGCCTATCGTGTGG CACATGCTCAGTGAAATTG | Mouse; mm10: chr2 36114311- 36114817 |

TABLE 1-continued

List of nucleic acid sequences disclosed herein.

| SEQ ID NO: | Nucleic Acid Sequence | Source/ Genomic Location |
|---|---|---|
| 8 | TCAACAGGGGGACACTTGGGAAAGAAGGATGGGGACAGAGCC GAGAGGACTGTTACACATTAGAGAAACATCAGTGACTGTGCCA GCTTTGGGGTAGACTGCACAAAAGCCCTGAGGCAGCACAGGCA GGATCCAGTCTGCTGGTCCCAGGAAGCTAACCGTCTCAGACAG AGCACAAAGCACCGAGACATGTGCCACAAGGCTTGTGTAGAGA GGTCAGAGGACAGCGTACAGGTCCCAGAGATCAAACTCAACCT CACCAGGCTTGGCAGCAAGCCTTTACCAACCCACCCCCACCCCA CCCACCCTGCACGCGCCCCTCTCCCCTCCCCATGGTCTCCCATG GCTATCTCACTTGGCCCTAAAATGTTTAAGGATGACACTGGCTG CTGAGTGGAAATGAGACAGCAGAAGTCAACAGTAGATTTTAGG AAAGCCAGAGAAAAAGGCTTGTGCTGTTTTTAGAAAGCCAAGG GACAAGCTAAGATAGGGCCCAAGTAAT | Mouse; mm10: chr15: 78179109- 78179610 |
| 9 | AAATAGAACTGTGAGATAGGGGGAGAGGGGGCAGGAAGGACA AGAGACCCCTGTCTCATTGTGATCCCCACCTGTCTGCTCTGTGG GAGGGTACCCATGAGGGCCAGCCCACAGCCCTTAGGTGGACAT TGTCTGGTCCTGTCTCACTGTCCCTCCCAGCAGCCCCAGAGGCC AGGAGACAGGGGTCTCAGTCCTCACTGAGAGATGTGTAAACTG AGGCCCAGTGAATGTTGAGGGCCAGGGCATGCCCTTGGTGGGA TGTGACCTGGGTCTCCTTCGCACGGGCTTCCTCCCCGAAGCCGA GCTGAGCATTTGGAGTTTGAAATGTTTCCGTACTTAGCAATCTG CTCCTCTATTCCCGGGCGGACTTCCGATAGCTCCGGCCTTATGC TGCACTAGATAAGATGGAGCAGGGAGAGGACACGGCACTACTT ATGTAACCGGCCTCTTGAAAAATGGAGCAGCGGTCAGGGCGGA ACAAGACGTCCTCTCTCTACGCATCCCTCTCCTTTCCCTGCTAAG GCTGCAGCTGGAGTCAGAGGCAGGGCTGTTCCAATCTGTCTTTG ATCAGTAACGCAGCCAGCCTCCAGCCTCCGTCAGCCTCCTCATG GCTGAGACCCGGCCTCAGTTTCCCCCACTTACATCCCGAGGATC AGAGCCTGTGAGGATGAAATGGGATAAGGTAGCTGGAACCGTC TGGCAGAGAGCGAGTCCTCAGGACTGTTGATGCCTGTGGCTGCC TGGCTTGACCCCAAGTGACCCCGCCTCCTCATCCTGCAGCAGGA GAA | Mouse; mm10: chr15: 78195347- 78196134 |
| 10 | TCTATAGAATGTGTCCCCAGCCTTGTTTTCCACACTTGATACGC AAGGAATGCATACCACAGAGAGGGATGAGGGTAGCATCCAGCC TGCTTCCTGTGTGTCGGGGCGCTACAGCCACATCTCCCCAGTCC ATCTCAGACCGTCACAGAGCTTCGCCGAATGTATAGCTTTGTTC TCTGTGCAGACAGGGAGACAGAGCCTTGGGAAGCATAGGTGCT TGCTTCTTTGCCCACTGAGTCTTAGCTGGACTTGCACACCACAT GCCTCACAGCCGGGCGCACTTGCATTTGTCACCCAGGCCCAGTG ATGATGGCTCTGCTTGCTTTGTGCTTTGTGCCAACTACAGCTCCA GCACCTGTGCCCTGGGTTTTCACTCCTTTAGTTGAACACGTAGTT ACTGGGGTTGTAGGGATGGAGCCTTTCTGCTTCCTTCTGGCAAA GTCCTTAGCGGCCTGCTGCGGGGGTGGGGGGTGTTCAGGGGAG TGGTGATGAAGTATGACAG | Mouse; mm10: chr15: 78196305- 78196806 |
| 11 | TCTCCAGTTGGAGAAACAGATGCTGTAACTGGGGCCACAGTAT AAAGAGAGCCCAGACATTGAACTGTCAACACAGAAGCCTGGCA CACTGGAACTGGCAGTCCAGCTGGGAACAAGGGGTAGAGGCTG AGGCCACTAAGTCAACTGAGGCAGGAGACATAGGAGCTAAAGC AGCTGAAGGGTGCAGGACAGCTGGGGGGTCTGAAGTGGGCCTC ATGCCCAGAGCTATGAAGTCAGGGGCTGTAGCCTAGGAGCCTT GGAAGCCAGCTGGCAAGCTGTGGCCCAAAGACGCTGACTCACC AGGAGGGGGCAGCTGGAGCCAGGCACTCCTAAGGTTTCCAGGA AGGGCAGCCTTCCAGGGCTCAGCTAGGGGAGACAGTGTTGACA GCAAGTTGTCAGGCAACTTGAGCTACTGGGCAGCTGGGAAGCT GTCCCTTGGTCCCCAGTATCATCATCACCCCAGACGCTGCCCAC CTGCCTCAGGTCCCACACAGTGATCCTCCCATCTTTAACACAAC ACATGACCAGAGAGA | Mouse; mm10: chr15: 78205234- 78205766 |
| 12 | GTCACCCTCCCCCCAAACAACCCCTTCTTCTCTGGTTCGAGAAA TTACAGGCATGAAAGATATAAATCGGGATGCTTGACTTGGGAA TATAAATCACTAAAGCTTGGGGGCAGGGGTGGGCGACCTTTGT GACCGTCCTTGTGCGTGCCAGTAAATCCTGTGGTCCAGGGGAGA AGAAAAGGCTGTGTGGCTTCTGCTCACAAAGCTGCAGAAACCA TTCTTTAAGCCCAAAAGCACTTCCAGAGAGAGCAGAGCATCCC CAGGCTGCTGGCTCAGCAAGTTCACTGTGCTCAATCTCAGGAAG TGAGGATAAGAGCAGTGCCTGGAGAGTGCCTGGTGCTGAGCTG AGGGTTTCTGAACACATTAAAGCGGGGAGCATGGACCGGGCCT CAGGAGGGGTGTTGAACATCCCTAGGCAGAGGAGTCTAGCTTC CTGGGAAAAGATATCAGGTTAAGCACACACATGTCCTCTGGAA TAAGATAATCTTTCTGATCACACACTATACACACACAAAAGCCT GCTC | Mouse; mm10: chr15: 78224841- 78225364 |

TABLE 1-continued

List of nucleic acid sequences disclosed herein.

| SEQ ID NO: | Nucleic Acid Sequence | Source/ Genomic Location |
|---|---|---|
| 13 | GCCCTCTAGGCCACCTGACCAGGTCCCCTCAGTCCCCCCCTTCC CACACTCCCACACTCAGCCCCCCTCCCCCCCCCCCGACCCCTGC AGGATTATCCTGTCTGTGTTCCTGACTCAGCCTGGGAGCCACCT GGGCAGCAGGGGCCAAGGGTGTCCTAGAAGGGACCTGGAGTCC ACGCTGGGCCAAGCCTGCCCTTTCTCCCTCTGTCTTCCGTCCCTG CTTGCGGTTCTGCTGAATGTGGTTATTTCTCTGGCTCCTTTTACA GAGAATGCTGCTGCTAATTTTATGTGGAGCTCTGAGGCAGTGTA ATTGGAAGCCAGACACCCTGTCAGCAGTGGGCTCCCGTCCTGA GCTGCCATGCTTCCTGCTCTCCTCCCGTCCCGGCTCCTCATTTCA TGCAGCCACCTGTCCCAGGGAGAGAGGAGTCACCCAGGCCCCT CAGTCCGCCCCTTAAATAAGAAAGCCTCCGTTGCTCGGCACACA TACCAAGCAGCCGCTGGTGCAATCT | Mouse; mm10: chr15: 78241348- 78241856 |
| 14 | GTGTTCTTCCCTTCCCCTTTGGACCCCCGAGACAAGCCAATAAA ATACTCGGCAGGGTGGCTTCTCTCCTTTTTTTGCCAGTAATAAA CAGACTCAGAGCAAGTTAAGGGTCTGGTCCAAGGTCATGGCTG GGATCAGTGACAGAGCCCAGAAGAGAACCTGAGACTTCTTGCT GAGCCAAGCTGGAGAGGACAGAAAGGAATGCGTCTACTCCATG CATGACCCTCTGCCAGCTTTGCTCCTTCCTAAGGGACCCATGAAC GATATGTGCACACCGCTCATACGTATGTGCACACCTGCAAGAG GAGGCATCCCATGTACACCTATGAGACGCACAGAGAAACATAT ATGTAGCCATAGGCTAGAAATTCTTTCTCTTTCTAGGTCTGCCCC TCTGCA | Mouse; mm10: chr9: 107340928- 107341325 |
| 15 | GGACCACTCAGTGTACACGGAATGTAGAATTGAGTCTGCCATTG GTCTTCCCTCAAAGTCTTGGAGGCTTGGGACTGATATTGGGAGC ATCTGGGCAGAGAAGGCCACAAAGACAGGGTGGTTTTTCTACA CTGGGACATACTCGTGAGCATGCACAGAGGCGTGTCCCCAACTT CCCTGTCACCCCTGTCCTCTGCCGGCTAGAGGGGATGCGGGGGT GGACATATGCTGCTATTGGGCAGATATCACATGTTAAGAGGTGG GGGGGGGCTCAAGAGGCGGAGGGCTAGGAGCATCCCATGGGG AGAGGTTCTGGTTTTCTTGCTGCCTCTAGCTGCTATAAATACGTT AGCACTTGAGCAACTGGAAAGCTCTGAGTAATTTAGGATGCAC AAAGCTGTAATTTAACTCCAGCATCTCAGTGTGCGAGAGCATTA AAGATGTAATTAAGATGTTTACACAAAGAGATTGGAGTCTGTG ACACTTGGGGTGCAAAACCCCAGGAAGGGACACAATGGGTGAG GTGAGGATCTGTGGGAGGCCTGGGGACAGTCACTTGGATCCCA GCTATGAGATGGCAGGCCACCCAGCTGTTTCTCCTTGGAAATGT TTTGGCCTGGGGGTTGGGGGTGGGGCATCACACTTTGATATGGA GATGGGGCAACAAAGCCTGCAATATCTGGGGGTGGAGAGGTCA AGTGGATGGAGTCTTTTGAGATCATGTCAGGAAGAGGGGCTCGA TCCCCCAAAATCATGGTGACATATGGTGTCTCGGGGTTCACAGG AGCTATGTCTAAAATACAAAGTAAA | Mouse; mm10: chr9: 107349227- 107350036 |
| 16 | TCTGCAGAAGCCTGCCATTCCACCATTTAAACCTGTGACTCCAG GCCTTAAGCCTGTTGAAGGTCGAGTCCCAGAAGGGTCATATGTG CAACTGCCTAGGGAGAGTTCCCACTCGCAGGGCCAAGAGGAGT CCCCCGGTCTGAGGTGTGGGGGCGGGGACGTGCACTGGGCGCT GGGACCACGGCTGGGGCTCAGGACTCGC | Mouse; mm10: chr9: 107399438- 107399639 |
| 17 | TGCCTCAGTTTCTTCGCCTAGAAAGCCGGGTCTAAGGGTACATG CCCTGATTCTTTTCTGGGGTGTCTCGAATTTTAAACAACACATA CTGTTCTGGGCTGATGACAAGAGGAAGTACTGGTCGGTGGCTG ATGGACATCCACCATGGTGGCAACTGGAGGGAGGGGGAACGGA CGTTGAAACCCTGCCCTCCTGGAATCTGTCGCATGCACGCACGT TGACAATGCTTGGCACTGGGGACAGGCTGGGATGGATGGAGCG GAGCGTGAGGAGGAGTGGGCATGCAGGCCCGAGTGTCTGTTTT GCTGATTGCTCCTTTTGCTTTCAAGGAGATTAAACTATTTTTAGT CCATGCCTACTGCTGGTGAGACGCTGGAGGAAGCCTTTCCATCG TTGAGATTTTCTGGAAGCTGCCAAGTGTGGTCTTCAGCTCAATT CTGGGAGCCTCCCAGAGTGGGAGGGAGGAACATTTCCATCTGG GGGCTTCGGGGACAGGCTAAGATCTTCCCTGGGGTCCTTGCTGC GCTGGCCTCCTCAAACCACGCTGCCTCGGCCTGCATAAAGCAGT AATCTGATGTGCCCGATGTTTGTAACGCTGTGTTTAAAAAAAGT AATTTATTTTCTAATTATTCCTTGTCTTGCATAACCATGCATTGC CAAAGTGTCGCTATTTAAAATATTTATCTCTCCACGCCGCAGGA GCAGCTCTGGAGCGTGGAGGGGGAAGAAATAAAAGTCCGCGTG CCAGTCGCAGGCATATTACTTTGACTCGTCCTGGTGGCTTTGAC GTCTCCCTGTAAATACATTTATTTTTCATTAGGACGTTTCTGAGC TTGTGGCCCCCGGAGAGCGGAGTGATTACGCTGTTCATCTGCAA GCGATGCAATAGAGGGGTACTCGCAGAATGACTTCCGCCCAGA GCATCCTGCGCCTGTCT | Mouse; mm10: chr9: 107443292- 107444228 |

TABLE 1-continued

List of nucleic acid sequences disclosed herein.

| SEQ ID NO: | Nucleic Acid Sequence | Source/ Genomic Location |
|---|---|---|
| 18 | TAAAATACCTTATTTTTTTCCAGTCTCTAAACTGCTAATCTCCCA GGCTAAGGGATTCTGGGACAAAGGCAAGGCCTGGAAGTGGAAA TCTGTAAAATTAGCTTCAGCGGTATTAGTGTTTGCAGTTGAAGA TTGAAAAACTGCTTTCCCAGGGCCTGATTGGAGGCTCCACTCTC CTCCAGGAAGAGGCAAGGACTCTGGGCTGGCACTGAGGACAAA TCCTGGGAGGCTGCTATGGGGCCTGGGAGCCAGGCTGCCTTGTG CTAGAGGCCTAGAGAGTGTCTGTGTCCCAAGTCCCAAGCTACCC CCAGCAGCTAACAGCTTTTCCAGTTCTCAGGCACAGCAGGTGCC AAGATCACGCTCTGGAGTCCAGCTGGGCCCCTTCCTCTTCTTTTT TTTTTTTTTTTTTAAGACCTCCTGGACACTGTTCCTCTCCCCCCC CCCGTGACCCCCCCCCTCAGTTCTCAAACACGTGAGGGTTGGGG GAGGGTTCCACAGCCAGAGAGAGGGGCCAGCTCTGGTGCCTGT GGGTACGCCCGCCCGTATGGCCCATCAGGCCTCTTGTGTGCTTG ATTGCCTCTGATTGGCTGCAGCTGAATTCAGCAAAAGCTATTAT TTGCCCTTGATGAGCCAATCAGATGGCCTCATTGGCCATTCAGA GCAGGCACCGGAACCTGAGGGTGGGGTGGGGGGTGGGGGATG GAGATGGGACTCAGTGAGGGGGTGGGAAGCTCTAAAACAGATG CAGGACCTGAGCCTGTCTGTGTCCACCACGACCTTCACACAGGT CACACCCCCTTCCCCTGACTTGTCACCCCAAACCAGGGCTTGTT GCCCAACCCCACCTCACAATTCCCTCACTCTGTAACACCTTTCC ATATACCTCTGCATGTCTAAACCCAAGACTTGCTCTATGAAATC | Mouse; mm10: chr9: 107444825- 107445746 |
| 19 | AGACCCTGCTTAGCACAGCTCTTAGCGGGTCCTTTAGGGGGTCT CCCAGCGGGCCCAGTGGGAATGAGATAAGGAAGGACACAGCTG TCCATTCTCCCGTGCCTGCTAAGGAGGAAATGGGGCCGCCTTAC ATAATTGGGGCAATTTGTTCCACTCTTGTCCTCCTGGTATCATGG CTATCACCCCCTCCTTGCTCAGGGAGTCCTTGATTGAGCGAGAA GCTCAGGCCTCCCTCTCTCCCTCCTGCTGGGGGTTGCTGAACAG AGGGTGTAGGAGCCATAGGCTCTGTCACTGCTGAGATCTGCCA GATGTCTAGGCCAGGAGAAAATGGAAAGGGCTAAGTCACAGCA TATGTGGCCACTCAGGCCTATAGCCCCAAATCTGCCTGGTAACC CATTATGTCCCCAGAGAATTTGCATGGGCGGACACCCTCATGCC GGGTCTCAGTAAGGGAAGGGGTGGGAGGCAAAAATATCCCTCC CCACCCTGAATCTCCACCCCCTCCCCCCAGAAACTGACACTTGG CCTTGTCTAAGGATGGGTTTTCCCAAAATCCTTCTGAAAAAAAC AGAATTTCAAGAGTCACTCCCTCCGGGTCTCAGCCTAGAACATA TGCAGTATCCCCTGACGTCCATAGGG | Mouse; mm10: chr9: 107452080- 107452718 |
| 20 | AAACTGGCACAGTAATGGCGGGCTGACAGACAAGGGAGTCTGT AGCACCCGCTGCCTCCGCCCACCCCTTCTCCGAGCAATTAAAAG GTGTTTATGTGGGGCTGGCAGTGGCTTCTGCCTCCCTTCCATTAC GAACATTAAGAGATCTTGACCCTTCCACTTTCCCCGCTCTTGAA AGGAGCTGCAGACACGTGGAGCCAATTAGGCGCACGCGTGGGC GCCAAGGGCCTGAGCAGCTTTTTCTCCCTGATTGCGGCGTTTAC AGCTGATTATTCTCCCCTCACCCAAACAGTGCTGCTTCCTGGCA AGGTGCCACCCAGAGGAGCCGGCTGGGGGCCCCTGGGGACAGG GGAGGACTGGATTAGTAAATGGGCATCTATCGAATGGCTTTCAT ATGTGTGGCTGGAAGGGAGAAGGGTAGGGCCAGGAATGGTGGC AGCAAGGGCCCAGGTAGCAATGAGGGTTCTTCTAACCCACCAT TTAGGGATAGCGATCAGAAAAGGGCCCTCGAGGAGGTGACCTA AATGTGTGTAGAAGCTGACGGCCACTACACACACACACACACA CACACACACACATACACAAGCATCCTTGTCCTTGGAGTCGGTCA GCATGAGCAAGAGAAAGATGTTCCCAGTGGCCATGAGAGTGGA GCCCTCCTCCCTACTTACATCCAGGTTGGATGGCCAGGAGATCC TGAGATCCTTCAAGACTCC | Mouse; mm10: chr9: 107470414- 107471129 |
| 21 | AAGCCACATCCTGGGTGGAAATATATGGCTTCAATTCCCACTCT TCCGGATGACCTCTGTGGGGAGCCCTGGCTTCACCTTGGTCCAG CTTCATCCCTTAGCCTCGCTGCCAGGAAGGCAGTGAGGTCAGAG GCTGGTGCTGGCGTG | Mouse; mm10: chr9: 107484887- 107485033 |
| 22 | CCTACCTGGTGCCCGCCAACATCTGGGGGCCATCCTGGCCAGCG CCAGCGTGGTGGTGAAGGCACTGTGCGCCGTGGTACTGTTTCTC TACCTGCTTTCCTTCGCTGTGGACACGGGCTGCCTGGCCGTCAC CCCAGGCTACCTTTTCCCACCCAACTTCTGGATCTGGACCCTGG CCACCCACGGGCTCATGGAACAGCACGTGTGGGACGTGGCCAT TAGCCTGGCCACAGTGGTTGTGGCCGGGCGATTACTGGAGCCCC TCTGGGGAGCCTTGGAGCTGCTCATCTTCTTCTC | Mouse; mm10: chr9: 107534490- 107534786 |

TABLE 1-continued

List of nucleic acid sequences disclosed herein.

| SEQ ID NO: | Nucleic Acid Sequence | Source/ Genomic Location |
|---|---|---|
| 23 | AAACGGACGGGCCTCCGCTGAACCAGTGAGGCCCCAGACGTGC GCATAAATAACCCCTGCGTGCTGCACCACCTGGGGAGAGGGGG AGGACCACGGTAAAT | Human; hg19: chr2: 171672063- 171672163 |
| 24 | GGAGCGAGCGCATAGCAAAAGGGACGCGGGGTCCTTTTCTCTG CCGGTGGCACTGGGTAGCTGTGGCCAGGTGTGGTACTTTGATGG GGCCCAGGGCTGGA | Human; hg19: chr2: 171672697- 171672797 |
| 25 | GCTCAAGGAAGCGTCGCAGGGTCACAGATCTGGGGGAACCCCG GGGAAAAGCACTGAGGCAAAACCGCCGCTCGTCTCCTACAATA TATGGGAGGGGGAGG | Human; hg19: chr2: 171672918- 171673018 |
| 26 | TTGAGTACGTTCTGGATTACTCATAAGACCTTTTTTTTTTCCTTC CGGGCGCAAAACCGTGAGCTGGATTTATAATCGCCCTATAAAG CTCCAGAGGCGGTCAGGCACCTGCAGAGGAGCCCCGCCGCTCC GCCGACTAGCTGCCCCCGCGAGCAACGGCCTCGTGATTTCCCCG CCGATCCGGTCCCCGCCTCCCCACTCTGCCCCCGCCTACCCCGG AGCCGTGCAGCCGCCTCTCCGAATCTCTCTCTTCTCCTGGCGCTC GCGTGCGAGAGGGAACTAGCGAGAACGAGGAAGCAGCTGGAG GTGACGCCGGGCAGATTACGCCTGTCAGGGCCGAGCCGAGCGG ATCGCTGGGCGCTGTGCAGAGGAAAGGCGGGAGTGCCCGGCTC GCTGTCGCAGAGCCGAGGTGGGTAAGCTAGCGACCACCTGGAC TTCCCAGCGCCCAACCGTGGCTTTTCAGCCAGGTCCTCTCCTCC CGCGGCTTCTCAACCAACCCCATCCCAGCGCCGGCCACCCAACC TCCCGAAATGAGTGCTTCCTGCCC | Human; hg19: chr2: 171673150- 171673696 |
| 27 | CAGCAGCCGAAGGCGCTACTAGGAACGGTAACCTGTTACTTTTC CAGGGGCCGTAGTCGACCCGCTGCCCGAGTTGCTGTGCGACTGC GCGCGCGGGGCTA | Human; hg19: chr2: 171673900- 171674000 |
| 28 | GAGTGCAAGGTGACTGTGGTTCTTCTCTGGCCAAGTCCGAGGGA GAACGTAAAGATATGGGCCTTTTTCCCCCTCTCACCTTGTCTCA CCAAAGTCCCTAGTCCCCGGAGCAGTTAGCCTCTTTCTTTCCAG GGAATTAGCCAGACACAACAACGGGAACCAGACACCGAACCA GACATGCCCGCCCCGTGCGCCCTCCCC | Human; hg19: chr2: 171674400- 171674600 |
| 29 | GCTCGCTGCCTTTCCTCCCTCTTGTCTCTCCAGAGCCGGATCTTC AAGGGGAGCCTCCGTGCCCCCCGGCTGCTCAGTCCCTCCGGTGTG CAGGACCCCGGAAGTCCTCCCCGCACAGCTCTCGCTTCTCTTTG CAGCCTGTTTCTGCGCCGGACCAGTCGAGGACTCTGGACAGTAG AGGCCCCGGGACGACCGAGCTG | Human; hg19: chr2: 171674903- 171675101 |
| 30 | AAACGGACGGGCCTCCGCTGAACCAGTGAGGCCCCAGACGTGC GCATAAATAACCCCTGCGTGCTGCACCACCTGGGGAGAGGGGG AGGACCACGGTAAATGGAGCGAGCGCATAGCAAAAGGGACGC GGGGTCCTTTTCTCTGCCGGTGGCACTGGGTAGCTGTGGCCAGG TGTGGTACTTTGATGGGGGCCCAGGGCTGGAGCTCAAGGAAGCG TCGCAGGGTCACAGATCTGGGGGAACCCCGGGGAAAAGCACTG AGGCAAAACCGCCGCTCGTCTCCTACAATATATGGGAGGGGGA GGTTGAGTACGTTCTGGATTACTCATAAGACCTTTTTTTTTTCCT TCCGGGCGCAAAACCGTGAGCTGGATTTATAATCGCCCTATAAA GCTCCAGAGGCGGTCAGGCACCTGCAGAGGAGCCCCGCCGCTC CGCCGACTAGCTGCCCCCGCGAGCAACGGCCTCGTGATTTCCCC GCCGATCCGGTCCCCGCCTCCCCACTCTGCCCCCGCCTACCCCG GAGCCGTGCAGCCGCCTCTCCGAATCTCTCTCTTCTCCTGGCGC TCGCGTGCGAGAGGGAACTAGCGAGAACGAGGAAGCAGCTGG AGGTGACGCCGGGCAGATTACGCCTGTCAGGGCCGAGCCGAGC GGATCGCTGGGCGCTGTGCAGAGGAAAGGCGGGAGTGCCCGGC TCGCTGTCGCAGAGCCGAGGTGGGTAAGCTAGCGACCACCTGG ACTTCCCAGCGCCCAACCGTGGCTTTTCAGCCAGGTCCTCTCCT CCCGCGGCTTCTCAACCAACCCCATCCCAGCGCCGGCCACCCAA CCTCCCGAAATGAGTGCTTCCTGCCCCAGCAGCCGAAGGCGCTA CTAGGAACGGTAACCTGTTACTTTTCCAGGGGCCGTAGTCGACC CGCTGCCCGAGTTGCTGTGCGACTGCGCGCGCGGGGCTAGAGT GCAAGGTGACTGTGGTTCTTCTCTGGCCAAGTCCGAGGGAGAA | Human |

TABLE 1-continued

List of nucleic acid sequences disclosed herein.

| SEQ ID NO: | Nucleic Acid Sequence | Source/ Genomic Location |
|---|---|---|
|  | CGTAAAGATATGGGCCTTTTTCCCCCTCTCACCTTGTCTCACCAA AGTCCCTAGTCCCCGGAGCAGTTAGCCTCTTTCTTTCCAGGGAA TTAGCCAGACACAACAACGGGAACCAGACACCGAACCAGACAT GCCCGCCCCGTGCGCCCTCCCCGCTCGCTGCCTTTCCTCCCTCTT GTCTCTCCAGAGCCGGATCTTCAAGGGGAGCCTCCGTGCCCCCG GCTGCTCAGTCCCTCCGGTGTGCAGGACCCCGGAAGTCCTCCCC GCACAGCTCTCGCTTCTCTTTGCAGCCTGTTTCTGCGCCGGACC AGTCGAGGACTCTGGACAGTAGAGGCCCCGGGACGACCGAGCT G |  |
| 31 | GGAGGAAGCCATCAACTAAACTACAATGACTGTAAGATACAAA ATTGGGAATGGTAACATATTTTGAAGTTCTGTTGACATAAAGAA TCATGATATTAATGCCCATGGAAATGAAAGGGCGATCAACACT ATGGTTTGAAAAGGGGGAAATTGTAGAGCACAGATGTGTTCGT GTGGCAGTGTGCTGTCTCTAGCAATACTCAGAGAAGAGAGAGA ACAATGAAATTCTGATTGGCCCCAGTGTGAGCCCAGATGAGGTT CAGCTGCCAACTTTCTCTTTCACATCTTATGAAAGTCATTTAAGC ACAACTAACTTTTTTTTTTTTTTTTTTTTTTTGAGACAGAGTCTTG CTCTGTTGCCCAGGACAGAGTGCAGTAGTGACTCAATCTCGGCT CACTGCAGCCTCCACCTCCTAGGCTCAAACGGTCCTCCTGCATC AGCCTCCCAAGTAGCTGGAATTACAGGAGTGGCCCACCATGCC CAGCTAATTTTTGTATTTTTAATAGATACGGGGGTTTCACCATAT CACCCAGGCTGGTCTCGAACTCCTGGCCTCAAGTGATCCACCTG CCTCGGCCTCCCAAAGTGCTGGGATTATAGGCGTCAGCCACTAT GCCCAACCCGACCAACCTTTTTTAAAATAAATATTTAAAAAATT GGTATTTCACATATATACTAGTATTTACATTTATCCACACAAAA CGGACGGGCCTCCGCTGAACCAGTGAGGCCCCAGACGTGCGCA TAAATAACCCCTGCGTGCTGCACCACCTGGGGAGAGGGGGAGG ACCACGGTAAATGGAGCGAGCGCATAGCAAAAGGGACGCGGG GTCCTTTTCTCTGCCGGTGGCACTGGGTAGCTGTGGCCAGGTGT GGTACTTTGATGGGGCCCAGGGCTGGAGCTCAAGGAAGCGTCG CAGGGTCACAGATCTGGGGGAACCCCGGGGAAAAGCACTGAGG CAAAACCGCCGCTCGTCTCCTACAATATATGGGAGGGGGAGGT TGAGTACGTTCTGGATTACTCATAAGACCTTTTTTTTTTCCTTCC GGGCGCAAAACCGTGAGCTGGATTTATAATCGCCCTATAAAGC TCCAGAGGCGGTCAGGCACCTGCAGAGGAGCCCCGCCGCTCCG CCGACTAGCTGCCCCCGCGAGCAACGGCCTCGTGATTTCCCCGC CGATCCGGTCCCCGCCTCCCCACTCTGCCCCCGCCTACCCCGGA GCCGTGCAGCCGCCTCTCCGAATCTCTCTCTTCTCCTGGCGCTCG CGTGCGAGAGGGAACTAGCGAGAACGAGGAAGCAGCTGGAGG TGACGCCGGGCAGATTACGCCTGTCAGGGCCGAGCCGAGCGGA TCGCTGGGCGCTGTGCAGAGGAAAGGCGGGAGTGCCCGGCTCG CTGTCGCAGAGCCGAGGTGGGTAAGCTAGCGACCACCTGGACT TCCCAGCGCCCAACCGTGGCTTTTCAGCCAGGTCCTCTCCTCCC GCGGCTTCTCAACCAACCCCATCCCAGCGCCGGCCACCCAACCT CCCGAAATGAGTGCTTCCTGCCCCAGCAGCCGAAGGCGCTACT AGGAACGGTAACCTGTTACTTTTCCAGGGGCCGTAGTCGACCCG CTGCCCGAGTTGCTGTGCGACTGCGCGCGCGGGGCTAGAGTGC AAGGTGACTGTGGTTCTTCTCTGGCCAAGTCCGAGGGAGAACGT AAAGATATGGGCCTTTTTCCCCCTCTCACCTTGTCTCACCAAAG TCCCTAGTCCCCGGAGCAGTTAGCCTCTTTCTTTCCAGGGAATT AGCCAGACACAACAACGGGAACCAGACACCGAACCAGACATG CCCGCCCCGTGCGCCCTCCCCGCTCGCTGCCTTTCCTCCCTCTTG TCTCTCCAGAGCCGGATCTTCAAGGGGAGCCTCCGTGCCCCCGG CTGCTCAGTCCCTCCGGTGTGCAGGACCCCGGAAGTCCTCCCCG CACAGCTCTCGCTTCTCTTTGCAGCCTGTTTCTGCGCCGGACCA GTCGAGGACTCTGGACAGTAGAGGCCCCGGGACGACCGAGCTG | Human |
| 32 | TCAACAGGGGGACACTTGGGAAAGAAGGATGGGGACAGAGCC GAGAGGACTGTTACACATTAGAGAAACATCAGTGACTGTGCCA GCTTTGGGGTAGACTGCACAAAAGCCCTGAGGCAGCACAGGCA GGATCCAGTCTGCTGGTCCCAGGAAGCTAACCGTCTCAGACAG AGCACAAAGCACCGAGACATGTGCCACAAGGCTTGTGTAGAGA GGTCAGAGGACAGCGTACAGGTCCCAGAGATCAAACTCAACCT CACCAGGCTTGGCAGCAAGCCTTTACCAACCCACCCCCACCCCA CCCACCCTGCACGCGCCCCTCTCCCCTCCCCATGGTCTCCCATG GCTATCTCACTTGGCCCTAAAATGTTTAAGGATGACACTGGCTG CTGAGTGGAAATGAGACAGCAGAAGTCAACAGTAGATTTTAGG AAAGCCAGAGAAAAAGGCTTGTGCTGTTTTTAGAAAGCCAAGG GACAAGCTAAGATAGGGCCCAAGTAATGCTAGTATTTACATTTA TCCACACAAAACGGACGGGCCTCCGCTGAACCAGTGAGGCCCC AGACGTGCGCATAAATAACCCCTGCGTGCTGCACCACCTGGGG AGAGGGGGAGGACCACGGTAAATGGAGCGAGCGCATAGCAAA AGGGACGCGGGGTCCTTTTCTCTGCCGGTGGCACTGGGTAGCTG | Human and mouse |

TABLE 1-continued

<u>List of nucleic acid sequences disclosed herein.</u>

| SEQ ID NO: | Nucleic Acid Sequence | Source/ Genomic Location |
|---|---|---|
| | TGGCCAGGTGTGGTACTTTGATGGGGCCCAGGGCTGGAGCTCA AGGAAGCGTCGCAGGGTCACAGATCTGGGGGAACCCCGGGGAA AAGCACTGAGGCAAAACCGCCGCTCGTCTCCTACAATATATGG GAGGGGGAGGTTGAGTACGTTCTGGATTACTCATAAGACCTTTT TTTTTTCCTTCCGGGCGCAAAACCGTGAGCTGGATTTATAATCG CCCTATAAAGCTCCAGAGGCGGTCAGGCACCTGCAGAGGAGCC CCGCCGCTCCGCCGACTAGCTGCCCCCGCGAGCAACGGCCTCGT GATTTCCCCGCCGATCCGGTCCCCGCCTCCCCACTCTGCCCCCG CCTACCCCGGAGCCGTGCAGCCGCCTCTCCGAATCTCTCTCTTC TCCTGGCGCTCGCGTGCGAGAGGGAACTAGCGAGAACGAGGAA GCAGCTGGAGGTGACGCCGGGCAGATTACGCCTGTCAGGGCCG AGCCGAGCGGATCGCTGGGCGCTGTGCAGAGGAAAGGCGGGA GTGCCCGGCTCGCTGTCGCAGAGCCGAGGTGGGTAAGCTAGCG ACCACCTGGACTTCCCAGCGCCCAACCGTGGCTTTTCAGCCAGG TCCTCTCCTCCCGCGGCTTCTCAACCAACCCCATCCCAGCGCCG GCCACCCAACCTCCCGAAATGAGTGCTTCCTGCCCCAGCAGCCG AAGGCGCTACTAGGAACGGTAACCTGTTACTTTTCCAGGGGCCG TAGTCGACCCGCTGCCCGAGTTGCTGTGCGACTGCGCGCGCGGG GCTAGAGTGCAAGGTGACTGTGGTTCTTCTCTGGCCAAGTCCGA GGGAGAACGTAAAGATATGGGCCTTTTTCCCCCTCTCACCTTGT CTCACCAAAGTCCCTAGTCCCCGGAGCAGTTAGCCTCTTTCTTT CCAGGGAATTAGCCAGACACAACAACGGGAACCAGACACCGA ACCAGACATGCCCGCCCCGTGCGCCCTCCCCGCTCGCTGCCTTT CCTCCCTCTTGTCTCTCCAGAGCCGGATCTTCAAGGGGAGCCTC CGTGCCCCCGGCTGCTCAGTCCCTCCGGTGTGCAGGACCCCGGA AGTCCTCCCCGCACAGCTCTCGCTTCTCTTTGCAGCCTGTTTCTG CGCCGGACCAGTCGAGGACTCTGGACAGTAGAGGCCCCGGGAC GACCGAGCTG | |
| 33 | ATTTACATTTATCCACACA | Human |
| 34 | TGCCGCTGGACTCTCTTCCAAGGAACTAGGAGAACCAAGATCC GTTTTTCTGCCAAGGGCTGCCCCCCCCACGCCCCCAACCCCCTC ACCCCGATCCCCACAGAAAGAAATCTTGAGGTAGCTGGAGCTT CTTCTGTGGGTGTGACAGGACTGCCATTCTCCTCTGTAGTCTGC AGAAGCCTGCCATTCCACCATTTAAACCTGTGACTCCAGGCCTT AAGCCTGTTGAAGGTCGAGTCCCAGAAGGGTCATATGTGCAAC TGCCTAGGGAGAGTTCCCACTCGCAGGGCCAAGAGGAGTCCCC CGGTCTGAGGTGTGGGGGCGGGGACGTGCACTGGGCGCTGGGA CCACGGCTGGGGCTCAGGACTCGCGAGCTTGGATTCGGATCGG TTTGCGCGAGCCAGTAGGGCAGGCTCCGGGGTGAACGGGGACG AGGGGCGCGCGGGCACAGGCGGGCGCGTGACCGCGGCGGGGG CGCGCGGAGGCGGGCCGGCCAAGGAGAGGGAGGGAGGGAATG AGGGAGGGAGCGACAGGGGAGGGCGGCGCCGGCAGGTTGGCG GCGGCCGCTATTTGAGCGCAGGTCCCGGGCCAGGCGCTCAAAG CGCTTGGAGCCAGCGCGGCGGGGAGATCGCTGCGCGCAGCCCG CAGAGGCGCTGCGGCCAGTGCAGCCCCGGAGGCCCCGCGCGGA GAAGGAGGTGGAGAAGAGGCCGGCTTTCCGCCCCGCCGCCCGCG CCCCCCCACCTCCATCCCGCCGCCGCCGTCCCCCCTCCCTCCCC GCGGCGCCGCATCTTGAATGGAAAC | Mouse; chr9: 107,399,268- 107,400,067 |
| 35 | GAGTAATTCATACAAAAGGACTCGCCCCTGCCTTGGGGAATCCC AGGGACCGTCGTTAAACTCCCACTAACGTAGAACCCAGAGATC GCTGCGTTCCCGCCCCCTCACCCGCCCGCTCTCGTCATCACTGA GGTGGAGAAGAGCATGCGTGAGGCTCCGGTGCCCGTCAGTGGG CAGAGCGCACATCGCCCACAGTCCCCGAGAAGTTGGGGGGAGG GGTCGGCAATTGAACCGGTGCCTAGAGAAGGTGGCGCGGGGTA AACTGGGAAAGTGATGTCGTGTACTGGCTCCGCCTTTTTCCCGA GGGTGGGGGAGAACCGTATATAAGTGCAGTAGTCGCCGTGAAC GTTCTTTTTCGCAACGGGTTTGCCGCCAGAACACAGGTAAGTGC CGTGTGTGGTTCCCGCGGGCCTGGCCTCTTTACGGGTTATGGCC CTTGCGTGCCTTGAATTACTTCCACGCCCCTGGCTGCAGTACGT GATTCTTGATCCCGAGCTTCGGGTTGGAAGTGGGTGGGAGAGTT CGAGGCCTTGCGCTTAAGGAGCCCCTTCGCCTCGTGCTTGAGTT GAGGCCTGGCTTGGGCGCTGGGGCCGCCGCGTGCGAATCTGGT GGCACCTTCGCGCCTGTCTCGCTGCTTTCGATAAGTCTCTAGCC ATTTAAAATTTTTGATGACCTGCTGCGACGCTTTTTTTTCTGGCAA GATAGTCTTGTAAATGCGGGCCAAGATCTGCACACTGGTATTTC GGTTTTTGGGGCCGCGGGCGGCGACGGGGCCCGTGCGTCCCAG CGCACATGTTCGGCGAGGCGGGGCCTGCGAGCGCGGCCACCGA GAATCGGACGGGGGTAGTCTCAAGCTGGCCGGCCTGCTCTGGT GCCTGGCCTCGCGCCGCCGTGTATCGCCCCGCCCTGGGCGGCAA GGCTGGCCCGGTCGGCACCAGTTGCGTGAGCGGAAAGATGGCC GCTTCCCGGCCCTGCTGCAGGGAGCTCAAAATGGAGGACGCGG | |

TABLE 1-continued

List of nucleic acid sequences disclosed herein.

| SEQ ID NO: | Nucleic Acid Sequence | Source/ Genomic Location |
|---|---|---|
| | CGCTCGGGAGAGCGGGCGGGTGAGTCACCCACACAAAGGAAA AGGGCCTTTCCGTCCTCAGCCGTCGCTTCATGTGACTCCACGGA GTACCGGGCGCCGTCCAGGCACCTCGATTAGTTCTCGAGCTTTT GGAGTACGTCGTCTTTAGGTTGGGGGGAGGGGTTTTATGCGATG GAGTTTCCCCACACTGAGTGGGTGGAGACTGAAGTTAGGCCAG CTTGGCACTTGATGTAATTCTCCTTGGAATTTGCCCTTTTTGAGT TTGGATCTTGGTTCATTCTCAAGCCTCAGACAGTGGTTCAAAGT TTTTTTCTTCCATTTCAGGTGTCGTGA | |

In one aspect, regulatory elements disclosed herein are cell-type selective. In some cases, regulatory elements disclosed herein are selective for PV neurons. In some cases, regulatory elements disclosed herein are selective for PV neurons in the CNS. In some cases, PV-cell selective regulatory elements or any regulatory elements disclosed herein can result in selective gene expression in PV neurons over at least one, two, three, four, five, or more non-PV CNS cell-types.

In some cases, any one or more of the regulatory elements disclosed herein are operably linked to a transgene in an expression cassette to result in selective expression in a target cell type, e.g., a PV neuron. In some cases, a regulatory element of any of the embodiments herein comprises or consists of any one of (i) SEQ ID NOS: 1-33; (ii) a variant, functional fragment, or a combination thereof; or (iii) a sequence having at least 80%, at least 85%, at least 90%, at least 91%, at least 92%, at least 93%, at least 94%, at least 95%, at least 96%, at least 97%, at least 98%, at least 99%, or 100% sequence identity to any one of (i) or (ii). In some cases, a regulatory element comprises any one of SEQ ID NOS: 1-32. In some cases, sequence identity is measured by BLAST.

In some cases, two or more, three or more, four or more, five or more, six or more, seven or more, eight or more, nine or more, or ten or more of SEQ ID NOS: 1-32, or a functional fragment or a combination thereof, or sequences having at least 80%, at least 90%, at least 95%, or at least 99% sequence identity thereto, are combined to form a larger regulatory element, or are operably linked to a gene in an expression cassette. In some cases, two or more, three or more, four or more, five or more, six or more, seven or more, eight or more, nine or more, or ten or more of SEQ ID NOS: 1-32, or a functional fragment or a combination thereof, or sequences having at least 80%, at least 90%, at least 95%, or at least 99% sequence identity thereto, are combined using a linker sequence of 1-50 nucleotides. In some cases, two or more, three or more, four or more, five or more, six or more, seven or more, eight or more, nine or more, or ten or more of SEQ ID NOS: 1-32, or a functional fragment or a combination thereof, or sequences having at least 80%, at least 90%, at least 95%, or at least 99% sequence identity thereto, are combined without a linker sequence. In some cases, a sequence of SEQ ID NO: 33 is used as a linker between any two regulatory elements. In some cases, a linker sequence between any two regulatory elements comprises SEQ ID NO: 33 or a sequence having at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 33. In some cases, sequence identity is measured by BLAST.

In some cases, when two or more regulatory elements are combined or used in an expression cassette, the regulatory elements need not be adjacent or linked in an expression cassette. For example, one regulatory element can be located upstream of a transgene, while a second regulatory element and/or additional regulatory elements can be located downstream of the transgene. In some cases, one or more regulatory elements can be located upstream of a transgene. In some cases, one or more regulatory elements can be located downstream of a transgene.

In some cases, any one or more of SEQ ID NOS: 1-22, or a functional fragment or a combination thereof, or sequences having at least 80%, at least 90%, at least 95%, or at least 99% sequence identity thereto, can be combined with any one or more of SEQ ID NO: 23-30, or a functional fragment or a combination thereof, or sequences having at least 80%, at least 90%, at least 95%, or at least 99% sequence identity thereto, to form a larger regulatory element. For example, a regulatory element comprises SEQ ID NO: 1 and SEQ ID NO: 30. A regulatory element comprises SEQ ID NO: 8 and SEQ ID NO: 30. A regulatory element comprises SEQ ID NO: 1 and SEQ ID NOS: 23-29. A regulatory element comprises SEQ ID NO: 8 and SEQ ID NOS: 23-29. In some cases, a regulatory element comprises SEQ ID NO: 30 or any one or more of SEQ ID NOS: 23-29, or a functional fragment or a combination thereof, or sequences having at least 80%, at least 90%, at least 95%, or at least 99% sequence identity thereto.

In some cases, one or more regulatory elements of the present disclosure result in selective gene expression in a PV cell. In some cases, regulatory elements that show selective activity or function in a target cell type also show minimal activity or function in one or more off-target cell types, e.g., non-PV CNS cell types, non-inhibitory neurons or excitatory neurons, non-PV cells.

In some cases, one or more regulatory elements operably linked to a gene modulates gene expression in a cell, including but not limited to, selective expression in a target cell-type over non-target cell-types. Selective expression in a target cell or cell type can also be referred to as cell-selective expression or cell-type selective expression.

Selective expression generally refers to expression in a high fraction of cells of the cell type of interest (or the target cell type) as compared to other cells (or non-target cell type). Selective expression can also be viewed as preferential expression in a target cell or target cell type over one or more non-target cells or cell-types. In some cases, selective expression of one or more regulatory elements of this disclosure is compared to CAG, EF1α, a constitutive promoter (e.g., SV40, CMV, UBC, PGK, and CBA), or a non-selective regulatory element that is known to drive expression in any cell or cell type without selectivity. In some cases, selective expression of one or more regulatory elements of this disclosure is compared to CAG, EF1α, a constitutive promoter (e.g., SV40, CMV, UBC, PGK, and CBA), a non-selective regulatory element, or an expression cassette without the regulatory elements.

Non-target cell types can include a different subset, sub-type, or type of cells as compared to the target cell or target cell type, or all non-target cell types. In some cases, one or more regulatory elements operably linked to a gene result in selective expression in a target cell type over at least one type of non-target cells, or at least two, at least three, at least four, at least five, or more than five types of non-target cells. In some cases, non-target cell types refer to all other cell types not including the target cell type. In some cases, non-target cell types are all other cell types within a relevant tissue or organ not including the target cell type, e.g., all non-target cell types in the CNS, all non-target cell types in the hippocampus. In some cases, a non-target cell or non-target cell type encompasses a subset or subtype of cells that is not the target cell. For example, non-PV CNS cell types can include GABAergic cells that express calretinin and/or somatostatin instead of parvalbumin, or all GABAergic cells that do not express parvalbumin. In some cases, cell types are distinguished by having a different cell marker, mor-phology, phenotype, genotype, function, and/or any other means for classifying cell types.

Selectivity of expression driven by a regulatory element in a cell or cell type of interest can be measured in a number of ways. Selectivity of gene expression in a target cell type over non-target cell types can be measured by comparing the number of target cells that express a detectable level of a transcript from a gene that is operably linked to one or more regulatory elements to the total number of cells that express the gene. Such measurement, detection, and quantification can be done either in vivo or in vitro.

In some instances, selectivity for PV neurons can be determined using a co-localization assay. In some cases, the co-localization assay is based on immunohistochemistry. In some cases, a detectable reporter gene is used as a transgene to allow the detection and/or measurement of gene expres-sion in a cell. In some cases, a detectable marker, e.g., a fluorescent marker or an antibody, which specifically labels the target cell is used to detect and/or measure the target cells. In some cases, a co-localization assay employs imag-ing, e.g., fluorescent imaging, to determine the overlap between different fluorescent labels, e.g., overlap between a fluorescence signal indicative of a target cell and another fluorescence signal indicative of gene expression. In some cases, fluorescent labels used for a co-localization assay include a red fluorescent protein (RFP), such as a tdTomato reporter gene, and a green fluorescent reporter protein, such as eGFP.

In some instances, a gene operably linked to one or more regulatory elements is a fluorescent protein, e.g., eGFP or RFP, wherein expression of the transgene provides a detect-able signal. In some cases, tissue is stained for eGFP or fluorescence from eGFP is detected directly using a fluo-rescence microscope. A second fluorescent marker or reporter gene having a different fluorescence or detectable signal can be used to indicate the target cells, such as an antibody that identifies the target cells. For example, an anti-PV antibody that interacts specifically with PV neurons can be used to yield a detectable signal that is distinguish-able from the fluorescence used to measure gene expression, such as a red fluorescence or a red stain. Thus, in an example wherein eGFP is a transgene operably linked to one or more regulatory elements that drive selective expression in PV neurons, and wherein the PV neurons are labeled with an anti-PV antibody, selectivity of gene expression in PV cells is measured as percentage of eGFP+ cells that are also PV+. In such assay, PV+ cells that are also eGFP+ are indicated by the overlap of both fluorescence signals, i.e., an overlap of the red and green fluorescence. Such measurement, analysis, and/or detection can be done by eye inspection or by a computer.

In some cases, one can also measure the proportion of a cell type of interest (or target cell type) that expresses a transgene as compared to the proportion of non-target cell types (or other cells) that express the transgene to assess the selectivity of one or more regulatory elements operably linked to the transgene. Similarly, selectivity of expression can also be measured by comparing the number of target cells that express a transgene operably linked to one or more regulatory elements to the total number of all cells that express the transgene. In both approaches, the higher the number of target cells that express the transgene, the more selective are the regulatory elements for the target cells. In some cases, the target cells are PV neurons.

In some cases, one or more regulatory elements disclosed herein result in increased selectivity in gene expression in a PV neuron. In some cases, one or more regulatory elements disclosed herein result in increased selectivity in gene expression in PV neurons as compared to non-PV CNS cell-types. In some cases, one or more regulatory elements disclosed herein result in increased selectivity in gene expression in PV neurons as compared to non-PV GABAer-gic cells, wherein non-PV GABAergic cells can be any one or more of GABAergic cells that express calretinin (CR), somatostatin (SOM), cholecystokinin (CCK), neuropeptide Y (NPY), vasointestinal polypeptide (VIP), choline acetyl-transferase (ChAT), or a combination thereof. In some cases, one or more regulatory elements disclosed herein result in increased selectivity in gene expression in PV neurons as compared to at least one, at least two, at least three, at least four, at least five, or more than five non-PV GABAergic subtypes. In some cases, one or more regulatory elements disclosed herein result in increased selectivity in gene expression in PV neurons as compared to all other non-PV GABAergic cells, or all other GABAergic cells that do not express PV, or all other CNS cells that do not express PV, or all other neurons that do not express PV. In some cases, one or more regulatory elements disclosed herein result in increased selectivity in gene expression in PV neurons as compared to all non-PV cells in the CNS or all non-PV neurons.

In some cases, one or more regulatory elements operably linked to a transgene result in selective expression of the transgene in PV cells, wherein the percentage of PV cells expressing the transgene is at a percentage higher than gene expression in PV cells wherein the transgene is operably linked to CAG, EF1a, a constitutive promoter (e.g., SV40, CMV, UBC, PGK, and CBA), or a non-selective regulatory element, such as SEQ ID NO: 34, or a functional fragment thereof, or a sequence having at least 80% sequence identity thereto. In some cases, one or more regulatory elements result in selective expression in PV neurons at a level that is at least 1.5 fold, at least 2 hold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, or at least 50 fold as compared to expression of a gene operably linked to CAG, EF1α, a constitutive promoter (e.g., SV40, CMV, UBC, PGK, and CBA), or a non-selective regulatory element such as SEQ ID NO: 34, or a functional fragment thereof, or a sequence having at least 80%, at least 85%, at least 90%, at least 95%, or at least 99% sequence identity thereto.

In some aspects, a regulatory element is human derived or comprises a sequence that is human derived. In some cases, a regulatory element is mouse derived or comprises a sequence that is mouse derived. In some cases, a regulatory element comprises a non-naturally occurring sequence. In some cases, a regulatory element is non-naturally occurring. In some cases, one or more human derived regulatory elements are combined with another regulatory element to generate a non-naturally occurring regulatory element. In some cases, a human derived regulatory element is combined with a mouse derived regulatory element.

The term "human derived" as used herein refers to sequences that are found in a human genome (or a human genome build), or sequences homologous thereto. A homologous sequence may be a sequence which has a region with at least 80% sequence identity (e.g., as measured by BLAST) as compared to a region of the human genome. For example, a sequence that is at least 80%, at least 85%, at least 90%, at least 91%, at least 92%, at least 93%, at least 94%, at least 95%, at least 96%, at least 97%, at least 98%, or at least 99% homologous to a human sequence is deemed human derived. In some cases, a regulatory element contains a human derived sequence and a non-human derived sequence such that overall the regulatory element has low sequence identity to the human genome, while a part of the regulatory element has 100% sequence identity (or local sequence identity) to a sequence in the human genome.

In some cases, a human-derived regulatory element is a sequence that is 100% identical to a human sequence. In some instances, the sequence of a cell-type selective regulatory element is 100% human derived.

In other instances, at least 5%, 10%, 20%, 30%, 40%, 50%, 60%, 70%, 80%, 90%, 95%, 98%, or 99% of the regulatory element sequence is human derived. For example, a regulatory element can have 50% of its sequence be human derived, and the remaining 50% be non-human derived (e.g., mouse derived or fully synthetic). For further example, a regulatory element that is regarded as 50% human derived and comprises 300 bp may have an overall 45% sequence identity to a sequence in the human genome, while base pairs 1-150 of the RE may have 90% identity (local sequence identity) to a similarly sized region of the human genome.

In some instances, a sequence that is homologous to a human derived regulatory sequence is at least 90% identical to a human sequence. In some cases, a regulatory element herein comprises a sequence that has at least 80%, at least 85%, at least 90%, at least 91%, at least 92%, at least 93%, at least 94%, at least 95%, at least 96%, at least 97%, at least 98%, or at least 99% identity to any one of SEQ ID NOS: 1, 23-31, and 33. In some cases, sequence identity is measured by BLAST. When a regulatory element comprises a sequence that is homologous (e.g., at least 80%, at least 85%, at least 90%, at least 95%, or at least 99% sequence identity) to any one or more of SEQ ID NOS: 23-29, or a functional fragment or combination thereof, such regulatory element results in higher expression of an operably linked transgene (when a promoter is also present in the expression vector or cassette), as compared to a similar vector without the regulatory element. Such higher expression of a transgene can be observed, e.g., in HEK293T or CHO cells.

In some cases, one or more regulatory elements comprise any one or more of SEQ ID NO: 23-29 combined with or used in combination with any one or more of SEQ ID NOS:

1-22 with or without a linker sequence such as SEQ ID NO: 33. In some cases, any two regulatory elements of this disclosure are linked together using a polynucleotide linker comprising 1-50 nucleotides, such as SEQ ID NO: 33 or a variant thereof. In some cases, the linker sequence is a human derived sequence. In some cases, the linker sequence is mouse derived or non-naturally occurring. In some cases, two regulatory elements are joined without a linker or without any intervening sequence. In some cases, a linker comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some cases, the linker sequence is a result of restriction enzyme site, ligation, PCR, and/or cloning.

In some cases, a human derived regulatory element is combined with a mouse derived regulatory element, such as SEQ ID NO: 32, which is a combination of SEQ ID NO: 8 (a mouse derived sequence) and SEQ ID NOS: 23-29 (human derived sequences). In some cases, cell-type selective regulatory elements are combined directly with no additional linker sequence. In other cases, cell-type selective regulatory elements are combined with one or more short linker sequences which can be either deliberate or cloning artifacts. In some cases, a linker sequence comprises 1-50 bases. For example, SEQ ID NO: 31 comprises the sequence of SEQ ID NOS: 1 and 23-29 along with an additional 19 bp of the genomic sequence (SEQ ID NO: 33) immediately following the sequence of SEQ ID NO: 1. SEQ ID NO: 32 also includes these 19 bp but without the sequence of SEQ ID NO: 1. In other examples, the combined cell-type selective regulatory elements can include short sequences, generally less than 50 bp, less than 20 bp, less than 15 bp, or less than 10 bp, from a cloning plasmid or restriction enzyme recognition site.

In some cases, regulatory elements can be derived from non-coding DNA sequences. In some cases, regulatory elements derived from non-coding DNA are associated with genes, such as upstream sequences, introns, 3' and 5' untranslated regions (UTRs), and/or downstream regions. In other cases, regulatory elements derived from non-coding DNA sequences are not associated with a gene. In some cases, regulatory elements are derived from coding sequences. In some cases, the genomic region from which a regulatory element is derived is distinct from the genomic region from which an operably linked transgene is derived. In some cases, a RE is derived from a distal genomic region or location with respect to the genomic region or location from which the transgene is derived (such as a naturally occurring or an endogenous version of the transgene).

In one aspect, a regulatory element is any non-coding sequence that modulates gene expression, e.g., selectivity of expression in a target cell. In some cases, the target cell is a PV neuron. In some cases, a regulatory element is derived from a genomic sequence upstream of a transcription initiation site, a 5' UTR sequence, an exonic sequence, an intronic sequence, or a 3' UTR sequence. In some cases, a human derived regulatory element comprises an intronic human derived sequence. In some cases, a regulatory element comprises an enhancer, and its presence in an expression cassette along with a promoter increases expression of an operably linked transgene in the target cell-type (e.g., PV neurons) compared to expression of the same transgene by the promoter without the enhancer. In some cases, an enhancer increases expression of an operably linked transgene through either a transcriptional mechanism, posttranscriptional mechanism, or both. In some cases, a regulatory element comprises an enhancer sequence, a promoter sequence, or a combination of the enhancer and promoter sequences. In some cases, a regulatory element comprises one or more of a human derived enhancer sequence, a human derived promoter sequence, a human derived intronic sequence, and/or a combination thereof.

In some cases, a regulatory element comprises one or more of SEQ ID NOS: 1-32, or a fragment or a combination thereof, or sequences having at least 80%, at least 85%, at least 90%, at least 95%, or at least 99% sequence identity thereto. In some cases, a regulatory element comprises one or more of SEQ ID NOS: 1-22, or a fragment or a combination thereof, or sequences having at least 80%, at least 85%, at least 90%, at least 95%, or at least 99% sequence identity thereto. In some cases, a regulatory element comprises one or more of SEQ ID NOS: 23-29, or a fragment or a combination thereof, or sequences having at least 80%, at least 85%, at least 90%, at least 95%, or at least 99% sequence identity thereto. In some cases, a regulatory element comprises one or more of SEQ ID NOS: 30-32, or a fragment or a combination thereof, or sequences having at least 80%, at least 85%, at least 90%, at least 95%, or at least 99% sequence identity thereto. In some cases, a regulatory element comprises a sequence of SEQ ID NOS: 30-32, or a fragment or a combination thereof, or sequences having at least 80%, at least 85%, at least 90%, at least 95%, or at least 99% sequence identity thereto.

In some instances, a regulatory element is derived from non-human DNA sequences or both human and non-human genomic sequences. In some cases, cell-type selective regulatory elements, or parts thereof, are homologous to a mammalian genomic sequence. In some cases, the regulatory elements have at least 80%, at least 85%, at least 90%, at least 91%, at least 92%, at least 93%, at least 94%, at least 95%, at least 96%, at least 97%, at least 98%, or at least 99% identity to a mammalian genomic sequence. In some cases, a regulatory element is derived from a mouse genomic sequence. In some cases, a regulatory element, or fragments thereof, has at least about 80%, 85%, 90%, 91%, 92%, 93%, 94%, 95%, 96%, 97%, 98%, 99% or more than 99% identity to a mouse genomic sequence or a non-human mammalian genomic sequence. In some cases, sequence identity is measured by BLAST. In some cases, the regulatory elements may comprise any of SEQ ID NOS: 1-33, or a fragment or a combination thereof, or sequences having at least 80%, at least 85%, at least 90%, at least 95%, or at least 99% sequence identity thereto.

In some cases, cell-type selective regulatory elements are short. In some cases, the size of the regulatory elements is compatible with the cloning capacity of a vector, e.g., a viral vector or rAAV, such that the combined size of a transgene and one or more regulatory elements does not exceed the cloning capacity of a vector. In some cases, the cell-type selective regulatory elements have a length of up to about 2050 bp, 2000 bp, 1900 bp, 1800 bp, 1700 bp, 1600 bp, 1500 bp, 1400 bp, 1300 bp, 1200 bp, 1100 bp, 1000 bp, 900 bp, 800 bp, 700 bp, 600 bp, 500 bp, 400 bp, 300 bp, 200 bp, or 100 bp. In some cases, the cell-type selective regulatory elements have a total length of no more than about 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1000 bp, 1010 bp, 1020 bp, 1030 bp, 1040 bp, 1050 bp, 1060 bp, 1070 bp, 1080 bp, 1090 bp, 1100 bp, 1200 bp, 1300 bp, 1500 bp, 1600 bp, 1700 bp, 1800 bp, 1900 bp, or 2000 bp. In some cases, the cell-type selective regulatory elements have a length of about 100 bp-1100 bp, 100 bp-1000 bp, 100 bp-900 bp, 200 bp-900 bp, 200 bp-800 bp, 300 bp-600 bp, 400 bp-800 bp, 500 bp-600 bp, or 600 bp-900 bp. In some cases, a regulatory element is between about 400-600 bp, 400-600 bp, 400-700 bp, 400-800 bp, 400-900 bp, 400-1000 bp, or 400-1500 bp. In some cases, a regulatory element is between about 500-600 bp, 500-700 bp, 500-800 bp, 500-900 bp, 500-1000 bp, or 500-1500 bp. In some cases, two or more regulatory elements are combined to form a larger cell-type selective regulatory element of 1300-2500 bp, 1300-2060 bp, about 1350 bp, about 2050 bp, or about 1880 bp.

In some cases, two or more cell-type selective regulatory elements can be combined. For example, two, three, four, five, six, seven, eight, nine, ten or more cell-type selective regulatory elements can be combined. For example, SEQ ID NO: 30 comprises sequences from seven regulatory elements, i.e., SEQ ID NOS: 23-29, all of which are derived from human genomic sequence. In some cases, cell-type selective regulatory elements refer to PV-neuron selective regulatory elements.

In some cases, a cell-type selective regulatory element is repeated two or more times to make a combined regulatory element that is also cell-type selective or has enhance cell-type selective property. In some cases, two or more regulatory elements with different cell-type selectivity are combined. In some cases, a cell-type selective regulatory element is combined with a non-selective regulatory element, e.g., a non-selective enhancer element that drives high gene expression. For example, a promoter regulatory element with high selectivity for a target cell can be combined with a regulatory element with high efficiency of expression. In some cases, one or more cell type-selective regulatory elements are combined with one or more high efficiency regulatory elements. For example, any one or more of SEQ ID NOS: 1-32, or a fragment or a combination thereof, or sequences having at least 80%, at least 85%, at least 90%, at least 95%, or at least 99% sequence identity thereto, can be combined with a constitutive promoter, such as a GAD2 promoter, a human synapsin promoter, a minCMV promoter, a TATA box, a super core promoter, or an EF1α promoter, or a combination thereof.

In some aspects, the present disclosure provides a list of regulatory elements that can be added to any gene therapy to result in selective gene expression in a target cell type, such as a PV neuron over one or more non-target cell types, such as non-PV CNS cells, including but not limited to excitatory cells and/or non-PV GABAergic cells.

In some cases, cell-type selective regulatory elements can be combined with other regulatory elements such as a high expressing promoter or a sequence that increases mRNA stability. In some cases, one or more cell-type selective regulatory elements are combined with a human, a non-human, or a non-mammalian sequence, for example a hSyn1 promoter, CBA promoter, a CMV promoter, an EF1α promoter, a polyA signal (e.g., SV40 polyA signal), or a post-transcriptional regulatory element such as woodchuck hepatitis virus post-transcriptional regulatory element (WPRE).

In some cases, the combined regulatory elements can come from different species. The combined regulatory elements can come from different genomic regions within a species. In some cases, regulatory elements are derived from distal genomic sequences, e.g., sequences that do not normally or naturally associate with each other or with a cell type of interest, are combined. In some cases, individual regulatory elements used to make a combined regulatory element can come from different human chromosomes.

In one aspect, a regulatory element of the disclosure comprises a functional fragment of any of SEQ ID NOS: 1-32, or a combination thereof, or sequences having at least 80%, at least 85%, at least 90%, at least 95%, or at least 99% sequence identity thereto. Such functional fragment can increase expression of a transgene in an expression cassette or vector when compared to a similar expression cassette or vector without the regulatory element. Such a functional fragment can function as an enhancer to increase cell-type selective expression when the fragment is operably linked to a transgene as compared to a similar vector or cassette without the functional fragment. A fragment is preferably more than 30, 40, 50, or 60 bp in length.

In some cases, a PV cell selective regulatory element or any regulatory element of this disclosure comprises any one of SEQ ID NOS: 1-32, (ii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOS: 1-32, (iii) a functional fragment of any sequence of (i) or (ii), or (iv) a combination of any sequence of (i), (ii) and/or (iii). In some cases, sequence identity is measured by BLAST. In some cases, two or more of SEQ ID NOS: 1-29, or a functional fragment or a combination thereof, or sequences having at least 80%, at least 85%, at least 90%, at least 95%, or at least 99% sequence identity thereto, are used as a regulatory element to increase transgene expression selectively in PV cells as compared to non-PV CNS cells, or to in any target cell type as compared to non-target cell type. In some cases, a functional fragment is one that results in selective expression in a target cell type over one or more non-target cell types.

In some cases, two or more copies of a regulatory element can be used to enhance selective expression in a target cell, e.g., two or more copies of any one of SEQ ID NOS: 1-29, or a fragment or a combination thereof, or sequences having at least 80%, at least 85%, at least 90%, at least 95%, or at least 99% sequence identity thereto.

In other cases, one or more of SEQ ID NOS: 1-32, or a fragment or a combination thereof, or sequences having at least 80%, at least 85%, at least 90%, at least 95%, or at least 99% sequence identity thereto, are operably linked to another regulatory element, such as a promoter or enhancer, to further increase selective expression in a target cell. In some cases, one can enhance any gene therapy by adding one or more regulatory elements as disclosed herein to improve or increase expression from the gene therapy in a target cell as compared to non-target cells. In some cases, the target cell is PV neurons or GABAergic cells that express parvalbumin.

In some aspects, one or more regulatory elements (e.g., any one or more of SEQ ID NOS: 1-32, or a fragment or a combination thereof, or sequences having at least 80%, at least 85%, at least 90%, at least 95%, or at least 99% sequence identity thereto) disclosed herein show cell-type selectivity for a target cell type over at least one, at least two, at least three, at least four, at least five, or more than five non-target cell types. In some cases, a regulatory element drives selective expression or preferential expression in a target cell subtype over at least one, at least two, at least three, at least four, at least five, or more than five non-target subtypes, or all other known subtypes of the cell. For example, GABAergic cells comprise different subtypes, including PV cells. In some cases, the target cell type is a PV cell. In some cases, one or more regulatory elements are selective for PV cells over at least one, at least two, at least three, at least four, at least five, or more than five non-target cell types. In some instances, one or more regulatory elements are selective for PV cells over all other known CNS cell-types.

In some cases, any one or more of SEQ ID NOS: 1-32, or a fragment or a combination thereof, or sequences having at least 80%, at least 85%, at least 90%, at least 95%, or at least 99% sequence identity thereto, can be combined with any one or more of SEQ ID NOS: 1-32, or a fragment or a combination thereof, or sequences having at least 80%, at least 85%, at least 90%, at least 95%, or at least 99% sequence identity thereto. In some cases, such combined regulatory elements are linked using a linker of 1-50 nucleotides. In some cases, such combined regulatory elements are not linked.

In some cases, one or more regulatory elements disclosed herein, when operably linked to any transgene (e.g., a reporter transgene or a therapeutic transgene), drives selective expression or preferential expression in at least one target cell type at a level that is statistically significantly higher than the expression driven by CAG, EF1a, a constitutive promoter (e.g., SV40, CMV, UBC, PGK, and CBA), or a non-selective regulatory element (e.g., SEQ ID NO: 34, or a fragment thereof, or a sequence having at least 80%, at least 85%, at least 90%, at least 95%, or at least 99% sequence identity thereto) when operably linked to the same transgene, or by the same construct without the regulatory elements. In some cases, statistically significantly higher means the regulatory elements drive selective expression in the target cell type at a level that is at least 1.1, 1.2, 1.3, 1.4, 1.5, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, or 100 times the expression level by CAG, EF1a, a constitutive promoter (e.g., SV40, CMV, UBC, PGK, and CBA), or a non-selective regulatory element when operably linked to the same transgene, or by the same construct without the regulatory elements. In some cases, such cell-type selective expression is assayed using a co-localization assay as described herein. In some cases, the target cell type is a parvalbumin cell. In some cases, such co-localization assay is conducted using an anti-PV antibody. In some cases, such co-localization assay is conducted using a PV-Cre mouse as disclosed herein. In some cases, the non-selective regulatory element is SEQ ID NO: 34, or a fragment thereof, or a sequence having at least 80%, at least 85%, at least 90%, at least 95%, or at least 99% sequence identity thereto.

Expression Cassettes

The terms "expression cassette" and "nucleic acid cassette" are used interchangeably to refer to a polynucleotide molecule or a nucleic acid sequence. In some cases, an expression cassette comprises one or more regulatory elements disclosed herein operably linked to a transgene. In some cases, an expression cassette comprises one or more regulatory elements. In some cases, an expression cassette comprises one or more cell type selective regulatory elements disclosed herein. In some cases, an expression cassette comprises one or more PV cell selective regulatory elements disclosed herein. In some cases, the expression cassette further comprises a promoter. In some cases, an expression cassette comprises one or more sequences of SEQ ID NOS: 1-32 and/or any combination thereof. In some cases, an expression cassette comprises one or more of SEQ ID NOS: 1-32, (ii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOS: 1-32, (iii) a functional fragment of any sequence of (i) or (ii), or (iv) a combination of any sequence of (i), (ii) and/or (iii). In some cases, sequence identity is measured by BLAST. In some cases, a regulatory element is located upstream of a transgene in an expression cassette. In some cases, a regulatory element is located downstream of a transgene in an expression cassette. In some cases, an expression cassette further comprises a promoter, e.g., a hSyn1 promoter, CBA promoter, a CMV promoter, an EF1α promoter, a polyA signal (e.g., SV40 polyA signal), or a post-transcriptional regulatory element such as woodchuck hepatitis virus post-transcriptional regulatory element (WPRE).

In some aspects, one or more regulatory elements described herein are operably linked to a transgene in an expression cassette. In some cases, a gene therapy comprises an expression cassette comprising a transgene operably linked to one or more, two or more, three or more, four or more, or five or more regulatory elements of the present disclosure to result in selective expression of the transgene in a target tissue or cell type, such as PV neurons. In some cases, an expression cassette comprises one or more PV cell selective regulatory elements or one or more regulatory elements disclosed herein operably linked to a transgene, e.g., a reporter gene, eGFP, SCN1A, SCN2A, SCN8A, SCN1B, SCN2B, KV3.1, KV3.2, KV3.3, STXBP1, a transgene encoding a DNA-binding protein, or a variant or a fragment thereof or sequences having at least 80%, at least 85%, at least 90%, at least 95%, or at least 99% sequence identity thereto.

In some cases, an expression cassette is adapted for delivery via gene therapy. In some cases, an expression cassette is a linear or a circular construct. In some cases, an expression cassette is part of a plasmid, vector, a viral vector, or rAAV.

In some cases, a gene therapy is administered directly to the CNS of a subject in need thereof or systematically via injection and/or infusion. In some cases, such subject has been diagnosed with a disease or condition associated with a haploinsufficiency or a genetic mutation, such as a haploinsufficiency or a mutation in any one of the following genes: SCN1A, SCN2A, SCN8A, SCN1B, SCN2B, KV3.1, KV3.2, KV3.3, or STXBP1. In some cases, the subject is at risk for or has Dravet syndrome, Alzheimer's disease, epilepsy, neurodegeneration, tauopathy, neuronal hypoexcitability and/or seizures. In some cases, such gene therapy is delivered using a virus or a viral vector, such as rAAV. In some cases, an AAV serotype with a tropism for CNS cells and/or ability to cross the blood brain barrier is used, such as AAV9 or a variant thereof.

In some cases, one or more regulatory elements (e.g., one or more of SEQ ID NOS: 1-32, or a fragment or a combination thereof or sequences having at least 80%, at least 85%, at least 90%, at least 95%, or at least 99% sequence identity thereto) operably linked to a transgene in an expression cassette result in selective gene expression in PV cells as compared to non-PV CNS cells, or as compared to a control element, such as a CAG, EF1a, a constitutive promoter (e.g., SV40, CMV, UBC, PGK, and CBA), or a non-selective regulatory element (e.g., SEQ ID NO: 34, or a functional fragment thereof, or a sequence having at least 80%, at least 85%, at least 90%, at least 95%, or at least 99% sequence identity thereto). In some cases, regulatory elements result in at least 50%, at least 60%, at least 70%, at least 80%, or at least 90% of all cells expressing the transgene are PV neurons. In some cases, regulatory elements result in selective gene expression in PV neurons that is about 1.5 times, 2 times, 3 times, 4 times, 5 times, 6 times, 7 times, 7.5 times, 8 times, 9 times, or 10 times higher than expected for natural distribution of PV neurons in CNS. In some cases, a regulatory element drives selective expression in PV cells, wherein the percentage of PV cells expressing the transgene is at a percentage that is at least 1.5 fold, at least 2 fold, at least 3 fold, at least 4 fold, at least 5 fold, at least 6 fold, at least 7 fold, at least 8 fold, at least 9 fold, or at least 10 fold higher than the expected distribution of PV cells in the CNS, or at least 1-5%, 5%-10%, 10-15%, 15-20%, 20-25%, 25-30%, 30-35%, 35-40%, 40-45%, 45-50%, 50-55%, 55-60%, 65-70%, 70-75%, 75-80%, 80-85%, 85-90%, or 90-95% higher than the expression in PV cells when the transgene is operably linked to CAG, EF1a, a constitutive promoter (e.g., SV40, CMV, UBC, PGK, and CBA), or a non-selective regulatory element having a sequence of SEQ ID NO: 34, or a functional fragment thereof, or a sequence having at least 80%, at least 85%, at least 90%, at least 95%, or at least 99% sequence identity thereto, and as measured in an immunohistochemical co-localization assay. In some cases, a regulatory element in an expression cassette, or use of such regulatory element in an expression cassette, results in selective gene expression in PV cells, or PV cells in the CNS, or PV neurons, wherein about 10%, 15%, 20%, 25%, 30%, 35%, 40%, 45%, 50%, 55%, 60%, 65%, 70%, 75%, 80%, 85%, 90%, or 95% of the cells expressing the transgene are PV positive.

In some cases, an expression cassette or a gene therapy comprises one or more, two or more, three or more, four or more, five or more, six or more, seven or more, eight or more, nine or more, or ten or more regulatory elements as described in TABLE 1, e.g., SEQ ID NOS: 1-32, or a functional fragment or a combination thereof, or sequences having at least 80%, at least 85%, at least 90%, at least 95%, or at least 99% sequence identity thereto.

In some cases, one or more PV cell selective regulatory elements or one or more regulatory elements disclosed herein are operably linked to any transgene in an expression cassette. In some cases, the expression cassette is a gene therapy. In some cases, the expression cassette is part of a vector or a plasmid, e.g., a viral vector or rAAV vector. In some cases, the expression cassette is part of AAV1, AAV8, AAV9, or AAVDJ or a variant or hybrid thereof. In some cases, the expression cassette comprises one or more PV cell selective regulatory elements or one or more regulatory elements disclosed herein operably linked to a transgene, wherein the transgene is SCN1A, SCN2A, SCN8A, SCN1B, SCN2B, KV3.1, KAV3.2, KV3.3, STXBP1, a gene encoding a DNA binding protein (e.g., transcriptional modulator of an endogenous gene), or a variant or a functional fragment thereof, or a sequence having at least 80%, at least 85%, at least 90%, at least 95%, or at least 99% sequence identity thereto. In some cases, such regulatory elements increase the selective expression of the transgene in PV neurons as compared to non-PV CNS cell-types. In some cases, such regulatory elements increase the expression of the transgene selectively in a target cell type, such as a PV neuron. In some cases, the target cell type is a PV cell.

Techniques contemplated herein for gene therapy of somatic cells include delivery via a viral vector (e.g., retroviral, adenoviral, AAV, helper-dependent adenoviral systems, hybrid adenoviral systems, herpes simplex, pox virus, lentivirus, and Epstein-Barr virus), and non-viral systems, such as physical systems (naked DNA, DNA bombardment, electroporation, hydrodynamic, ultrasound, and magnetofection), and chemical system (cationic lipids, different cationic polymers, and lipid polymers).

The cloning capacity of vectors or viral expression vectors is a particular challenge for expression of large transgenes. For example, AAV vectors typically have a packaging capacity of ~4.8 kb, lentiviruses typically have a capacity of ~8 kb, adenoviruses typically have a capacity of ~7.5 kb and alphaviruses typically have a capacity of ~7.5 kb. Some viruses can have larger packaging capacities, for example herpes virus can have a capacity of >30 kb and vaccinia a capacity of ~25 kb. Advantages of using AAV for gene therapy include low pathogenicity, very low frequency of integration into the host genome, and the ability to infect dividing and non-dividing cells.

To address the size constraints of certain viral vectors or to improve expression from viral vectors, the present disclosure contemplates the use of regulatory elements that are shorter than 2.5 kb, 2 kb, 1.5 kb, 1 kb, 900 bp, 800 bp, 700 bp, 600 bp, 500 bp, 400 bp, 300 bp, 200 bp, 150 bp, or 110 bp, but at least 10 bp, 50 bp or 100 bp in length. In some cases, the size of the combined regulatory element is about 2500 bp, 2000 bp, 1500 bp, 1400 bp, 1300 bp, 1200 bp, 1100 bp, or 1000 bp. In some cases, each combined regulatory element has a total length of about 100 bp, 200 bp, 300 bp, 400 bp, 500 bp, 600 bp, 700 bp, 800 bp, 900 bp, 1000 bp, 1100 bp, 1200 bp, 1300 bp, 1400 bp, 1500 bp, 1600 bp, 1700 bp, 1800 bp, 1900 bp, 2000 bp, 2100 bp, 2200 bp, 2300 bp, 2400 bp, or 2500 bp. In some cases, the size of a combined RE has a total length of about 200 bp-3000 bp, 200 bp-2500 bp, 200 bp-2100 bp, 500 bp-2500 bp, 1000 bp-2500 bp, 1500 bp-2500 bp, 1500b-2000 bp, or 2000 bp-2500 bp.

In some cases, a regulatory element of the disclosure is preferably (i) one that selectively drives expression in a cell-type of interest, such as PV cells; (ii) includes a human derived sequence, and (iii) is smaller than 2.5 kb, 2 kb, 1.5 kb, or 1 kb.

Also contemplated herein are expression cassettes, which can be a circular or linear nucleic acid molecule. In some cases, an expression cassette is delivered to cells (e.g., a plurality of different cells or cell types including target cells or cell types and/or non-target cell types) in a vector (e.g., an expression vector). A vector can be an integrating or non-integrating vector, referring to the ability of the vector to integrate the expression cassette and/or transgene into a genome of a cell. Either an integrating vector or a non-integrating vector can be used to deliver an expression cassette containing a transgene operably linked to a regulatory element. Examples of vectors include, but are not limited to, (a) non-viral vectors such as nucleic acid vectors including linear oligonucleotides and circular plasmids; artificial chromosomes such as human artificial chromosomes (HACs), yeast artificial chromosomes (YACs), and bacterial artificial chromosomes (BACs or PACs); episomal vectors; transposons (e.g., PIGGYBAC®); and (b) viral vectors such as retroviral vectors, lentiviral vectors, adenoviral vectors, and AAV vectors. Viruses have several advantages for delivery of nucleic acids, including high infectivity and/or tropism for certain target cells or tissues. In some cases, a virus is used to deliver a nucleic acid molecule or expression cassette comprising one or more regulatory elements, as described herein, operably linked to a transgene.

Preferred characteristics of viral gene therapy vectors or gene delivery vectors include the ability to be reproducible and stably propagated and purified to high titers; to mediate targeted delivery (e.g., to deliver the transgene specifically to a tissue or organ of interest without widespread vector dissemination elsewhere or off-target delivery); and to mediate gene delivery and/or transgene expression without inducing harmful side effects or off-target effects. To avoid potential harmful side effects, targeted expression or tissue/cell-type-selective expression can be achieved by placing the transgene under the control of a cell-type-selective regulatory element, e.g., one or more of SEQ ID NOS: 1-32, or a functional fragment or a combination thereof, or sequences having at least 80%, at least 85%, at least 90%, at least 95%, or at least 99% sequence identity thereto, an enhancer, promoter, stability element, UTR, or a combination thereof. For example, viral particles containing a viral vector can be designed to infect many different cell types but expression of the transgene is enhanced and/or optimized in a cell type of interest (e.g. PV neurons), and expression of the transgene is reduced and/or minimized in other non-target cell types (e.g., non-PV CNS cells). The differential expression of the transgene in different cell types can be controlled, engineered, or manipulated using different transcription factors or regulatory elements that are selective for one or more cell types. In some cases, one or more regulatory elements, such as a promoter or enhancer, or a combination thereof, are operably linked to a transgene to drive tissue- or cell-selective expression of the transgene. In some cases, one or more regulatory elements used in a gene therapy or a vector drive gene expression in a cell type selective manner, i.e., confer selective gene expression in a target cell, cell type, or tissue, and/or do not drive gene expression in one or more (e.g., at least one, two, three, or four) off-target cells or cell types. In some cases, one or more regulatory elements operably linked to a transgene enhances selective expression of the transgene in a target cell, cell type, or tissue, while the one or more regulatory elements suppress transgene expression in off-target cells, cell type, or tissue, or confers significantly lower, de minimis, or statistically lower gene expression in one or more off-target cells, cell types, or tissue.

Several serotypes of AAV, non-pathogenic parvovirus, have been engineered for the purposes of gene delivery, some of which are known to have tropism for certain tissues or cell types. Viruses used for various gene-therapy applications can be engineered to be replication-deficient or to have low toxicity and low pathogenicity in a subject or a host. Such virus-based vectors can be obtained by deleting all, or some, of the coding regions from the viral genome, and leaving intact those sequences (e.g., inverted terminal repeat sequences) that are necessary for functions such as packaging the vector genome into the virus capsid or the integration of vector nucleic acid (e.g., DNA) into the host chromatin. An expression cassette comprising a transgene, for example, can be cloned into a viral backbone such as a modified or engineered viral backbone lacking viral genes, and used in conjunction with additional vectors (e.g., packaging vectors), which can, for example, when co-transfected, produce recombinant viral vector particles. In some cases, an AAV serotype that can cross the blood brain barrier or infect cells of the CNS is preferred. In some cases, AAV9 or a variant thereof is used to deliver an expression cassette of this disclosure, comprising one or more PV selective regulatory elements operably linked to a transgene.

One advantage of delivering expression cassettes of this disclosure using gene therapy, e.g., rAAV, as described herein, is that such therapies can provide more targeted and sustained therapeutic effects over time. Additionally, viral gene therapies can be engineered to have tropism for a cell type or tissue of interest over non-target cell types or tissues. For example, viral gene therapies can be engineered to infect and deliver a payload or a therapeutic agent, e.g., a transcriptional modulator or a transgene, to one or more regions, tissues, or cell types within the CNS (e.g., PV cells), while having minimal effects on off-target tissues or cell types (e.g., non-CNS tissue or cell types, non-PV CNS cells). In some cases, viral gene therapies can be engineered to deliver a transgene across the blood brain barrier and/or target a specific region or tissue within the CNS (e.g., hippocampus) or a cell type within the CNS, e.g., PV cells.

In some cases, an AAV vector or an AAV viral particle, or virion, used to deliver one or more regulatory elements and a transgene into a cell, cell type, or tissue, in vivo or in vitro, is preferably replication-deficient. In some cases, an AAV virus is engineered or genetically modified so that it can replicate and generate virions only in the presence of helper factors.

In some cases, the expression cassette is designed for delivery by an AAV or a recombinant AAV (rAAV). In some cases, an expression cassette is delivered using a lentivirus or a lentiviral vector. In some cases, larger transgenes, i.e., genes that exceed the cloning capacity of AAV, are preferably delivered using a lentivirus or a lentiviral vector.

The AAV used in the compositions and methods described herein can be of any serotype (e.g., AAV1, AAV2, AAV5, AAV8, AAV9, and AAVDJ), including hybrid or chimeric AAV serotypes. In some cases, AAV is used to deliver and/or express a transgene operably linked to one or more regulatory elements that are selective for PV neurons as compared to non-PV CNS cells. In some cases, an AAV with a high tropism for CNS cells and/or crosses the blood brain barrier is used. In some cases, AAV1, AAV8, AAV9, and/or AAVDJ are used to deliver an expression cassette described herein.

In some cases, an expression cassette comprises one or more PV cell selective regulatory elements or one or more regulatory elements disclosed herein operably linked to a transgene that is known to be insufficiently expressed in vivo, such as in a disease or condition associated with haploinsufficiency in the gene. In some cases, the transgene is a voltage-gated ion channel (e.g., a sodium ion channel or a potassium ion channel), a neurotransmitter regulator, or a subunit or functional fragment thereof. In some aspects, the transgene encodes a DNA binding protein, an ion channel, a neurotransmitter regulator, or a subunit of the ion channel or neurotransmitter regulator. In some cases, the transgene encodes a DNA binding protein that comprises one or more zinc fingers. In some cases, the DNA binding protein comprises a domain of Cas9, a Cas family protein, nuclease-inactivated Cas9 (or dCas9), a dCas family protein, or a transcriptional activator like effector (TALE). In some cases, the transgene encodes a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA-binding domain is linked to a transcriptional modulating domain (e.g., a transcriptional activator or repressor domain). In some cases, the transgene comprises a gene editing protein, e.g., a Cas protein, Cas9.

In some aspects, the transgene is a voltage-gated ion channel or a subunit thereof, such as SCN1A, SCN2A, SCN8A, SCN1B, SCN2B, KV3.1, KV3.2, or KV3.3, or a functional fragment or variant thereof. In some cases, the transgene encodes an alpha subunit of a sodium ion channel. In some cases, the transgene encodes a beta subunit of a sodium ion channel. In some aspects, the neurotransmitter regulator is STXBP1 or a functional fragment or variant thereof.

In some aspects, an expression cassette is delivered as a viral vector, such as an AAV. In some aspects, the AAV is AAV1, AAV8, AAV9, AAV-DJ, scAAV1, scAAV8, or scAAV9. In some aspects, a gene therapy comprising an expression cassette of this disclosure is administered to a subject in need thereof (e.g., a human patient, a mammal, a transgenic animal, or an animal model). In some cases, the subject in need thereof has symptoms of, has been diagnosed with, or is at risk of developing Alzheimer's disease, Dravet syndrome, epilepsy, neurodegeneration, tauopathy, neuronal hypoexcitability, and/or seizures. In some cases, the subject in need thereof has an insufficient gene expression or a mutation in any one or more of SCN1A, SCN2A, SCN8A, SCN1B, SCN2B, KV3.1, KV3.2, KV3.3, and STXBP1.

In some cases, a gene therapy, such as rAAV9, is used to deliver an expression cassette comprising one or more PV cell selective regulatory elements or one or more regulatory elements disclosed herein operably linked a transgene, wherein the transgene is SCN1A, SCN2A, SCN8A, SCN1B, SCN2B, KV3.1, KV3.2, KV3.3, STXBP1, a gene encoding a DNA binding protein, or a functional fragment thereof, or a sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SCN1A, SCN2A, SCN8A, SCN1B, SCN2B, KV3.1, KV3.2, KV3.3, STXBP1, or a nucleic acid sequence encoding a DNA binding protein, or a functional fragment thereof. In some cases, the transgene comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a nucleic acid sequence encoding any one of SEQ ID NOS: 37-43, or a functional fragment thereof, as provided in TABLE 2 below.

In some cases, the transgene is a nucleic acid sequence encoding any one of amino acid sequences SEQ ID NOS: 36-43, or a functional fragment thereof, or nucleic acid sequences encoding amino acid sequences having at least 80%, at least 85%, at least 90%, at least 95%, or at least 99% sequence identity thereto. In some cases, one or more regulatory elements disclosed herein are operably linked to any one of nucleic acid sequences encoding amino acid sequences SEQ ID NOS: 36-43 in an expression cassette, or a functional fragment thereof, or nucleic acid sequences encoding amino acid sequences having at least 80%, at least 85%, at least 90%, at least 95%, or at least 99% sequence identity thereto.

TABLE 2

| | | List of amino acid sequences disclosed herein. |
|---|---|---|
| SEQ ID NO. | Gene | Amino Acid Sequence |
| 36 | eGFP | MVSKGEELFTGVVPILVELDGDVNGHKFSVSGEGEGDATYGKLTLKF ICTTGKLPVPWPTLVTTLTYGVQCFSRYPDHMKQHDFFKSAMPEGYV QERTIFFKDDGNYKTRAEVKFEGDTLVNRIELKGIDFKEDGNILGHKL EYNYNSHNVYIMADKQKNGIKVNFKIRHNIEDGSVQLADHYQQNTPI GDGPVLLPDNHYLSTQSALSKDPNEKRDHMVLL |

TABLE 2-continued

| | | List of amino acid sequences disclosed herein. |
|---|---|---|

| SEQ ID NO. | Gene | Amino Acid Sequence |
|---|---|---|
| 37 | SCN1B | MGTLLALVVGAALVSSAWGGCVEVDSDTEAVYGMTFKILCISCKRRS ETTAETFTEWTFRQKGTEEFVKILRYENEVLQLEEDERFEGRVVWNG SRGTKDLQDLSIFITNVTYNHSGDYECHVYRLLFFDNYEHNTSVVKKI HLEVVDKANRDMASIVSEIMMYVLIVVLTIWLVAEMVYCYKKIAAA TEAAAQENASEYLAITSESKENCTGVQVAE |
| 38 | SCN2B | MHRDAWLPRPAFSLTGLSLFFSLVPPGRSMEVTVPATLNVLNGSD ARLPCTFNSCYTVNHKQFSLNWTYQECNNCSEEMFLQFRMKIINLKL ERFQDRVEFSGNPSKYDVSVMLRNVQPEDEGIYNCYIMNPPDRHRGH GKIHLQVLMEEPPERDSTVAVIVGASVGGFLAVVILVLMVVKCVRRK KEQKLSTDDLKTEEEGKTDGEGNPDDGAK |
| 39 | SCNIA | MEQTVLVPPGPDSFNFFTRESLAAIERRIAEEKAKNPKPDKKDDDENG PKPNSDLEAGKNLPFIYGDIPPEMVSEPLEDLDPYYINKKTFIVLNKGK AIFRFSATSALYILTPFNPLRKIAIKILVHSLFSMLIMCTILTNCVFMTMS NPPDWTKNVEYTFTGIYTFESLIKIIARGFCLEDFTFLRDPWNWLDFTV ITFAYVTEFVDLGNVSALRTFRVLRALKTISVIPGLKTIVGALIQSVKK LSDVMILTVFCLSVFALIGLQLFMGNLRNKCIQWPPTNASLEEHSIEKN ITVNYNGTLINETVFEFDWKSYIQDSRYHYFLEGFLDALLCGNSSDAG QCPEGYMCVKAGRNPNYGYTSFDTFSWAFLSLFRLMTQDFWENLYQ LTLRAAGKTYMIFFVLVIFLGSFYLINLILAVVAMAYEEQNQATLEEA EQKEAEFQQMIEQLKKQQEAAQQAATATASEHSREPSAAGRLSDSSS EASKLSSKSAKERRNRRKKRKQKEQSGGEEKDEDEFQKSESEDSIRRK GFRFSIEGNRLTYEKRYSSPHQSLLSIRGSLFSPRRNSRTSLFSFRGRAK DVGSENDFADDEHSTFEDNESRRDSLFVPRRHGERRNSNLSQTSRSSR MLAVFPANGKMHSTVDCNGVVSLVGGPSVPTSPVGQLLPEVIIDKPA TDDNGTTTETEMRKRRSSSFHVSMDFLEDPSQRQRAMSIASILTNTVE ELEESRQKCPPCWYKFSNIFLIWDCSPYWLKVKHVVNLVVMDPFVDL AITICIVLNTLFMAMEHYPMTDHFNNVLTVGNLVFTGIFTAEMFLKIIA MDPYYFQEGWNIFDGFIVTLSLVELGLANVEGLSVLRSFRLLRVFKL AKSWPTLNMLIKIIGNSVGALGNLTLVLAIIVFIFAVVGMQLFGKSYK DCVCKIASDCQLPRWHMNDFFHSFLIVFRVLCGEWIETMWDCMEVA GQAMCLTVFMMVMVIGNLVVLNLFLALLLSSFSADNLAATDDDNEM NNLQIAVDRMHKGVAYVKRKIYEFIQQSFIRKQKILDEIKPLDDLNNK KDSCMSNHTAEIGKDLDYLKDVNGTTSGIGTGSSVEKYIIDESDYMSF INNPSLTVTVPIAVGESDFENLNTEDFSSESDLEESKEKLNESSSSSEGS TVDIGAPVEEQPVVEPEETLEPEACFTEGCVQRFKCCQINVEEGRGKQ WWNLRRTCFRIVEHNWFETFIVFMILLSSGALAFEDIYIDQRKTIKTML EYADKVFTYIFILEMLLKWVAYGYQTYFTNAWCWLDFLIVDVSLVSL TANALGYSELGAIKSLRTLRALRPLRALSRFEGMRVVVNALLGAIPSI MNVLLVCLIFWLIFSIMGVNLFAGKFYHCINTTTGDRFDIEDVNNHTD CLKLIERNETARWKNVKVNFDNVGFGYLSLLQVATFKGWMDIMYA AVDSRNVELQPKYEESLYMYLYFVIFIIFGSFFTLNLFIGVIIDNFNQQK KKFGGQDIFMTEEQKKYYNAMKKLGSKKPQKPIPRPGNKFQGMVFD FVTRQVFDISIMILICLNMVTMMVETDDQSEYVTTILSRINLVFIVLFTG ECVLKLISLRHYYFTIGWNIFDFVVVILSIVGMFLAELIEKYFVSPTLFR VIRLARIGRILRLIKGAKGIRTLLFALMMSLPALFNIGLLLFLVMFIYAIF GMSNFAYVKREVGIDDMFNFETFGNSMICLFQITTSAGWDGLLAPILN SKPPDCDPNKVNPGSSVKGDCGNPSVGIFFFVSYIIISFLVVVNMYIAVI LENFSVATEESAEPLSEDDFEMFYEVWEKFDPDATQFMEFEKLSQFA AALEPPLNLPQPNKLQLIAMDLPMVSGDRIHCLDILFAFTKRVLGESG EMDALRIQMEERFMASNPSKVSYQPITTTLKRKQEEVSAVIIQRAYRR HLLKRTVKQASFTYNKNKIKGGANLLIKEDMIIDRINENSITEKTDLTM STAACPPSYDRVTKPIVEKHEQEGKDEKAKGK |
| 40 | STXBP1 | MAPIGLKAVVGEKIMHDVIKKVKKKGEWKVLVVDQLSMRMLSSCC KMTDIMTEGITIVEDINKRREPLPSLEAVYLITPSEKSVHSLISDFKDPPT AKYRAAHVFFTDSCPDALFNELVKSRAAKVIKTLTEINIAFLPYESQV YSLDSADSFQSFYSPHKAQMKNPILERLAEQIATLCATLKEYPAVRYR GEYKDNALLAQLIQDKLDAYKADDPTMGEGPDKARSQLLILDRGFDP SSPVLHELTFQAMSYDLLPIENDVYKYETSGIGEARVKEVLLDEDDDL WIALRHKHIAEVSQEVTRSLKDFSSSKRMNTGEKTTMRDLSQMLKK MPQYQKELSKYSTHLHLAEDCMKHYQGTVDKLCRVEQDLAMGTDA EGEKIKDPMRAIVPILLDANVSTYDKIRIILLYIFLKNGITEENLNKLIQH AQIPPEDSEIITNMAHLGVPIVTDSTLRRRSKPERKERISEQTYQLSRWT PIIKDIMEDTIEDKLDTKHYPYISTRSSASFSTTAVSARYGHWHKNKAP GEYRSGPRLIIFILGGVSLNEMRCAYEVTQANGKWEVLIGSTHILTPTK FLMDLRHPDFRESSRVSFEDQAPTME |
| 41 | Kv3.1 | MGQGDESERIVINVGGTRHQTYRSTLRTLPGTRLAWLAEPDAHSHFD YDPRADEFFFDRHPGVFAHILNYYRTGKLHCPADVCGPLYEEELAFW GIDETDVEPCCWMTYRQHRDAEEEALDSFGGAPLDNSADDADADGPG DSGDGEDELEMTKRLALSDSPDGRPGGFWRRWQPRIWALFEDPYSSR |

TABLE 2-continued

List of amino acid sequences disclosed herein.

| SEQ ID NO. | Gene | Amino Acid Sequence |
|---|---|---|
| | | YARYVAFASLFFILVSITTFCLETHERFNPIVNKTEIENVRNGTQVRYY<br>REAETEAFLTYIEGVCVVWFTFEFLMRVIFCPNKVEFIKNSLNIIDFVAI<br>LPFYLEVGLSGLSSKAAKDVLGFLRVVRFVRILRIFKLTRHFVGLRVL<br>GHTLRASTNEFLLLIIFLALGVLIFATMIYYAERIGAQPNDPSASEHTHF<br>KNIPIGFWWAVVTMTTLGYGDMYPQTWSGMLVGALCALAGVLTIA<br>MPVPVIVNNFGMYYSLAMAKQKLPKKKKKHIPRPPQLGSPNYCKSV<br>VNSPHHSTQSDTCPLAQEEILEINRAGRKPLRGMSI |
| 42 | Kv3.2 | MGKIESNERVILNVGGTRHETYRSTLKTLPGTRLALLASSEPQGDCLT<br>AAGDKLQPLPPPLSPPPRPPPLSPVPSGCFEGGAGNCSSHGGNGGNGG<br>SDHPGGGREFFFDRHPGVFAYVLNYYRTGKLHCPADVCGPLFEEELA<br>FWGIDETDVEPCCWMTYRQHRDAEEALDIFETPDLIGGDPGDDEDLA<br>AKRLGIEDAAGLGGPDGKSGRWRKLQPRMWALFEDPYSSRAARFIAF<br>ASLFFILVSITTFCLETHEAFNIVKNKTEPVINGTSPVLQYEIETDPALTY<br>VEGVCVVWFTFEFLVRIVFSPNKLEFIKNLLNIIDFVAILPFYLEVGLSG<br>LSSKAAKDVLGFLRVVRFVRILRIFKLTRHFVGLRVLGHTLRASTNEF<br>LLLIIFLALGVLIFATMIYYAERVGAQPNDPSASEHTQFKNIPIGFWWA<br>VVTMTTLGYGDMYPQTWSGMLVGALCALAGVLTIAMPVPVIVNNFG<br>MYYSLAMAKQKLPRKRKKHIPPAPLASSPTFCKTELNMACNSTQSDT<br>CLGKENRLLEHNRSVLSGDDSTGSEPPLSPPERLPIRRSSTRDKNRRGE<br>TCFLLTTGDYTCASDGGIRKASTLEPMESTAQTKGDTRPEAHWNCAH<br>LLNFGCPTGSSFPTL |
| 43 | Kv3.3 | MLSSVCVSSFRGRQGASKQQPAPPPQPPESPPPPPLPPQQQQPAQPGPA<br>ASPAGPPAPRGPGDRRAEPCPGLPAAAMGRHGGGGGDSGKIVINVGG<br>VRHETYRSTLRTLPGTRLAGLTEPEAAARFDYDPGADEFFFDRHPGVF<br>AYVLNYYRTGKLHCPADVCGPLFEEELGFWGIDETDVEACCWMTYR<br>QHRDAEEALDSFEAPDPAGAANAANAAGAHDGGLDDEAGAGGGGL<br>DGAGGELKRLCFQDAGGGAGGPPGGAGGAGGTWWRRWQPRVWAL<br>FEDPYSSRAARYVAFASLFFILISITTFCLETHEGFIHISNKTVTQASPIP<br>GAPPENITNVEVETEPPLTYVEGVCVVWFTFEFLMRITFCPDKVEFLKS<br>SLNIIDCVAILPFYLEVGLSGLSSKAAKDVLGFLRVVRFVRILRIFKLTR<br>HFVGLRVLGHTLRASTNEFLLLIIFLALGVLIFATMIYYAERIGADPDDI<br>LGSNHTYFKNIPIGFWWAVVTMTTLGYGDMYPKTWSGMLVGALCA<br>LAGVLTIAMPVPVIVNNFGMYYSLAMAKQKLPKKKNKHIPRPPQPGS<br>PNYCKPDPPPPPPPHPHHGSGGISPPPPITPPSMGVTVAGAYPAGPHTH<br>PGLLRGGAGGLGIMGLPPLPAPGEPCPLAQEEVIEINRADPRPNGDPA<br>AAALAHEDCPAIDQPAMSPEDKSPITPGSRGRYSRDRACFLLTDYAPS<br>PDGSIRKATGAPPLPPQDWRKPGPPSFLPDLNANAAAWISP |

In some cases, the one or more PV cell selective regulatory elements comprise sequences of SEQ ID NOS: 1-32, a functional fragment or a combination thereof, or sequences comprising at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity thereto. In some cases, sequence identity is measured by BLAST. In some cases, such gene therapy is used to treat epilepsies, neurodegeneration, tauopathy, neuronal hypoexcitability, Dravet syndrome and/or Alzheimer's disease. In some cases, such gene therapy is used to treat epilepsy and/or seizures associated with Dravet syndrome and/or Alzheimer's disease. In some cases, treatment using a gene therapy described herein results in reduced seizure frequency and/or duration. In some cases, treatment using a gene therapy described herein results in increased formation of functional sodium ion channels, functional potassium ion channels, or functional neurotransmitter regulatory in vivo.

In some cases, AAV serotypes 1, 8, and/or 9, or a hybrid thereof can be used with an expression cassette described herein to target selective expression in PV cells. In some cases, an expression cassette designed for delivery by an AAV comprises a 5' ITR, one or more cell-type selective regulatory elements, an optional enhancer, an optional minimal promoter, a transgene, optionally one or more intron(s), an optional polyA signal, and a 3' ITR. In some instances, an expression cassette can contain a 5' ITR, two cell-type selective REs, a basal promoter, a transgene, one or more post-transcriptional RNA regulatory element(s), and a 3' ITR.

Figure 7:
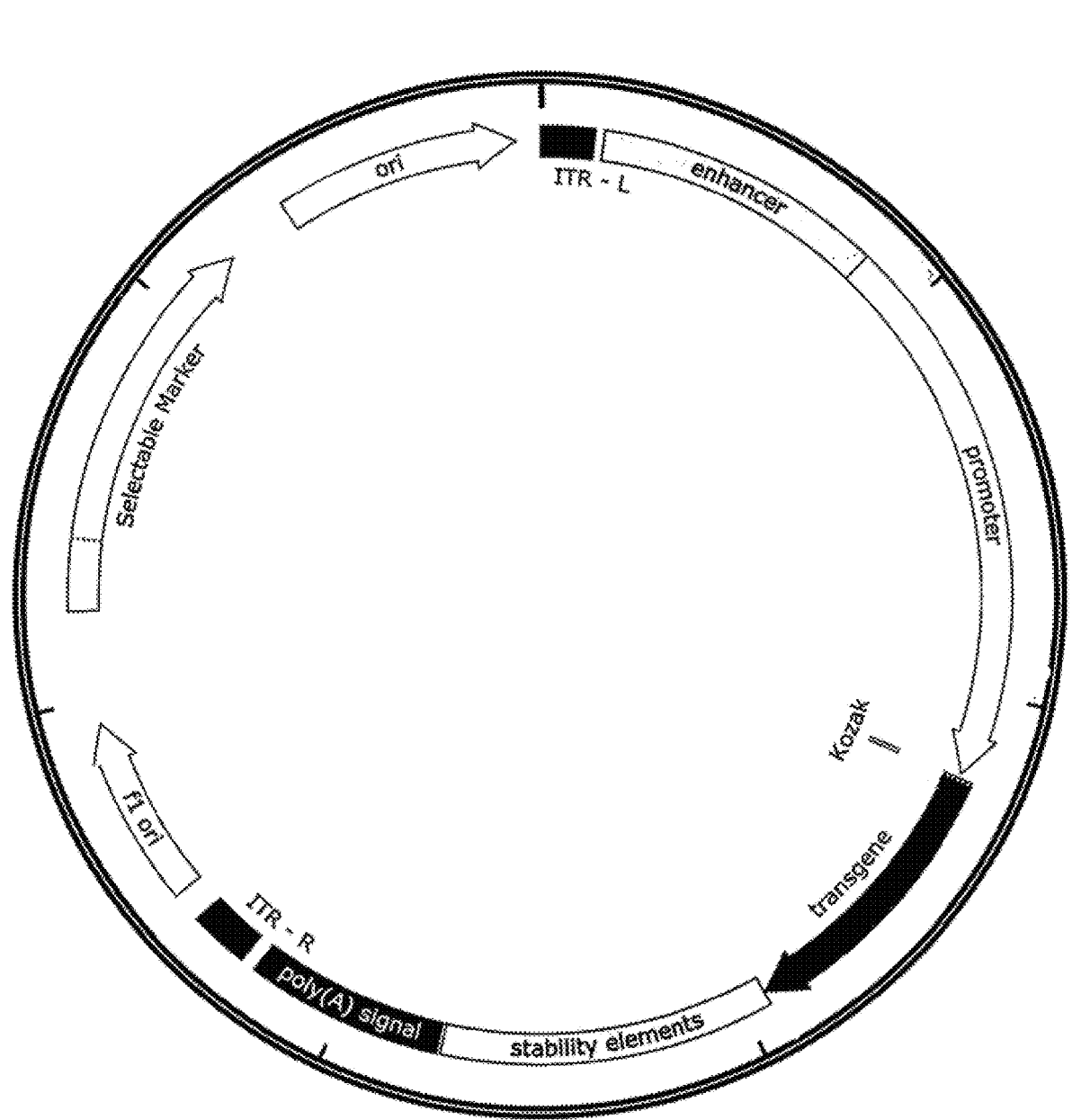
FIG. 7 illustrates a schematic of an example of an expression cassette containing REs of this disclosure, e.g., an enhancer, a promoter, and stability elements. REs can be located upstream and/or downstream of a transgene in an expression cassette, which can be a plasmid, vector, or a viral vector.

An exemplary AAV expression cassette is illustrated in FIG. 7. In some cases, the expression cassette contains a 5' AAV ITR, an enhancer (e.g., PV cell selective enhancer or one or more combined regulatory elements), a promoter (e.g., one or more PV cell selective promoters or regulatory elements), a transgene (e.g., SCN1A, SCN2A, SCN8A, SCN1B, SCN2B, KV3.1, KV3.2, KV3.3, STXBP1, or a gene encoding a DNA binding protein), a post-transcriptional regulatory element, and a 3' AAV ITR. The promoter can be PV cell selective, or a constitutive promoter. In some cases, the transgene is a reporter gene, e.g., a coding sequence for eGFP, RFP, or a fluorescent marker. In other cases, the transgene encodes a DNA binding protein that modulates gene expression.

In some cases, the transgene is a therapeutic transgene, e.g., a coding sequence for SCN1A, SCN2A, SCN8A, SCN1B, SCN2B, KV3.1, KV3.2, KV3.3, STXBP1, or a DNA binding protein, or a functional fragment or a sequence having at least 80%, at least 85%, at least 90%, at least 95%, or at least 99% sequence identity thereto. The post-transcriptional regulatory element can be any sequence which influences the expression of a protein from an mRNA or stability of an RNA, for example, an intron, an internal ribosome entry site (IRES), or a woodchuck hepatitis virus post-transcriptional regulatory element. In some cases, the post-transcriptional regulatory element is a combination of two or more post-transcriptional regulatory elements.

The expression cassette can be designed for delivery by an optimized therapeutic retroviral vector, e.g., a lentiviral vector. The retroviral vector can be a lentiviral vector comprising a left (5') LTR; sequences which aid packaging and/or nuclear import of the virus, at least one cell-type selective regulatory element, optionally a lentiviral reverse response element (RRE); optionally a promoter or active portion thereof; a transgene operably linked to one or more regulatory elements; optionally an insulator; and a right (3') retroviral LTR.

In some cases, the expression cassette comprises one or more cell-type selective regulatory elements disclosed herein. In some cases, the expression cassette comprises two or more regulatory elements combined. In some examples, the expression cassette comprises two or more regulatory elements that are not combined, for example, a promoter upstream of the transgene and an enhancer or stability element located downstream of the transgene.

In some cases, the expression cassette contains a putative cell-type selective regulatory element that has selective activity in a cell type of interest, for example, a putative PV cell selective regulatory element. The expression cassette containing the putative regulatory element can be packaged in a viral vector and transfected into an animal model to assess the activity of the putative cell-type selective regulatory element. In some cases, a putative cell type selective regulatory element can be assessed in vitro or ex vivo by delivering a vector containing the putative cell type selective regulatory element into a plurality of cells or cell types that include a target cell or cell type, and then comparing the cell type selective activity of the putative regulatory element to a control regulatory element, such as a constitutive promoter or regulatory element, or a previously known regulatory element.

In some cases, selective expression is used to selectively express a therapeutic moiety or a transgene in a cell-type of interest (or tissue-type of interest), such as PV neurons in the CNS. In some cases, a vector comprising a cell-type selective regulatory element operably linked to a transgene results in an increased selective expression of the transgene in the cell-type of interest as compared to one or more (e.g., at least two, three, four, or five) other cells, cell types, tissues, or tissue types, or results in a preferred expression of the transgene in the cell-type of interest as compared to one or more cells or cell types, e.g., at least one, two, three, four, or five non-target cell types.

Any known technique can be used to deliver the regulatory elements and a transgene, or compositions comprising regulatory elements and a transgene, to cells of interest (or a target cell or cell type) to confer or induce in vitro, in vivo, or ex vivo expression of the transgene in a cell-type selective manner.

The expression cassettes containing cell-type selective regulatory elements of this disclosure further comprise one or more transgenes. The transgenes can be protein-coding genes. In some cases, the expression cassette contains a transgene. The transgene can replace an absent or defective gene, or compensate for deficient expression of a protein inside a cell. The transgene can be involved in a cell signaling pathway. In some cases, a transgene can encode a wild-type protein, a functional fragment thereof, a variant or mutant protein having enhanced therapeutic properties, e.g., enhanced activity. In some cases, the transgene can encode a DNA binding protein comprising one or zinc finger or a domain of dCas9, an ion channel, such as a potassium ion channel or a sodium ion channel, or a subunit thereof, a neurotransmitter factor or a neurotransmitter regulator. In some cases, a transgene can encode an ion channel subunit, a variant, or a mutant thereof. In some cases, the transgene encodes a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene comprises a gene editing protein, e.g., a Cas protein, Cas9.

The regulatory elements disclosed herein can be located at any position within an expression vector or cassette. For example, the regulatory elements can be positioned upstream of an enhancer, downstream of an enhancer but upstream of a promoter, within the 5' UTR of a transgene, within an intron in the transgene, in the 3' UTR of the transgene, or downstream of the transgene. In some cases, one or more regulatory elements are positioned upstream or downstream of the operably linked transgene.

In some examples, a regulatory element of this disclosure results in selective expression of an operably linked transgene at a level that is at least 0.5, 1.0, 1.1, 1.2, 1.3, 1.4, 1.5, 1.6, 1.7, 1.8, 1.9, 2.0, 2.5, or 3 IU/ml in a target cell type (e.g., PV cells) as measured by ELISA. In some cases, a regulatory element's ability to increase transgene expression can be assessed in a mouse wherein the total amount of transgene expression in the whole mouse and/or the total number of cell types or tissue types having transgene expression are measured.

When assessing the activity of an expression cassette or vector, the activity or expression can be represented as an activity or expression level per unit dose, or normalized to a dose of expression cassette or vector administered or delivered to a cell, mouse, or a subject. In some cases, expression or activity of a transgene is normalized to an amount of plasmid or DNA (e.g., $\mu g/kg$ per mouse), or viral particles (e.g., normalized to an amount of genome copies/kg per mouse or subject) used to allow comparison across different expression vectors or cassettes with or without a regulatory element. For example, when assessing a regulatory element's activity in a mouse, selective expression or activity in PV cells assayed can be normalized to a dose of about 5, 6, 7, 8, 9, 10, 11, 12, 13, 14, 15, 16, 17, 18, 19, 20, or greater than 10 or 720 $\mu g$ of expression vector, cassette, or plasmid per mouse. In some cases, the expression level or activity can be normalized to $10^{10}$, $10^{11}$, $10^{12}$, $10^{13}$, $10^{14}$, or $10^{15}$ gc/kg of viral particles containing an expression vector or cassette as disclosed herein per mouse.

In some aspects, an expression cassette comprises one or more regulatory elements (e.g., any one or more of SEQ ID NOS: 1-32, or a functional fragment or a combination thereof, or sequences having at least 80%, at least 85%, at least 90%, at least 95%, or at least 99% sequence identity thereto) disclosed herein operably linked to a transgene to result in cell-type selective expression, or preferential expression, of the transgene in a target cell type over at least one, at least two, at least three, at least four, at least five, or more than five non-target cell types. In some cases, an expression cassette comprises one or more regulatory elements operably linked to a transgene to result in cell-type selective expression or preferential expression in a target cell subtype over at least one, at least two, at least three, at least four, at least five, or more than five non-target subtypes, or all other known subtypes of the cell. In some cases, the transgene is any one of SCN1A, SCN2A, SCN8A, SCN1B, SCN2B, KV3.1, KV3.3, and STXBP1, or a functional fragment thereof, or sequences having at least 80%, at least 85%, at least 90%, at least 95%, or at least 99% sequence identity thereto. In some cases the transgene encodes a DNA binding protein that modulates an endogenous gene (e.g., an endogenous SCN1A, SCN2A, SCN8A, SCN1B, SCN2B, KV3.1, KV3.2, KV3.3, or STXBP1). In some cases, the transgene encodes any one of SEQ ID NOS: 36-43, or a functional fragment thereof, or sequences having at least 80%, at least 85%, at least 90%, at least 95%, or at least 99% sequence identity thereto. In some cases, the transgene encodes a transcriptional modulator. In some cases, the transgene encodes a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene is a gene editing protein, such as a Cas family protein, Cas9, a zinc finger nuclease, a zinc finger nuclease, or a transcription activator-like effector nuclease. In some cases, the transgene is a reporter gene or a fluorescent marker. In some cases, an expression cassette disclosed herein is in a viral vector. In some cases, an expression cassette disclosed herein is packaged in an rAAV, such as rAAV9 or rAAVDJ. In some cases, an expression cassette disclosed herein is delivered into a cell as a gene therapy. In some cases, a gene therapy disclosed herein is delivered into a subject, preferably a human or a mammal. In some cases, an expression cassette disclosed herein is used to treat a neurological condition or disease, such as epilepsy, a neurodegenerative disease, tauopathy, neuronal hypoexcitability, Dravet syndrome or Alzheimer's disease.

In some cases, an expression cassette (e.g., gene therapy, viral vector, vector, or plasmid) comprises any one or more of SEQ ID NOS: 1-32, or a functional fragment or a combination thereof, or sequences having at least 80%, at least 85%, at least 90%, at least 95%, or at least 99% sequence identity thereto, operably linked to a transgene. In some cases, such combined regulatory elements are linked using a linker of 1-50 nucleotides. In some cases, such combined regulatory elements are not linked. In some cases, two or more regulatory elements are located upstream and/or downstream of the promoter. In some cases, two or more regulatory elements are located upstream and/or downstream of the transgene.

In some cases, an expression cassette comprises one or more regulatory elements disclosed herein, when operably linked to any transgene (e.g., a reporter transgene or a therapeutic transgene), drives selective expression or preferential expression in at least one target cell type at a level that is statistically significantly higher than the expression driven by CAG, EF1α, a constitutive promoter, or a non-selective regulatory element when operably linked to the same transgene, or by the same construct without the regulatory elements. In some cases, statistically significantly higher means the regulatory elements drive selective expression in the target cell type at a level that is at least 1.1, 1.2, 1.3, 1.4, 1.5, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, or 100 times the expression level by CAG, EF1α, a constitutive promoter, or a non-selective regulatory element when operably linked to the same transgene in the target cell type, or by the same construct without the regulatory elements. In some cases, such cell-type selective expression is assayed using a co-localization assay as described herein.

In other aspects, an expression cassette comprising one or more regulatory elements disclosed herein operably linked to any transgene disclosed herein results in selective expression or preferential expression of the transgene in a target cell type over at least one, at least two, at least three, at least four, at least five, or more than five non-target cell types or non-target subtypes.

In some instances, the target cell type is a PV cell. In some cases, the non-target cell subtypes are at least one, at least two, at least three, or at least four of the non-PV GABAergic subtypes disclosed herein. In some cases, an expression cassette comprising a regulatory element disclosed herein is selective for PV cells over all non-PV GABAergic cells or all non-PV CNS cells. In some cases, cell-type selectivity is measured according to a co-localization assay disclosed herein. In some cases, cell-type selectivity is measured using a mouse that expresses Cre in the target cell type.

Parvalbumin (PV) Neurons

GABAergic neurons produce gamma aminobutyric acid (GABA), the main inhibitory neurotransmitter in the CNS. GABA is important for reducing neural excitability throughout the nervous system. GABA acts at inhibitory synapses by binding specific transmembrane receptors and causing the opening of ion channels which negatively change the membrane polarization. This generally results in hyperpolarization of the cell and increases the signal required to trigger an action potential. Defects in GABAergic neurons can result in an imbalance between excitatory and inhibitory signaling, and have been implicated in many neurological diseases, including Dravet syndrome, epilepsy, neurodegeneration, tauopathies and Alzheimer's disease. Other neurological conditions or diseases implicated include a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., chronic traumatic encephalopathy, generalized epilepsy with febrile seizures plus (GEFS+), epileptic encephalopathy, temporal lobe epilepsy, focal epilepsy, tuberous sclerosis); and/or neurodegeneration (e.g., Alzheimer's disease, Parkinson's disease). In some cases, the neurological condition or disease is any seizure and/or epilepsy related condition or disease wherein PV neurons are implicated.

Parvalbumin is a calcium-binding protein, which is expressed in about 40% of total GABAergic interneurons in the somatosensory cortex. Within the CNS, PV cells are generally considered GABAergic cells. Various studies have also identified GABAergic cells to include distinct subtypes of cells, including cells that express PV, SOM, CR, CCK, NPY, VIP, or a combination thereof.

PV neurons are particularly relevant for various neurological diseases or conditions, such as Dravet syndrome, Alzheimer's disease, epilepsy, neurodegeneration, tauopathies and/or seizures. In some cases, a PV-neuron-associated neurological condition or disease is a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, the neurological condition or disease is any seizure and/or epilepsy related condition or disease wherein PV neurons are implicated. In various aspects, the target cell is PV cells in the CNS, or GABAergic cells that express PV.

In various aspects, PV-expressing interneurons are also called basket cells, which can be further subdivided by size of the cell body (e.g., large basket cell, small basket cell, and nest basket cell), and dendritic and axonal projection. Physiologically, PV-expressing basket cells are often fast-spiking (FS), characterized by a high-frequency train of action potentials (APs) with little adaptation. It is widely accepted that PV basket neurons innervate the soma and proximal dendrites of excitatory pyramidal neurons. Feedforward inhibition mediated through FS PV-expressing basket neurons can be found in several cortical networks including thalamocortical, translaminar, and interareal circuits. FS PV basket neurons strongly inhibit neighboring excitatory pyramidal neurons. It has been shown that PV basket neurons and pyramidal neurons that share common excitatory inputs tend to be reciprocally connected (feedback inhibition). These connections can serve to regulate the precise time window in which the excitatory neurons can generate spikes in response to excitatory drives. In addition, thalamocortical and intracortical excitatory inputs onto FS PV basket neurons are depressed by high frequency stimulation, which mediates activity-dependent feedforward inhibition. PV-expressing basket cells also innervate other interneurons including other basket cells and are electrically coupled with each other through gap junctions. It has been proposed that this feature may help to generate and maintain cortical network synchronization and oscillation.

In some cases, one or more regulatory elements disclosed herein result in increased selectivity in gene expression in PV neurons as compared to at least one, at least two, at least three, at least four, or at least five non-PV expressing neurons. In some cases, non-PV cells include all non-PV GABAergic cells. In some cases, non-PV GABAergic neurons include, but are not limited to, calretinin (CR), somatostatin (SOM), cholecystokinin (CCK), CR+SOM, CR+neuropeptide Y (NPY), CR+vasointestinal polypeptide (VIP), SOM+NPY, SOM+VIP, VIP+choline acetyltransferase (ChAT), CCK+NPY, CR+SOM+NPY, and CR+SOM+VIP expressing cells.

In some cases, any one of CAG, EF1α, a constitutive promoter (e.g., SV40, CMV, UBC, PGK, and CBA), or a non-selective regulatory element that drives gene expression in a non-cell type selective manner can be used for comparison with PV selective regulatory elements, or any cell type selective regulatory elements, disclosed herein. In some cases, a regulatory element that results in selective expression in PV cells at a level above the expression of a gene operably linked to CAG or EF1α control is indicative of selectivity to PV cells. In some cases, a regulatory element disclosed herein shows selective gene expression in PV cells that is at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% higher than the PV expression level from a transgene that is operably linked to CAG, EF1α, a constitutive promoter (e.g., SV40, CMV, UBC, PGK, and CBA), or a non-selective regulatory element (e.g., SEQ ID NO: 34, or a functional fragment thereof, or a sequence having at least 80%, at least 85%, at least 90%, at least 95%, or at least 99% sequence identity thereto), and as measured in a co-localization assay. In some cases, a regulatory element disclosed herein shows a selective gene expression in PV cells that is at least 1.5 fold, at least 2 fold, at least 3 fold, at least 4 fold, at least 5 fold, at least 6 fold, at least 7 fold, at least 8 fold, at least 9 fold, or at least 10 fold the expression level under CAG, EF1α, a constitutive promoter (e.g., SV40, CMV, UBC, PGK, and CBA), or a non-selective regulatory element (e.g., SEQ ID NO: 34, or a functional fragment thereof, or a sequence having at least 80%, at least 85%, at least 90%, at least 95%, or at least 99% sequence identity thereto) and as measured in a co-localization assay described herein.

In preferred cases, one or more regulatory elements described herein selectively drive expression of a transgene in a GABAergic cell, such as a GABAergic cell that expresses parvalbumin over at least one other CNS cell type (e.g., at least two, at least three, at least four, at least five non-PV cells, or two or more, three or more, or four or more non-PV cells and/or non-PV GABAergic neurons). In some cases, a target cell type is a GABAergic neuron that expresses parvalbumin, or PV cells.

One way of selectively expressing a transgene within a subpopulation of cells in the brain is to use a viral vector comprising a transgene operably linked to a cell-type selective regulatory element, or a regulatory element that is selective (or has selective activity) in the subpopulation of cells in the brain, e.g., PV cells. A viral vector can be selected to have high infectivity without selectivity for a particular cell type, while the regulatory element confers selectivity. For example, a cell-type selective regulatory element can drive expression of a transgene in PV neurons and not in other neurons.

In some cases, the present disclosure involves the use of regulatory elements (i.e., PV cell selective regulatory elements) that selectively drive expression in PV neurons.

GABAergic cells are inhibitory neurons which produce gamma-aminobutyric acid. GABAergic cells can be identified by the expression of glutamic acid decarboxylase 2 (GAD2). Other markers of GABAergic cells include GAD1, NKX2.1, DLX1, DLX5, SST, PV and VIP.

In some instances, a non-PV CNS cell is an excitatory neuron, a dopaminergic neuron, an astrocyte, a microglia, a motor neuron or a vascular cell. In some instances, a non-GABAergic neuron is a cell that does not express one or more of GAD2, GAD1, NKX2.1, DLX1, DLX5, SST and VIP. In some instances, a non-PV neuron is a GABAergic neuron that does not express parvalbumin. In some instances, other CNS cells refer to CNS cell types that have never expressed any of PV, GAD2, GAD1, NKX2.1, DLX1, DLX5, SST and VIP.

In some instances, a regulatory element disclosed herein is selective for a PV expressing cell over at least one, two, three, four, five, or more than five non-PV CNS cell-types. In some cases, non-PV cell types include non-PV GABAergic cells. In some cases, the cell type of interest is a PV cell. In some cases, REs selective for PV cells are referred to as PV cell selective regulatory elements.

In some cases, the PV cell selective regulatory elements disclosed herein include the sequences of SEQ ID NOS: 1-32, or any combination thereof.

In some cases, one or more PV cell selective regulatory elements or one or more regulatory elements disclosed herein are used to increase expression of a transgene in PV-expressing cells by at least 2, 5, 10, 15, 20, 30, 40, 50, 60, 70, 80, 90, 100, or more fold as compared to expression without the regulatory element. In some cases, a RE in an expression cassette increases gene expression by at least 1.5%, 2%, 5%, 10%, 15%, 20%, or 50%, or more than 1.5%, 2%, 5%, 10%, 15%, 20%, 25%, 30%, 35%, 40%, 45%, 50%, 55%, 60%, 65%, 70%, 75%, 80%, 85%, 90%, 95%, or 100% as compared to expression without the regulatory elements. In some cases, compositions and methods of use thereof comprise expression cassettes containing one or more regulatory elements that result in a 10-500% increase in transgene expression, e.g., expression of SCN1A, SCN2A, SCN8A, SCN1B, SCN2B, KCNC1 (also known as KV3.1), KCNC3 (also known as KV3.3), STXBP1, a DNA binding protein, or a variant or functional fragment thereof, or a protein thereof, as compared to the level without the regulatory elements or as compared to a non-selective regulatory element (e.g., CAG, EF1α, a constitutive promoter, or SEQ ID NO: 34, or a functional fragment thereof, or a sequence having at least 80%, at least 85%, at least 90%, at least 95%, or at least 99% sequence identity thereto). In some cases, the increase in gene expression and/or protein level of any one of SCN1A, SCN2A, SCN8A, SCN1B, SCN2B, KCNC1, KCNC3, and STXBP1 is 1.5-5%, 5%-10%, 10-15%, 15-20%, 20-30%, 30-40%, 40-50%, 50-60%, 60-70%, 70-80%, 80-90%, 90-100%, 100-150%, 150-200%, 250-300%, 300-350%, 350-400%, 400-450%, 450-500%, or 1.5-20%, 20%-50%, 50%-100%, 100-200%, 200-300%, 300-400%, or 400-500% as compared to the level without the expression cassette or regulatory elements. In some cases, such gene or protein expression is selective in PV cells as compared to an expression cassette comprising a control (e.g., CAG, EF1α, a constitutive promoter (e.g., SV40, CMV, UBC, PGK, and CBA), or a non-selective regulatory element) or a non-cell type selective regulatory element (e.g., SEQ ID NO: 34, or a functional fragment thereof, or a sequence having at least 80%, at least 85%, at least 90%, at least 95%, or at least 99% sequence identity thereto).

In some cases, selectivity of expression in PV cells can be calculated by dividing the number of cells that express both PV and eGFP (the transgene operably linked to one or more regulatory elements) by the total number of cells that express eGFP, and multiplying by 100 to convert into a percentage. PV cell selective regulatory elements as described herein can be highly selective for expression in PV cells. For example, PV cell selective regulatory elements or one or more regulatory elements disclosed herein can exhibit about 50%, 55%, 60%, 65%, 70%, 75%, 80%, 85%, 90%, 91%, 92%, 93%, 94%, 95%, 96%, 97%, 98%, 99%, or greater than about 99% selectivity for PV neurons.

In some cases, a PV cell selective regulatory element or any regulatory element disclosed herein confers selectivity in expressing a transgene in PV neurons at a level that is statistically higher than a control regulatory element, e.g., EF1α or a previously known regulatory element. In some instances, the statistical difference between a PV cell selective regulatory element and a control regulatory element is at least 2-fold, 5-fold, 10-fold, 20-fold, or more than 2-fold difference, or more than 5-fold, 10-fold, or 20-fold difference as determined by any one of the methods described herein, such as a co-localization assay.

The present disclosure includes regulatory elements that are selective for PV cells. These PV cell selective REs or any cell type selective REs are preferably short, preferably less than about 1100 base pairs, 1000 bp, 900 bp, 800 bp, 700 bp, 600 bp, 500 bp, 400 bp, 300 bp, 200 bp, or less than about 110 bp. The PV cell selective REs or any cell type selective REs can be between 1050 bp and 100 bp, between 100 bp and 500 bp, or between 500 bp and 1050 bp. Some examples of PV cell selective regulatory elements are provided by SEQ ID NOs 1-32, or a functional fragment or combination thereof. Other PV cell selective regulatory elements contemplated by the present disclosure include sequences having at least 80%, at least 85%, at least 90%, at least 95%, or at least 99% sequence identity to any of these sequences described herein, or a part or fragment of one of the sequences described herein.

In some cases, a PV cell selective regulatory element or any regulatory element disclosed herein has at least about 70%, 80%, 85%, 90%, 91%, 92%, 93%, 94%, 95%, 96%, 97%, 98%, 99% or more than 99% identity to a sequence described herein, or a fragment of a sequence described herein. In some cases, a PV cell selective regulatory element has at least about 80% identity to at least about 30%, 40%, 50%, 60%, 70%, 80%, 90% or 95% of a sequence described herein, or a functional fragment thereof.

In some cases, a PV cell selective regulatory element comprises at least 80% identity to any one or more of SEQ ID NOS: 1-32, or a functional fragment or a combination thereof, or sequences having at least 80%, at least 85%, at least 90%, at least 95%, or at least 99% sequence identity thereto. In some cases, a PV cell selective regulatory element has 90% identity to 50% or more of a sequence of any one of SEQ ID NOS: 1-22. In some instances, a PV-selective regulatory element is a functional fragment of any of SEQ ID NOS: 1-32 or a combination thereof. In some cases, the functional fragment is able to selectively express a transgene in PV cells with at least 50%, 55%, 60%, 65%, 70%, 75%, 80%, 85%, 90%, 95%, or greater than 95% selectivity of expression in PV cells.

In some cases, two or more PV cell selective regulatory elements of this disclosure or any two or more regulatory elements disclosed herein are combined to form combination regulatory elements. In some instances, two or more, three or more, four or more, five or more, six or more, seven or more, eight or more, nine or more, or ten or more PV cell selective regulatory elements, or a plurality of regulatory elements disclosed herein, are combined. For example, SEQ ID NO: 31 is a combination of SEQ ID NOs 1 and 23-29. As another example, SEQ ID NO: 32 is a combination of SEQ ID NO: 8 and SEQ ID NO: 23-29. In some cases, fragments of two or more PV-selective regulatory elements can be combined to form a combination regulatory element. For example, 50% of SEQ ID NO: 1 can be combined with 30% of SEQ ID NO: 8 and 90% of SEQ ID NO: 30 to form a combination regulatory element.

In some cases, one or more PV cell selective regulatory elements of this disclosure or any one or more regulatory elements disclosed herein selectively express an operably linked transgene in PV neurons as compared to one or more other CNS cell types. This selective expression can be quantified by counting the number of PV neurons which express detectable levels of the linked transgene as a percentage of the total number of cells expression the transgene, including the number of non-PV neurons which express the transgene. In other words, selectivity of a PV regulatory element in a particular cell type or target cell can be determined by measuring and/or comparing the number of PV neurons (or target cells) expressing the transgene that is operably linked to the regulatory element relative to the number of non-target cell types that express the transgene (or the total number of cells expressing the transgene).

In some cases, PV cell selective regulatory elements can exhibit about 50%, 55%, 60%, 65%, 70%, 75%, 80%, 85%, 90%, 91%, 92%, 93%, 94%, 95%, 96%, 97%, 98%, 99%, or greater than about 99% selectivity for PV neurons, PV neurons in the CNS, or GABAergic neurons that also express PV. In some cases, one or more regulatory elements of this disclosure can exhibit about 50%, 55%, 60%, 65%, 70%, 75%, 80%, 85%, 90%, 91%, 92%, 93%, 94%, 95%, 96%, 97%, 98%, 99%, or greater than about 99% selectivity for PV neurons as compared to CAG or EF1α or non-cell-type selective element, or as compared to non-PV CNS cells, or as compared to at least one, at least two, at least three, at least four, or at least five other non-PV GABAergic neuronal sub-types in the CNS.

In some cases, a PV selective regulatory element confers selectivity in expressing a transgene in PV neurons at a level that is statistically higher than a control regulatory element, e.g., CAG, EF1α, a constitutive promoter (e.g., SV40, CMV, UBC, PGK, and CBA), a non-selective regulatory element, or a previously known regulatory element. In some instances, the statistical difference between a PV cell selective RE and a control element is at least 2-fold, 5-fold, 10-fold, 20-fold, or more than 2-fold difference, or more than 5-fold, 10-fold, or 20-fold difference as determined by any one of the methods described herein. In some cases, the selectivity in PV is measured using a co-localization assay as described herein.

In some aspects, the cell-type selective regulatory elements described herein are useful for selectively modulating expression of a transgene in a CNS cell type compared to other CNS cell types. For example, the cell-type selective regulatory elements described herein can be useful for selectively modulating expression of a transgene in PV cells over other CNS cells, including other types of neurons. For gene therapy, selective expression of a transgene in a target cell type and/or minimized expression of the transgene in a non-target cell type can be desired. Expression of the transgene in an unintended cell-type (e.g., non-target cell type) can result in an adverse effect to the subject. Expression of the transgene in an unintended cell-type can counteract the therapeutic effect of the transgene in the intended cell type. For example, a transgene intended for expression in PV cells can have a negative effect for the subject if expressed in glutamatergic neurons. The cell-type selective regulatory elements described herein can be used in expression cassettes to ensure appropriate expression of a transgene and/or to reduce off-target effects of gene therapy.

The cell-type selective regulatory elements herein can be used in gene expression cassettes whereby they are operably linked to one or more transgenes. Such gene expression cassettes are used to deliver transgenes into cells for expression. The expression cassette can contain a cell-type selective regulatory element as described herein, a combination of cell-type selective regulatory elements, or a fragment of a cell-type selective regulatory element as described herein operably linked to a transgene.

Preferably, the expression cassettes herein include one or more cell-type selective regulatory elements operably linked to a transgene, whereby the two do not function together in their endogenous context in vivo. For example, a transgene for sodium ion channel beta subunit, such as SCN1B, can be operably linked to one or more regulatory elements that do not function in the same context in vivo, or do not detectably drive expression of SCN1B endogenously. Similarly, a nucleic acid cassette can encode a neurotransmitter regulator, such as STXBP1, operably linked to a regulatory element that does not function in the same context endogenously or in vivo, or is not in the same open reading frame, or is not on the same human chromosome, or does not detectably drive expression of STXBP1 in vivo. In some cases, a cell-type selective regulatory element is linked to a transgene, wherein the cell-type selective regulatory element does not regulate the endogenous gene corresponding to the transgene in vivo.

In some aspects, cell-type selective regulatory elements disclosed herein are derived from sequences isolated from a human chromosomal locus different from a locus of a native gene corresponding to the transgene. Thus, in some instances, an expression cassette comprises cell-type selective regulatory element(s) having a sequence derived from a chromosome different from the chromosome corresponding to the transgene on the same cassette. In other instances, regulatory element(s) of the disclosure and a transgene that are operably linked in an expression cassette are derived from sequences located more than 20 kb apart in the human genome, or at distal genomic locations. When two or more human derived regulatory elements are utilized on an expression cassette, the two or more regulatory elements can have sequences located more than 5 kb apart, more than 10 kb apart, more than 15 kb apart, or more than 20 kb apart in the human genome, or wherein the two or more regulatory elements do not interact with each other naturally in the genome.

In some cases, an expression cassette comprising PV-selective regulatory elements can exclude known sequences derived from hSyn1 or GAD2 promoter sequences. In some instances, the PV-selective regulatory elements do not comprise the full promoter sequence of any one of the GAD2, GAD1, SYN1, NKX2.1, DLX1, DLX5, SST and VIP promoters. In some instances, the PV-selective regulatory elements do not comprise more than 500 contiguous base pairs of sequence derived from the promoter or one or more of GAD2, GAD1, SYN1, NKX2.1, DLX1, DLX5, SST and VIP. In some instances, the PV-selective regulatory elements do not comprise sequences which are within 1 kb, 2 kb, 3 kb, 4 kb, 5 kb, 6 kb, 7 kb, 8 kb, 9 kb, or 10 kb of the transcription start site of any one of GAD2, SYN1, NKX2.1, DLX1, DLX5, SST, and VIP.

In some cases, a transgene is useful to treat a disease associated with a specific cell type of interest. In some cases, a cell type of interest is a neuron, an inhibitory neuron, a GABAergic neuron, or a PV neuron. In some cases, a transgene is any one or more of SCN1A, SCN2A, SCN8A, SCN1B, SCN2B, KV3.1, KV3.3, and STXBP1. In some cases, a transgene encodes a DNA binding protein that modulates expression of a gene (e.g., a transcriptional activator or a transcriptional repressor that modulates expression of an endogenous gene). In some cases, a transgene is a gene editing protein, such as a zinc finger nuclease, a transcription activator-like effector nuclease, a Cas family protein. In some cases, a transgene is a reporter gene or a detectable marker, such as eGFP, tdTomato, or RFP. In some cases, a transgene is a Cas protein, such as Cas9.

Transgenes useful to treat a condition associated with PV neuron cells can be incorporated in a vector, nucleic acid cassette, or method as described herein. Transgenes used herein generally do not contain introns or do not contain more than one intron. A transgene can be obtained from a cDNA sequence rather than from genomic sequence. In some cases, transgenes can contain some, or all, of their endogenous introns. In some examples, such a transgene encodes for a DNA binding domain or an ion channel. Examples of DNA binding domains that can be encoded for in the expression cassettes of this disclosure include zinc fingers, Cas9, a Cas family protein, dCas9, a dCas family protein or a transcriptional activator like effector (TALE). In some cases, the transgene is a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene comprises a gene editing protein, e.g., a Cas protein, Cas9. In some cases, the transgene is a subunit or a component of an ion channel or a membrane protein, or a gene associated with a neurological condition or disease disclosed herein. Examples of ion channel transgenes which can be used in the expression cassettes of this disclosure include voltage-gated and ligand-gated ion channels. Voltage-gated ion channels include sodium channels, calcium channels, potassium channels, and proton channels. In some instances, the transgene encodes a subunit of a voltage-gated sodium channel. Examples of voltage-gated sodium channel subunits include SCN1B (NM 001037.4), SCN1A (NM 001165963.1), and SCN2B, (NM 004588.4).

In some instances, the transgene encodes a subunit of a voltage-gated potassium channel. Examples of voltage-gated sodium channel subunits include KCNC1 (NM 001112741.1), and KCNC3 (NM 004977.2). In some cases, a transgene is any one or more of SCN1A, SCN2A, SCN8A, SCN1B, SCN2B, KV3.1, KV3.3, STXBP1, a variant and a functional fragment thereof. In some cases, a transgene is a sequence having at least 80%, at least 85%, at least 90%, at least 91%, at least 92%, at least 93%, at least 94%, at least 95%, at least 96%, at least 97%, at least 98%, at least 99%, or at least 99.5% sequence identity to any one of SCN1A, SCN2A, SCN8A, SCN1B, SCN2B, KV3.1, KV3.3, STXBP1, a variant or a functional fragment thereof. In some cases, such sequence identity is measured using BLAST.

In some cases, an expression cassette disclosed herein comprises one or more PV-selective regulatory elements or one or more regulatory elements of this disclosure operably linked to a transgene having at least 80%, at least 85%, at least 90%, at least 91%, at least 92%, at least 93%, at least 94%, at least 95%, at least 96%, at least 97%, at least 98%, at least 99%, or at least 99.5% sequence identity to a sequence encoding any one of SEQ ID NOS: 37-43, or a functional fragment or variant thereof, or the GenBank sequences corresponding to SEQ ID NOS: 37-43. In some cases, an expression cassette disclosed herein comprises a transgene having a sequence which encodes (i) a sequence of any one of SEQ ID NOS: 37-43, or (ii) a functional fragment thereof, or (iii) a sequence having at least 80%, at least 85%, at least 90%, at least 91%, at least 92%, at least 93%, at least 94%, at least 95%, at least 96%, at least 97%, at least 98%, at least 99%, or at least 99.5% sequence identity to (i) or (ii).

In some examples, the transgene encodes a neurotransmitter regulator, or a variant or functional fragment thereof. A neurotransmitter regulator may be involved in regulating production or release of a neurotransmitter in the CNS. For example, a neurotransmitter regulator may assist with synaptic fusion to release neurotransmitters. An example of a neurotransmitter regulator is STXBP1 (NM_001032221.3) or a functional fragment thereof, or a sequence having at least 80%, at least 85%, at least 90%, at least 95%, or at least 99% sequence identity thereto. The transgene may also be a subunit of a neurotransmitter regulator.

In some case, an expression cassette of this disclosure can contain an AAV2 5' ITR, a PV-selective enhancer, a PV-selective promoter, or a combination of one or more PV-selective promoters and enhancers, a cDNA of SCN1B, a WPRE, a hGH polyA signal, PV-selective regulatory element, and an AAV2 3' ITR. In one example, the expression cassette comprises an AmpR promoter, and AmpR coding sequence, a bacterial origin of replication, an AAV2 ITR, SEQ ID NO: 8, SEQ ID NOS: 23-29, a transgene (coding sequence, a WPRE, a human growth hormone poly A signal, a AAV2 ITR, and an f1 origin.

As another example, an expression cassette of this disclosure can contain an AAV2 5' ITR, an enhancer, a promoter, a transcriptional activator of the endogenous SCN1A gene, a WPRE, a hGH polyA signal, a regulatory element, and an AAV2 3' ITR. In some cases, an expression cassette comprises AAV2 5' ITR, a promoter, an intronic element, transcriptional modifier, synthetic polyA, and an AAV2 3' ITR. In some cases, an expression cassette of this disclosure can contain an AAV2 5' ITR, a PV-selective enhancer, a PV-selective promoter, a sequence encoding a transcriptional activator of SCN1A or SCN1B, a WPRE, a hGH polyA signal, a PV-selective regulatory element or any of the regulatory elements disclosed herein, and an AAV2 3' ITR.

An expression cassette comprising one or more regulatory element of this disclosure can be used to treat a medical condition. In some cases, an expression cassette containing a regulatory element of this disclosure is used to treat a neurological condition or a neurodegenerative condition. The neurological condition can be caused by a known genetic event or may have an unknown cause.

The neurological condition can be a disease associated with PV neurons. The neurological condition can be a disease associated with inhibitory neurons, such as PV neurons. Diseases or conditions associated with PV neurons can be treated by delivering an expression cassette carrying a transgene and one or more PV cell-selective regulatory elements or any of the regulatory elements as described herein to a cell in vivo. In some aspects, expression cassettes comprising a transgene operably linked to one or more PV cell-selective regulatory elements or any of the regulatory elements disclosed herein can be used to treat Dravet syndrome, Alzheimer's disease, epilepsy, a neurodegenerative disorder, tauopathy, neuronal hypoexcitability, and/or seizures. In some cases, an expression cassette of this disclosure is used to treat a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., Dravet syndrome, chronic traumatic encephalopathy, generalized epilepsy with febrile seizures plus (GEFS+), epileptic encephalopathy, temporal lobe epilepsy, focal epilepsy, tuberous sclerosis); and/or neurodegeneration (e.g., Alzheimer's disease, Parkinson's disease). In some cases, the neurological condition or disease is any seizure and/or epilepsy related condition or disease wherein PV neurons are implicated.

Majority of Dravet syndrome cases is associated with mutations in the SCN1A and/or SCN2A genes. Mutations or abnormalities in SCN1A has also been associated with seizure disorders, epilepsy, autism, familial hemiplegic migraine type 3 (FHM3), genetic epilepsy with febrile seizures plus (GEFS+), and effectiveness of certain anti-seizure medications. For instance, ICS5N+5G>A mutation in SCN1A is associated with the maximum safe amount (dose) of the anti-seizure drugs phenytoin and carbamazepine.

In some Alzheimer's patients, production of amyloid β (Aβ) involving many peptides and proteases that can affect excitability of neurons, causing seizures and downregulation of the NaV1.1 sodium channel in PV neurons.

Diseases associated with dysfunctional PV neurons such as those due to loss-of-function mutations in SCN1A or Nav1.1 include: Dravet syndrome, Ohtahara syndrome, epilepsy, early infantile epileptic encephalopathy 6 (EIEE6), familial febrile seizures 3A (FEB3A), intractable childhood epilepsy with generalized tonic-clonic seizures (ICEGTC), migraine, familial hemiplegic 3 (FHM3), Panayiotopoulos syndrome, familial atrial fibrillation 13 (ATFB13), generalized epilepsy with febrile seizures plus type 1 (gefs+ type 1), Brugada syndrome, non-specific cardiac conduction defect, generalized epilepsy with febrile seizures plus, benign familial infantile seizures, early infantile epileptic encephalopathy11 (EIEE11), benign familial infantile epilepsy, neurodegeneration, tauopathies, and Alzheimer's disease. In some cases, the neurological condition is Dravet syndrome. Dravet syndrome is associated with mutations in the SCN1A and/or SCN2A genes. In some cases, one or more regulatory elements of this disclosure are used in a gene therapy or an expression cassette to treat a neurological condition or disease associated with PV neurons, e.g., a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., Dravet syndrome, chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, one or more regulatory elements of this disclosure (e.g., PV neuron selective regulatory elements) are used to treat Dravet syndrome and/or Alzheimer's disease (e.g., in an expression cassette, a vector, or a gene therapy). In some cases, the neurological condition or disease is any seizure and/or epilepsy related condition or disease wherein PV neurons are implicated.

Methods and compositions of this disclosure can be used to treat a subject who has been diagnosed with a disease, for example, a neurological or neurodegenerative disease. The subject can be a patient suffering from a form of epilepsy. In some instances, the subject is a patient with Dravet syndrome. The subject can be a patient suffering from a neurodegenerative disease, for example, a patient with Alzheimer's disease. In some instances, epilepsy, encephalopathy, and/or seizures are associated with a genetic mutation in SCN8A. In some cases, a genetic mutation in SCN8A can give rise to epilepsy syndromes, e.g., Dravet syndrome. In some instances, a genetic mutation in STXBP1 is associated with encephalopathy with epilepsy, characterized by recurrent seizures.

In some instances, a subject treated with one or more compositions described herein is one diagnosed with a mutation or genetic aberration in a gene encoding an ion channel or a neurotransmitter regulator (e.g., a syntaxin binding protein). Examples of such mutations include mutations in SCN1A, SCN2A, SCN8A, SCN1B, SCN2B, KCNC1, KCNC3, and/or STXBP1, or combination thereof. The expression cassette containing a cell-type selective regulatory element as described herein can be delivered to a subject to treat or prevent a disease with symptoms associated with a specific cell type. For example, an expression cassette comprising a transgene operably linked to one or more PV cell selective regulatory element is delivered to a subject who has symptoms, or is at risk of developing symptoms, associated with PV neurons.

In some cases, the treatment can be administered to a subject with, or at risk of developing, Dravet syndrome. Symptoms associated with Dravet syndrome include seizures, memory defects, developmental delay, poor muscle tone and/or cognitive problems. Treatment with an expression cassette of this disclosure can result in an improvement of one or more symptoms, such as a reduction in number, duration, and/or intensity of seizures. Administration of a gene therapy as described herein to a subject at risk of developing Dravet syndrome can prevent the development of or slow the progression of one or more symptoms.

In another example the treatment may be administered to a subject suffering from Alzheimer's disease. Symptoms associated with Alzheimer's disease include short term memory loss, cognitive difficulties, seizures, and difficulties with language, executive functions, perception (agnosia), and execution of movements (apraxia). Treatment with an expression cassette of this disclosure can result in an improvement of one or more Alzheimer's disease symptoms, such as a reduction in progression of memory loss, or the prevention of one or more symptoms. In some cases, the treatment can result in a correction of high gamma power brain activity. The treatment can result in a decrease in seizure frequency and/or seizure severity, or a decrease in high gamma power activity by 10%, 20%, 30%, 40%, 50%, 60%, or 70%. In some cases, the treatment can result in an improvement in cognitive function. Learning and/or memory can be improved by 10%, 20%, 30%, 40%, 50%, 60%, 70%, 80%, 90%, 100% or more than 100%.

Methods and compositions of this disclosure can be used to treat a subject who is at risk of developing a disease. The subject can be known to be predisposed to a disease, for example, a neurological disease or a disease associated with epilepsy, seizures, and/or encephalopathy. The subject can be predisposed to a disease due to a genetic event, or due to known risk factors. For example, a subject can carry a mutation in SCN1A which is associated with Dravet syndrome. In some cases the subject can be predisposed to a disease such as Alzheimer's disease due to the age of the subject.

The treatment can result in a decrease or cessation of symptoms. For example, treatment can improve learning, memory, cognitive function, and/or motor function; reduce frequency and/or duration of seizures; and/or reduce temperature sensitivity (or increase the temperature threshold for triggering a seizure).

In some instances, the target cell type of a gene therapy or expression cassette disclosed herein is a PV cell. In some cases, the non-target cell subtypes are at least one, at least two, at least three, or at least four of the non-PV GABAergic subtypes disclosed herein. In some cases, an expression cassette comprising a regulatory element disclosed herein is selective for PV cells over all non-PV CNS cells. In some cases, cell-type selectivity is measured according to a co-localization assay disclosed herein. In some cases, cell-type selectivity is measured using a mouse that expresses Cre in the target cell type.

In some instances, the treatment does not result in an adverse reaction for the subject. Treatment with a gene therapy containing a PV-selective regulatory element can cause fewer, or less severe, adverse reactions in a subject than treatment with a similar gene therapy containing the same transgene linked to a non-selective regulatory element.

In various aspects, any expression cassette disclosed herein can be adapted for or used in a gene therapy (e.g., rAAV or rAAV9 gene therapy) to treat any one or more of Dravet syndrome, Alzheimer's disease, epilepsy, neurodegeneration, tauopathy, neuronal hypoexcitability and/or seizure. In some cases, a gene therapy comprises any one or more, two or more, three or more, four or more, five or more, six or more, seven or more, eight or more, nine or more, or ten or more of SEQ ID NOS: 1-32, or a functional fragment or a combination thereof, or sequences having at least 80%, at least 85%, at least 90%, at least 95%, or at least 99% sequence identity thereto, operably linked to a transgene. In some cases, a gene therapy comprises an expression cassette of this disclosure. In some cases, a gene therapy comprises one or more regulatory elements disclosed herein operably linked to any transgene (e.g., a reporter transgene or a therapeutic transgene) such that the regulatory elements drive selective expression or preferential expression in at least one target cell type at a level that is statistically significantly higher than the expression driven by CAG or EF1α or a non-selective regulatory element when operably linked to the same transgene, or by the same construct without the regulatory elements. In some cases, statistically significantly higher means the regulatory elements drive selective expression in the target cell type at a level that is at least 1.1, 1.2, 1.3, 1.4, 1.5, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, or 100 times the expression level by the CAG, EF1α, a constitutive promoter, or a non-selective regulatory element when operably linked to the same transgene in the target cell type, or by the same construct without the regulatory elements. In some cases, such cell-type selective expression is assayed using a co-localization assay as described herein. In some cases, the transgene is any one or more of SCN1A, SCN2A, SCN8A, SCN1B, SCN2B, KV3.1, KV3.3, STXBP1, and a functional fragment thereof. In some cases, the transgene encodes a DNA binding protein that modulates expression of an endogenous gene, such as a transcriptional modulator, a transcriptional activator, or a transcriptional repressor. In some cases, the transgene encodes a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene is a gene editing protein, such as a zinc finger nuclease or a transcription activator-like effector nuclease. In some cases, a transgene is a reporter gene or a detectable marker, such as eGFP, tdTomato, or RFP. In some cases, a transgene is a Cas protein, such as Cas9.

In some cases, a gene therapy comprising an expression cassette disclosed herein is used to treat a neurological condition or disease. In some cases, a gene therapy comprising an expression cassette disclosed herein is used to treat a neurological condition or disease, wherein the expression cassette comprises any one or more, two or more, three or more, four or more, five or more, six or more, seven or more, eight or more, nine or more, or ten or more of SEQ ID NOS: 1-32, or a functional fragment or a combination thereof, or sequences having at least 80%, at least 85%, at least 90%, at least 95%, or at least 99% sequence identity thereto, operably linked to a transgene. In some cases, the transgene encodes any one or more of SCN1A, SCN2A, SCN8A, SCN1B, SCN2B, KV3.1, KV3.3, STXBP1, a DNA binding protein, and a functional fragment thereof. In some cases, a gene therapy comprising an expression cassette disclosed herein is used to treat Dravet syndrome. In some aspects, a gene therapy comprising an expression cassette disclosed herein is used to treat Alzheimer's disease. In some cases, a gene therapy comprising an expression cassette disclosed herein is used to treat epilepsy and/or seizure symptoms associated with Dravet syndrome and/or Alzheimer's disease. In some cases, treating any one of Dravet syndrome, Alzheimer's disease, epilepsy, neurodegeneration, tauopathy, neuronal hypoexcitability and/or seizures comprises delivering or administering a gene therapy of this disclosure to a cell of a subject in need thereof. In some cases, the subject in need thereof is at risk for or has any one of Dravet syndrome, Alzheimer's disease, epilepsy, and/or seizures. In some cases, the subject is a child or a minor. In some cases, a gene therapy comprising an expression cassette disclosed herein is used to treat an infant, a child, or a minor diagnosed with or is at risk of developing Dravet syndrome. In some cases, a gene therapy comprising an expression cassette disclosed herein is used to treat a subject comprising a mutation or a genetic defect in any one or more of SCN1A, SCN2A, SCN8A, SCN1B, SCN2B, KV3.1, KV3.3, and STXBP1.

In some aspects, the present disclosure provides a method of treating any one of Dravet syndrome, Alzheimer's disease, epilepsy, neurodegeneration, tauopathy, neuronal hypoexcitability and/or seizures, comprising administering a gene therapy into a cell of a subject, wherein the gene therapy comprises an expression cassette disclosed herein. In some cases, such expression cassette comprises any one or more of SEQ ID NOS: 1-32, or a functional fragment or a combination thereof, or sequences having at least 80%, at least 85%, at least 90%, at least 95%, or at least 99% sequence identity thereto, operably linked to a transgene, wherein the transgene is any one of SCN1A, SCN2A, SCN8A, SCN1B, SCN2B, KV3.1, KV3.3, STXBP1, and a functional fragment thereof. In some cases, the transgene encodes a subunit of a sodium ion channel or a potassium ion channel. In some cases, the transgene is a syntaxin-binding protein. In some cases, the transgene is a transcriptional modulator, e.g., a transcriptional activator or a transcriptional repressor. In some cases, the transgene is a transcriptional modulator that modulates the expression of an endogenous gene (e.g., SCN1A, SCN2A, SCN8A, SCN1B, SCN2B, KV3.1, KV3.3, or STXBP1). In some cases, a transgene is a gene editing protein, such as a zinc finger nuclease or a transcription activator-like effector nuclease. In some cases, the transgene is a Cas protein, such as Cas9.

In other aspects, the present disclosure provides a method for modifying any gene therapy designed for treating Dravet syndrome, Alzheimer's disease, epilepsy, neurodegeneration, tauopathy, neuronal hypoexcitability and/or seizures by adding one or more regulatory elements disclosed herein to improve the cell-type selectivity of the gene therapy. In some cases, the gene therapy is an rAAV gene therapy.

In some cases, treatment with an expression cassette disclosed herein reduces seizure duration and/or frequency, e.g., seizures associated with Dravet syndrome, by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 45%, 50%, 55%, 60%, 65%, 70%, 75%, 80%, 85%, 90%, or 95% as compared to an untreated control or as compared to the level before treatment.

In some cases, treatment with an expression cassette disclosed herein reduces high gamma power activity (e.g., high gamma power activity associated with Alzheimer's disease) by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 45%, 50%, 55%, 60%, 65%, 70%, 75%, 80%, 85%, 90%, or 95% as compared to an untreated control or as compared to the level before treatment.

In one aspect, the present disclosure provides a nucleic acid cassette of this disclosure comprises one or more regulatory elements operably linked to a transgene that result in selective expression in a target cell type over one or more non-target cell types, e.g., selective expression in PV neurons in the CNS over one or more non-PV CNS cell types. In some cases, each of the regulatory elements comprises (i) a sequence of SEQ ID NOS: 1-32, (ii) a functional fragment or a combination thereof, or (iii) a sequence with at least 80% sequence identity to (i) or (ii). In some cases, the percent sequence identity can be measured using BLAST. In some cases, at least one of the regulatory elements is human derived. In some cases, at least one of the regulatory elements is derived from a non-human mammal. In some cases, the regulatory elements are non-naturally occurring. In some cases, the regulatory elements result in a selectivity of expression in PV cells that is greater than expression of the transgene operably linked to CAG or EF1α or a non-selective regulatory element as measured by a co-localization assay. In some cases, a transgene encodes any one or more of SCN1A, SCN2A, SCN8A, SCN1B, SCN2B, KV3.1, KV3.3, and STXBP1, or a functional fragment hereof, or sequences having at least 80%, at least 85%, at least 90%, at least 95%, or at least 99% sequence identity thereto. In some cases, a transgene encodes a DNA-binding protein that modulates expression of a gene (e.g., an endogenous gene such as SCN1A, SCN2A, SCN8A, SCN1B, SCN2B, KV3.1, KV3.3, and STXBP1), such as transcriptional modulator, transcriptional activator, or transcriptional repressor. In some cases, a transgene is a gene editing protein, such as a zinc finger nuclease or a transcription activator-like effector nuclease. In some cases, a transgene is a reporter gene or a detectable marker, such as eGFP, tdTomato, or RFP. In some cases, a transgene is a Cas protein, such as Cas9. In some cases, the regulatory elements result in selective expression in PV cells at a level that is at least 0.5-fold, at least 0.6-fold, at least 0.7-fold, at least 0.8-fold, at least 0.9-fold, at least 1.1-fold, at least 1.2-fold, at least 1.3-fold, at least 1.4-fold, at least 1.5-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, at least 50-fold, at least 60-fold, at least 70-fold, at least 80-fold, at least 90-fold, at least-100 fold as compared to that of a CAG or EF1α or a non-selective regulatory element, as measured by the co-localization assay. In some cases, a fold difference refers to the fold difference between the percentage of eGFP+, PV+ cells that result from one or more regulatory elements and that of a non-selective regulatory element. In some cases, the co-localization assay is an immunohisto-chemical assay, as described below in Example 5. In some instances, a co-localization assay is performed using a commercially available anti-PV antibody. In some cases, the transgene encodes an ion channel subunit, a neurotransmitter regulator, or a variant or a functional fragment thereof. In some cases, the ion channel subunit is an alpha subunit or a beta subunit of a sodium ion channel or a subunit of a potassium ion channel. In some cases, the transgene is any one of (i) SCN1A, SNC2A, SNC8A, SCN1B, SCN2B, KV3.1, KV3.3, or a DNA binding protein; (ii) a functional fragment thereof; or (iii) a sequence having at least 80% sequence identity to (i) or (ii). In some cases, the neurotransmitter regulator is (i) STXBP1, (ii) a functional fragment thereof, or (iii) a sequence having at least 80% sequence identity to (i) or (ii). In some cases, the regulatory elements and the operably linked transgene are located on different chromosomes. In some cases, the regulatory elements combined are less than 2.5 kb, less than 1.5 kb, less than 1 kb, or less than 500 bp in size. In some cases, the non-PV cells comprise any one or more of non-PV CNS cell types, including but not limited to excitatory neurons, dopaminergic neurons, astrocytes, microglia, or motor neurons. In some cases, the nucleic acid cassette is a linear construct. In some cases, the nucleic acid cassette is a vector. In some cases, the nucleic acid cassette is a plasmid. In some cases, the vector is a viral vector. In some cases, the viral vector is an adeno-associated virus (AAV) vector. In some cases, the AAV vector is AAV1, AAV8, AAV9, scAAV1, scAAV8, or scAAV9. In some cases, the viral vector is a lentiviral vector. In some cases, the regulatory elements contain less than 600 bp of contiguous sequence from within 10 kb of the transcription start site of GAD2, GAD1, SYN1, NKX2.1, DLX1, DLX5/6, SST, PV, and/or VIP.

In various embodiments disclosed herein, a regulatory element is less than 2050 bp, 2000 bp, 1900 bp, 1800 bp, 1700 bp, 1600 bp, 1500 bp, 1400 bp, 1300 bp, 1200 bp, 1100 bp, 1000 bp, 900 bp, 800 bp, 700 bp, 600 bp, 500 bp, 400 bp, 300 bp, 200 bp, 100 bp, 90 bp, 80 bp, 70 bp, 60 bp, 50 bp, 40 bp, 30 bp, 20 bp, 10 bp, or 5 bp. In various embodiments disclosed herein, an expression cassette comprises a transgene that is larger than a typical transgene size in a conventional viral vector, e.g., AAV. In some aspects, an expression cassette of any embodiment disclosed herein comprises a transgene that is at least 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, 7.5 kb, or 8 kb. In some aspects, any embodiment disclosed herein comprises an expression cassette (e.g., AAV) that comprises a transgene that is more than 1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or 4 kb in size. In some aspects, any embodiment disclosed herein can further comprise one or more heterologous nucleic acid sequence or element.

In one aspect, a method of treating a neurological disorder or condition in a subject in need thereof comprises delivering a therapeutically effective amount of a nucleic acid cassette described herein. In another aspect, a method of increasing selective expression of a transgene in PV neurons comprises contacting a cell with a nucleic acid cassette described herein. In some cases, a method of any embodiment disclosed herein is used to treat a neurological condition or disease, e.g., a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., Dravet syndrome, chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, a method of any embodiment disclosed herein can be used to treat Dravet syndrome. A method of any embodiment disclosed herein can be used to treat Alzheimer's disease. In some cases, methods and/or compositions of this disclosure can be used to treat any neurological condition or disease associated with seizure and/or epilepsy, and/or wherein PV neurons are implicated.

In one aspect, a neurological condition described herein is treated with a gene therapy, preferably one that results in preferential expression in one tissue type or cell type over another, e.g., a PV neuron as determined via a co-localization assay. In some cases, the gene therapy is an AAV.

In one aspect, a method of targeting expression of any transgene to PV neurons in the CNS comprises operably linking one or more of PV neuron selective regulatory elements to a transgene. In some cases, the regulatory elements comprise one or more sequences of SEQ ID NOS: 1-32, or sequences with at least 80% sequence identity to SEQ ID NOS: 1-32, or a functional fragment thereof. In some cases, the regulatory elements result in selective expression in PV neurons at a level that is at least 2-fold, at least 5-fold, or at least 7-fold, or at least 10-fold as compared to CAG or EF1α or a non-selective regulatory element operably linked to the transgene, as measured by a co-localization assay. In some cases, the transgene encodes SCN1A, SCN2A, SCN8A, SCN1B, SCN2B, KV3.1, KV3.3, STXBP1, a DNA-binding protein, or a functional fragment thereof. In some cases, the regulatory elements and the transgene are in an AAV. In some cases, the AAV is AAV9.

In one aspect, a method of treating a neurological condition or disorder in a subject in need thereof comprises contacting a cell with a nucleic acid cassette comprising one or more regulatory elements operably linked to a transgene that results in selective expression in PV neurons over one or more non-PV CNS cells. In some cases, the regulatory elements comprise one or more of SEQ ID NOS: 1-32, or a functional fragment or a combination thereof, or sequences having at least 80%, at least 85%, at least 90%, at least 95%, or at least 99% sequence identity thereto. In some cases, the transgene is a voltage-gated ion channel subunit, or a variant or a functional fragment thereof. In some cases, the subunit is a beta subunit of a sodium ion channel. In some cases, the subunit is an alpha subunit of a sodium ion channel. In some cases, the subunit is of a potassium ion channel. In some cases, the transgene encodes any one of (i) SCN1A, SCN2A, SCN8A, SCN1B, SCN2B, KV3.1, KV3.3, a DNA-binding protein or STXBP1; (ii) a functional fragment thereof; or (iii) a sequence having at least 80% sequence identity to (i) or (ii). In some cases, the neurological condition or disorder is associated with a haploinsufficiency or a mutation in any of SCN1A, SCN1B, SCN2B, KV3.1, and KV3.3. In some cases, the neurological condition or disorder is Dravet syndrome. In some cases, the neurological condition or disorder is Alzheimer's disease. In some cases, the neurological condition or disease is a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, the neurological condition or disease is any seizure and/or epilepsy related condition or disease wherein PV neurons are implicated. In some cases, the nucleic acid cassette results in selective expression in PV neurons at a level that is at least 2-fold, at least 5-fold, or at least 7-fold, or at least 10-fold as compared to CAG or EF1α or a non-selective regulatory element operably linked to the transgene, as measured by a co-localization assay. In some cases, the nucleic acid cassette is in an AAV. In some cases, the AAV is AAV9.

In one aspect, a method of treating Dravet syndrome comprises contacting a cell with an AAV comprising a transgene that encodes any one of (i) SCN1A, SCN1B, SCN2B, a DNA binding protein (ii) a functional fragment thereof, or (iii) a sequence having at least 80% sequence identity to (i) or (ii). In some cases, the AAV further comprises one or more PV neuron selective regulatory elements or any of the regulatory elements disclosed herein operably linked to the transgene. In some cases, each of the regulatory elements independently comprises a sequence comprising any one of SEQ ID NOS: 1-32, or any functional fragment or combination thereof, or a sequence comprising at least 80% sequence identity to any one of SEQ ID NOS: 1-32.

In another aspect, a method of treating Alzheimer's disease comprises contacting a cell with an AAV comprising a transgene encodes any one of (i) SCN1A, SCN2B, KV3.1, KV3.3, and STXBP1, (ii) a functional fragment thereof, and (iii) a sequence having at least 80% sequence identity to (i) or (ii). In some cases, the AAV further comprises one or more PV neuron selective regulatory elements operably linked to the transgene. In some cases, each of the regulatory elements independently comprises a sequence comprising any one of SEQ ID NOS: 1-32, or any functional fragment or combination thereof, or a sequence comprising at least 80% sequence identity to any one of SEQ ID NOS: 1-32.

EXAMPLES

These examples are provided for illustrative purposes only and not to limit the scope of the claims provided herein.

Example 1

Identifying Putative PV-Selective Regulatory Elements

To identify and screen putative regulatory element that are selective for PV cells, one can harvest PV cells from a R26-CAG-LSL-Sun1-sfGFP-Myc knockin mouse using affinity purification, e.g., using anti-GFP or anti-Myc antibodies and protein G-coated magnetic beads. PV cells can be enriched by using anti-PV antibody coated beads or affinity purification matrix. Nuclei are then isolated from the PV cells. Nuclear RNA can be purified from the nuclei and converted to cDNA, and amplified with the Nugen Ovation RNA-seq System V2 (Nugen 7102), followed by sequencing using the Illumina HISEQ® 2500. Genomic DNA can be purified from nuclei, fragmented, and used to make meth-ylC-seq libraries, which can be sequenced using the Illumina HISEQ® 2000. To generate an ATAC-seq library, nuclei bound to beads are transposed using Tn5 transposase (Illumina FC-121-1030). After 9-12 cycles of PCR amplification, libraries are sequenced using an Illumina HISEQ® 2500. To generate a ChIP-seq library, nuclei of PV cells are digested to mononucleosomes using micrococcal nuclease, followed by salt extraction of chromatin, and native ChIP and library construction, which can be sequenced on an Illumina HISEQ® 2500. After sequencing these libraries, the sequences are mapped to identify correlations and patterns in hypo-methylation in CG-rich regions, histone modifications, transcription factor binding sites, and patterns associated with highly expressed transcription factors in PV cells. Overlapping features and correlations from multiple assays and/or libraries described above provide convergent evidence for identifying candidate sequences that are putative PV-selective regulatory elements. Putative PV-selective regulatory elements can be further tested using a co-localization assay as described in Example 5 below. Putative PV-selective regulatory elements can also be tested in B6 PV-Cre mouse (Jackson Laboratory), which is a B6 PV-Cre knock-in mouse that expresses Cre recombinase in parvalbumin-expressing cells, as described in Example 2 below. After validating PV-selectivity of the regulatory elements, the regulatory elements can be operably linked to a transgene to target expression selectively to PV cells over at least one, two, three, four, five, or more than five non-PV cells.

Example 2

Selectivity for PV Neurons in PV-Cre Mouse

Selectivity for PV neurons can be determined using fluorescent imaging. AAV9 vectors containing eGFP operably linked to (i) a control promoter (EF1α); or (ii) a PV-selective RE identified in Example 1 above; or (iii) a PV-selective RE selected SEQ ID NOS: 1-32; and AAV9 vectors containing a Cre-dependent tdTomato are co-injected into a B6 PV-Cre mouse (Jackson Labs). PV-Cre is a knock-in mouse that expresses Cre recombinase in parvalbumin-expressing neurons (such as interneurons in the brain and proprioceptive afferent sensory neurons in the dorsal root ganglia), without disrupting endogenous Parvalbumin expression.

Mice are infused bilaterally with 1.5 μL of AAV9 vector ($5^{12}$ to $1^{13}$ gc/ml) into the dorsal and ventral hippocampus at a rate of 0.3 μL/min with a 4 min rest period following injection. Mice are anesthetized for the injection. The animals are placed in a stereotaxic frame (Kopf instruments, USA), using the following coordinates for the dorsal hippocampus (AP −2.0 mm, lateral±1.5, DV −1.4 mm from dura) and the ventral hippocampus (AP −3.1 mm, lateral±2.8, DV −3.8 mm from dura). A Hamilton syringe (model #80308; 10 μL syringe with corresponding 30 ga blunt tip needle) can be used with the stereotactic micromanipulator, to designate and drill the bur holes. The drill is only used to penetrate the bone. Following drilling, the infusion cannula is lowered into the brain to the depth of the desired location for injection, e.g., injection volume: 1.5 μL; injection rate: 0.3 μL/min. Prior to infusion, the needle is allowed to equilibrate for 1 minute. Once delivery is completed, the needle is left for 4 min and then withdrawn over approximately 1 min. Once all infusions are complete, the skin incision is closed with sutures and administered post-surgery analgesics. The treated mice undergo daily health checks for the remainder of the study and are weighed once weekly to monitor body weight.

For tissue collection, mice are euthanized via isoflurane overdose and perfused with 4% Paraformaldehyde (PFA). A piece of brain tissue containing the hippocampus is extracted and placed in 4% PFA at 4° C. for at least 12 hours. The brain tissue is then dehydrated in 30% sucrose (in phosphate buffered saline) at 4° C. until the tissue sinks to the bottom of the tube. Brain tissue is embedded in TISSUE-TEK® OCT for sectioning in a cryostat. Sectioned brain tissue is stained for eGFP and tdTomato using standard immunohistochemistry procedures with anti-RFP polyclonal rabbit antibody (Rockland Antibodies and Assay) and anti-eGFP polyclonal chicken antibody (Ayes Labs). Fluorescence microscope imaging is used to visualize the cells. eGFP, or green fluorescence, corresponds to all gene expression.

Red fluorescence from tdTomato corresponds to PV+ cells. An overlap of the two fluorescence signals, which can be visualized as yellow or white cells, represents PV+ cells that express the eGFP transgene. AAV9 vectors comprising a PV-selective regulatory element is expected to yield higher number of cells that are eGFP+ and PV+ as compared to the control promoter (EF1α). For example, fluorescence imaging of cells from mice injected with AAV9s comprising any one of PV-selective REs (e.g., SEQ ID NOS: 1-32 or putative REs identified in Example 1) are expected to show higher number of eGFP+ cells that are also PV+. Selectivity for PV cells can be quantified as percentage of all eGFP+ cells that are also PV+.

Example 3

Reduction of Seizures in Dravet Mouse Model

B6(Cg)-Scn1a$^{tm1.1Dsf}$J mice were obtained from the Dravet syndrome European Federation via the Jackson Laboratories. These mice contain a Dravet syndrome associated mutation in exon 24 of SCN1A (A to V at position 1783). The mice also contain a floxed exon 24 with wild-type sequence. When not manipulated, this strain of mice expresses two copies of the WT allele of SCN1A. However, upon delivery of an AAV expressing Cre recombinase, any cell targeted by the AAV will switch to expressing one copy of the mutant allele. Upon expression of the mutant SCN1A subunit, mice develop spontaneous seizures within 10 days.

B6(Cg)-Scn1a$^{tm1.1Dsf}$/J and control C57Bl/6 mice were injected, as in Example 2, with AAVs expressing CRE recombinase under the control of the EF1α promoter and an AAV comprising PV cell selective regulatory element SEQ ID NO: 32 driving expression of either eGFP (SEQ ID NO: 36) or SCN1B (SEQ ID NO: 37). Once all four infusions were complete, telemetry implantation was performed immediately, (F20-EET, Data Sciences International). Electrocorticogram data was monitored continuously for 14 days from 10 days after the surgery. Electrocorticogram data was analyzed and all seizure events were recorded, annotated with date, time start, time stop, duration of the seizures, and severity score. FIG. 1 illustrates the frequency of seizures in 12 hour windows over 14 days following treatment. The mice treated with SCN1B showed a trend towards lower seizure frequency compared to the control animals.

This observation was consistent with the notion that the beta unit of the sodium ion channel, e.g., SCN1B, can contribute to the trafficking and assembly of the sodium ion channel and that increasing the expression of the beta unit selectively in PV neurons can result in increased trafficking and assembly of the Nav1.1 channel, thus leading to a trend towards lower seizure frequency and duration in the mice treated with SCN1B gene therapy.

Example 4

Treating Alzheimer's Disease in a Mouse Model

Female APP/PS1 and WT mice bred at PSYCHOGEN-ICS® were used in the study. APP/PS1 mice contain human transgenes for both Amyloid Beta Precursor Protein (APP) bearing the Swedish mutation (670 G-T and 671 A-C) and Presenilin 1 (PSEN1) containing an L166P mutation, both under the control of the Thy1 promoter. These mice develop symptoms of Alzheimer's disease, including amyloid plaques and memory defects. Further description of these mice can be found in Radde et al., 2006 ("Aβ42-driven cerebral amyloidosis in transgenic mice reveals early and robust pathology." *EMBO Reports* 7.9 (2006): 940-946).

Figure 2:
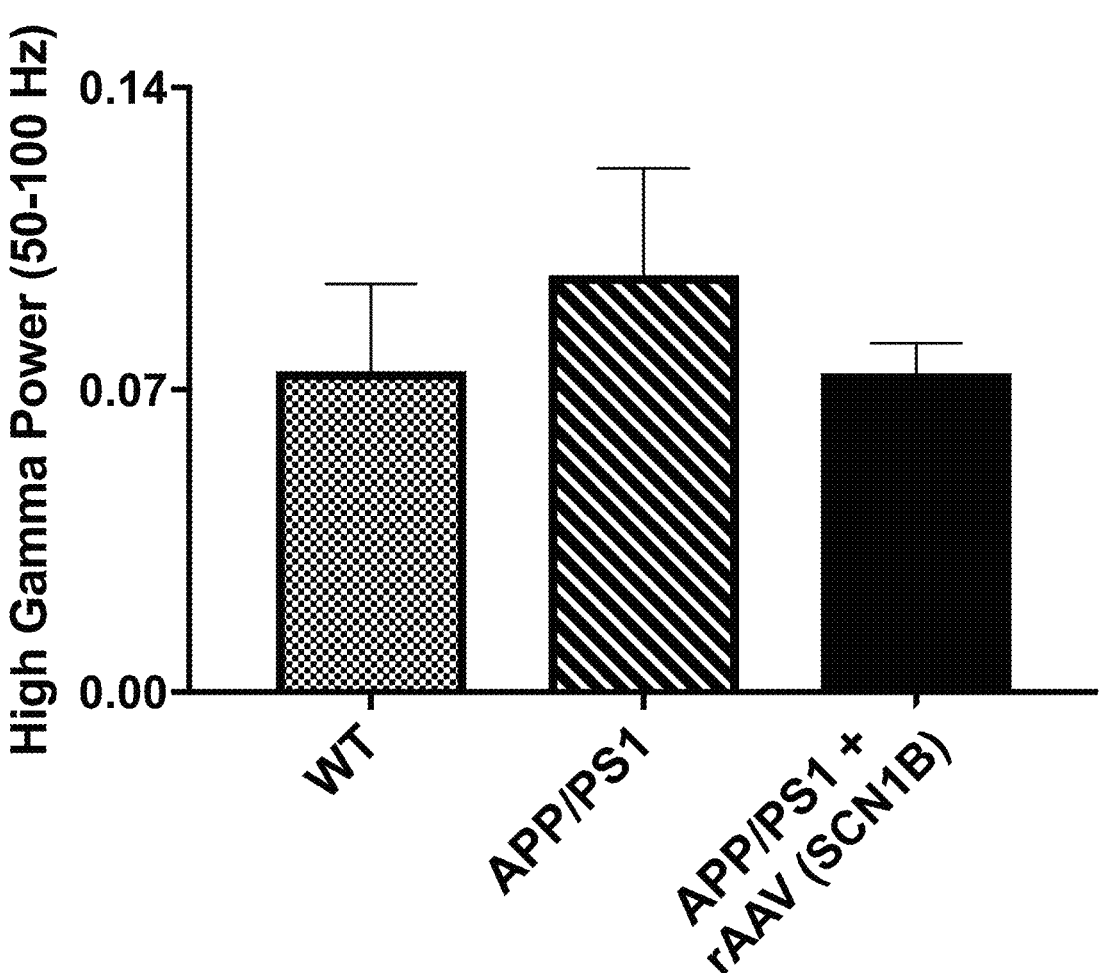
FIG. 2 illustrates high gamma power (50-100 Hz) of different mice: wild-type control (WT), untreated transgenic APP/PS1 mice (APP/PS1), or transgenic APP/PS1 mice treated with rAAV comprising SCN1B operably linked to a regulatory element comprising a sequence of SEQ ID NO: 32 (APP/PS1+SCN1B).

APP/PS1 mice were used as a model to determine the effect of treatment with SCN1B under the control of a RE on symptoms of Alzheimer's disease. APP/PS1 mice and non-transgenic controls were injected with either a control vector expressing eGFP or a treatment vector expressing SCN1B, both under the control of SEQ ID NO: 32; and implanted with an EET transmitter as in Example 3. Brain activity was assessed over 24 hours at 4 weeks after surgery. Electrocorticogram data was automatically analyzed and power levels in the different frequency bands were compared. FIG. 2 illustrates the high gamma power (50-100 Hz) in non-transgenic controls (WT), APP/PS1, and APP/PS1 mice treated with SCN1B. Increased high gamma power activity is associated with seizures in Alzheimer's patients and epilepsy patients. The APP/PS1 mice showed a higher level of high gamma power activity than the control mice. However, the increase was absent in the treated mice indicating effective treatment with the vector.

Example 5

Selectivity for PV Neurons in C57BL/6J (WT) Mouse

The selectivity of various REs disclosed herein were tested for selective gene expression in PV neurons using immunohistochemical methods. C57BL/6J (WT) mouse line was used for the PV immunohistochemical assays. Expression cassettes comprising reporter transgene eGFP operably linked to a regulatory element (SEQ ID NO: 1 or SEQ ID NO: 8) or a CAG promoter in an AAV9 construct.

Pup systemic infusions: Postnatal day 1 C57BL/6J mice were infused via facial vein injection with AA9 vector ($1 E^{12}$ to $3 E^{12}$) using a 300 U insulin syringe with a 31 G needle. For tissue collection, mice were euthanized 21 days post-infusion via overdose of sodium pentobarbital (i.p.) and perfused with heparinized (2.5 IU/ml) saline followed by perfusion with 4% formaldehyde. Brains were removed and subsequently immersion-fixed in 4% formaldehyde for 24-48 hours at 4 degrees Celsius. The brain was then placed into PBS containing 30% sucrose and allowed to sink at 4 degrees Celsius (~2-3 days). Upon sinking the individual brain hemispheres were frozen in TISSUE-TEK® OCT with the midline facing down. Frozen brains were processed for sagittal sections on a cryostat and placed free-floating into PBS. Sections were stained for eGFP and parvalbumin (PV) using standard immunohistochemistry procedures with chicken anti-GFP (Ayes Lab, GFP-1020) and mouse anti-PV (Sigma, P3088).

Adult systemic infusions: 4-week-old C57BL/6 mice were infused via tail vein injection with 60 µL of AAV9 vector ($4.9^{13}$ to $1^{14}$ gc/ml) expressing eGFP. For tissue collection mice were euthanized 21 days post-infusion via isoflurane overdose and whole brains were extracted, washed with PBS and placed into separate 5 ml tubes containing ice cold 4% formaldehyde. Tissue was fixed at 4 degrees Celsius overnight. The following day, the brain was placed into PBS containing 30% sucrose and allowed to sink at 4 degrees Celsius. Upon sinking the individual brain hemispheres were frozen in Tissue-Tek OCT with the midline facing down. Frozen brains were processed for sagittal sections on a cryostat and placed free-floating into PBS. Sections were stained for EGFP and parvalbumin (PV) using standard immunohistochemistry procedures with chicken anti-GFP (Ayes Lab, GFP-1020) and mouse anti-PV (Sigma, P3088).

Immunohistochemistry protocol: Immunohistochemistry was used to analyze the co-localization of eGFP signal and PV signal using the anti-PV antibody, wherein overlay of the signals exhibited as white or light gray spots in the top panel images (merge), wherein representative overlay was indicated by arrowheads. Overlay of the eGFP and PV fluorescence is indicative of expression in PV cells. Such experiments can be used to determine the selective expression of expression in PV cells. To perform the immunohistochemical experiments, tissues obtained from each mouse were blocked with a Blocking Buffer Solution (comprising 3% BSA, 3% NGS, 0.3% Triton X-100, 0.2% Tween-20 in 1×PBS) for 1 hour at room temperature. The tissues were then incubated with primary antibodies in blocking buffer overnight at 4 C, washed three times with 1 mL 1×PBS, each with 5 minutes interval. Then the tissues were incubated with secondary antibodies in blocking buffer for 1 hour at room temperature, followed by washing three times, each time with 1 mL 1×PBS and with 5 minutes interval. The tissues were incubated DAPI (1:1000) in PBS buffer for 5 minute and wash twice with 1 mL 1×PBS. Tissues were mounted onto slides, imaged, and analyzed using a fluorescence microscope. Images were taken using a Vectra 3 imaging system (Perkin Elmer) and quantified for co-labeling of eGFP and PV staining using inform-Tissue finder, advanced image analysis software or hand scored. At least 80 GFP positive cells were counted in each panel before determining the percentage of co-localization.

Figure 3A:
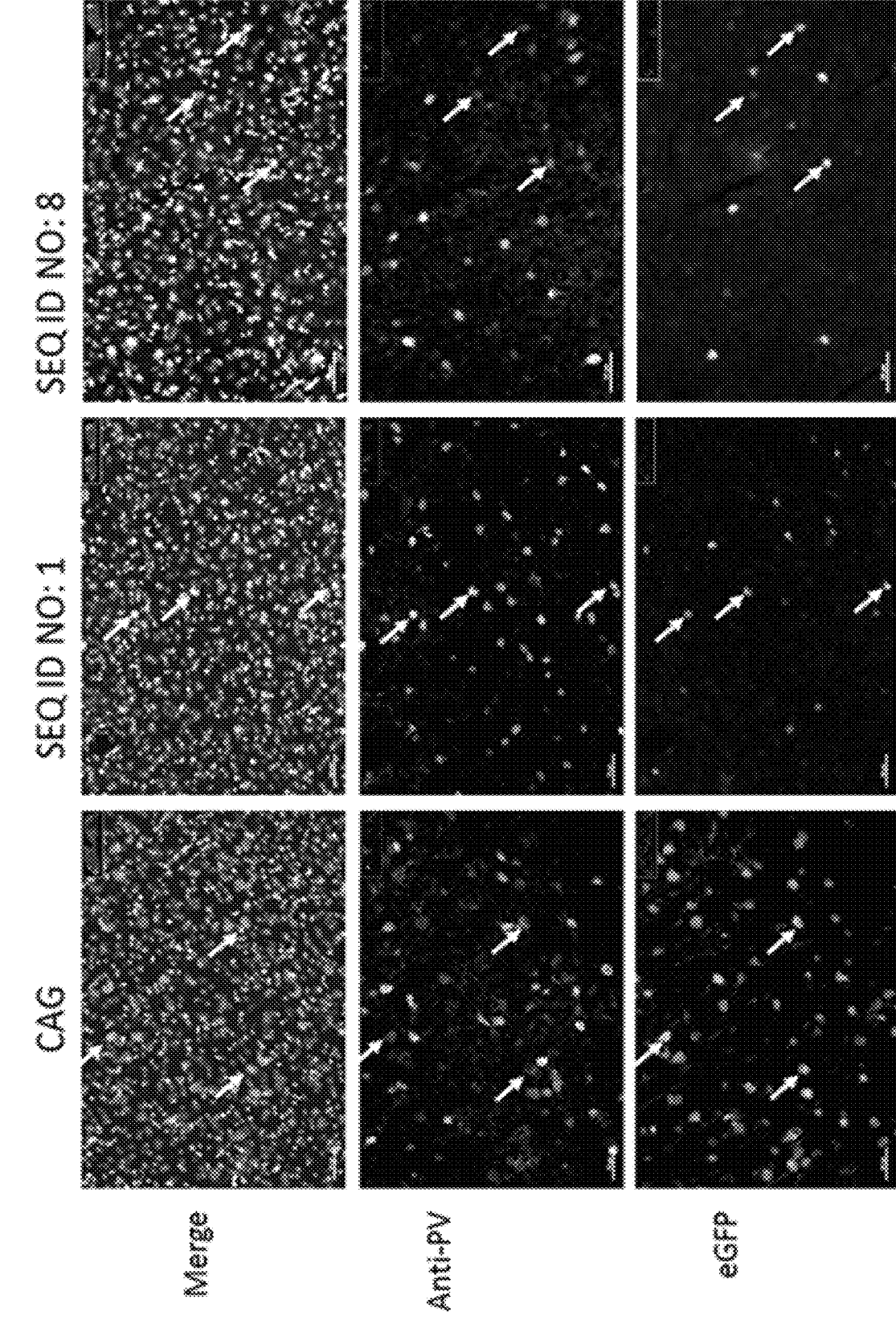
FIG. 3A illustrates immunofluorescence co-localization assay of CNS cells from pups following neonatal systemic injections of AAV9 comprising a eGFP transgene operably linked to a regulatory element comprising a sequence of SEQ ID NO: 1 or SEQ ID NO: 8. AAV9 comprising a eGFP transgene operably linked to CAG was used as a control. Lower row images illustrate eGFP-expressing (eGFP+) cells. Middle row images illustrate PV+ cells, which were stained with an anti-PV antibody. Top row images (merge) illustrate an overlay of PV+, eGFP+ fluorescence (with representative eGFP+ and PV+ cells which are shown as white or light grey cells indicated by arrowheads) and DAPI+.
Figure 3B:
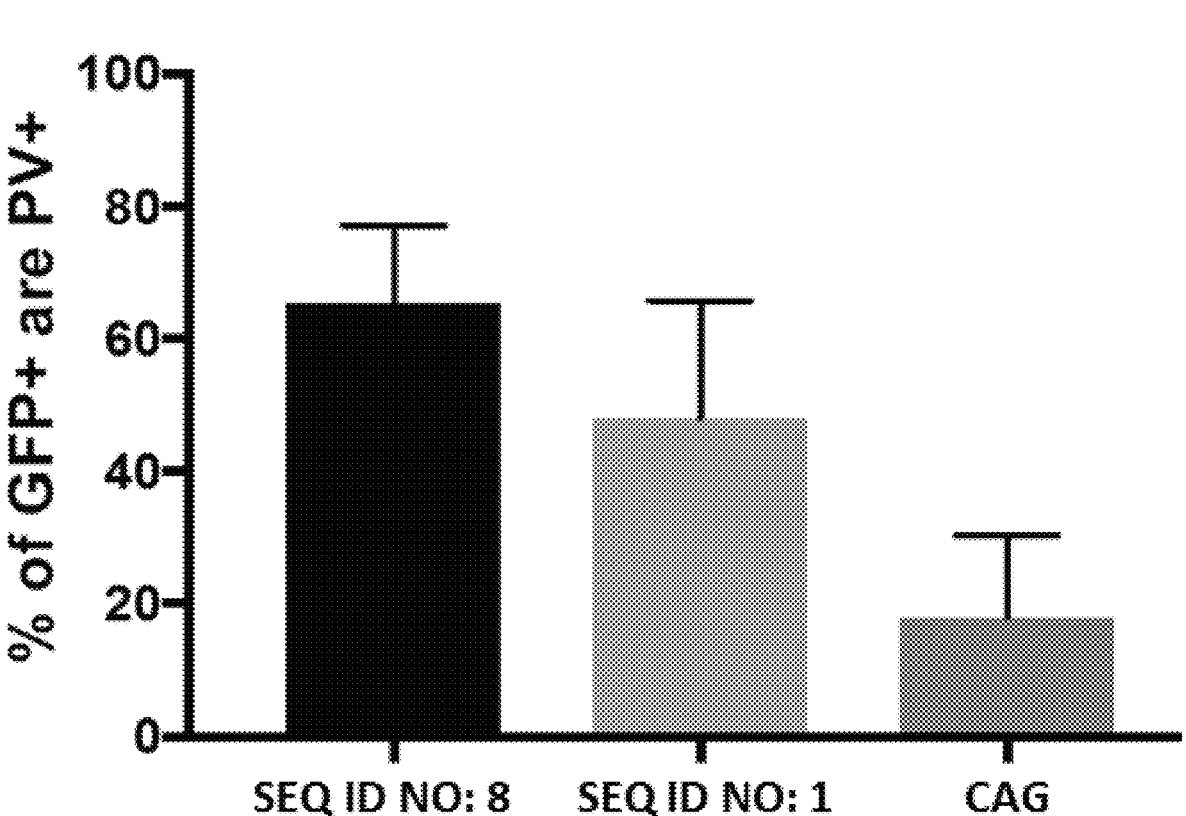
FIG. 3B illustrates the quantification of immunofluorescence co-localization studies illustrated in FIG. 3A, wherein selective expression in PV cells is expressed as the percentage of eGFP+ cells that were also PV+ in comparison to the CAG control, as measured by the immunofluorescence co-localization assay.
Figure 4A:
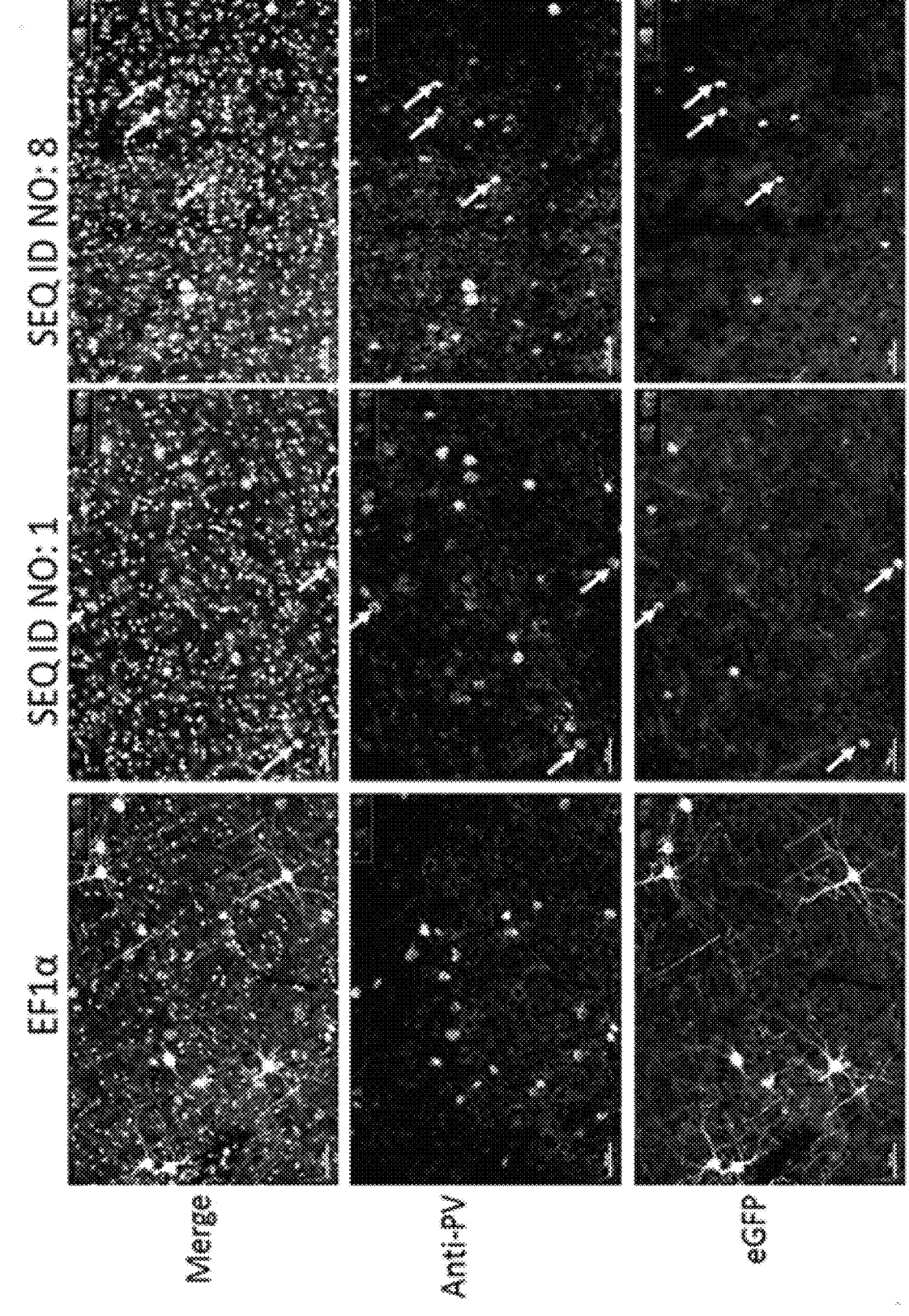
FIG. 4A illustrates immunofluorescence co-localization assay of CNS cells from adult mice following systemic injections of AAV9 comprising eGFP transgene operably linked to a regulatory element comprising a sequence of SEQ ID NO: 1 or SEQ ID NO: 8. AAV9 comprising a eGFP transgene operably linked to EF1α was used as a control. Lower row images illustrate eGFP+ cells. Middle row images illustrate PV+ cells, which were stained with an anti-PV antibody. Top row images (merge) illustrate an overlay of PV+ eGFP+ fluorescence (with representative eGFP+ and PV+ cells, or the white or light grey cells, indicated by arrowheads) and DAPI+.
Figure 4B:
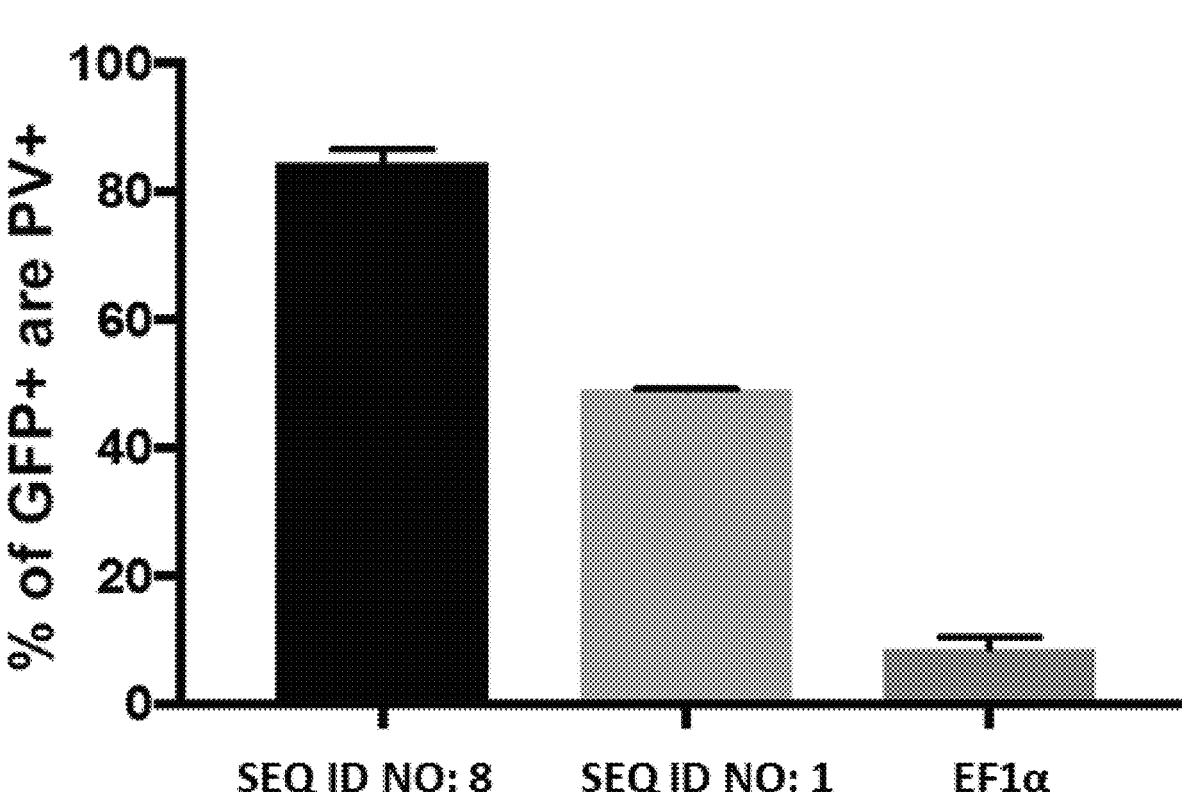
FIG. 4B illustrates the quantification of immunofluorescence co-localization studies illustrated in FIG. 4A, wherein selective expression in PV cells is expressed as the percentage of eGFP+ cells that were also PV+ in comparison to the EF1α control, as measured by the immunofluorescence co-localization assay.
Figure 5A:
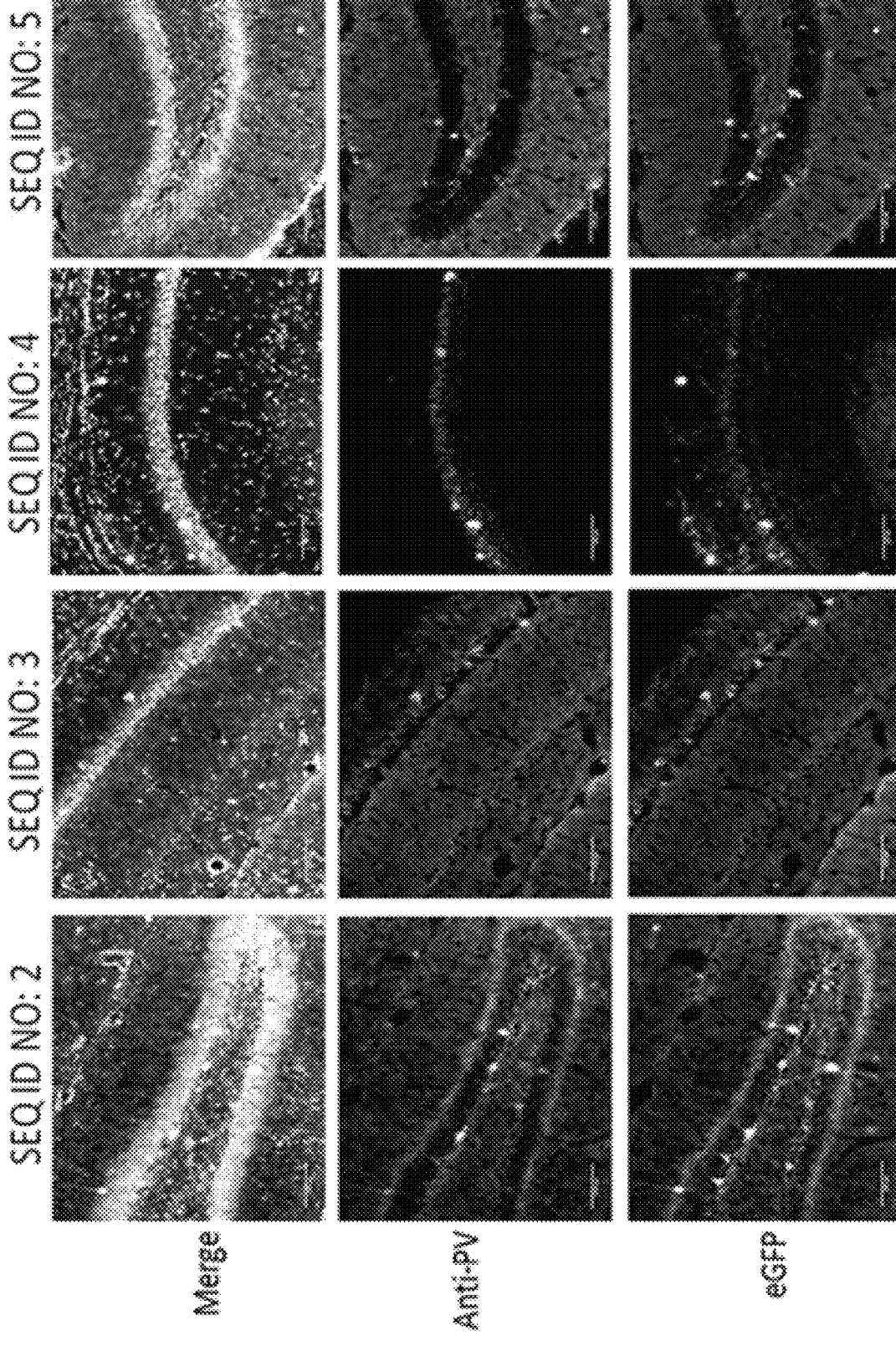
FIGS. 5A-5F illustrate immunofluorescence co-localization assay of CNS cells from adult mice following direct CNS injections of AAVDJ comprising eGFP transgene operably linked to a regulatory element comprising a sequence of SEQ ID NOS: 2-22. Lower row images illustrate eGFP+ cells. Middle row images illustrate PV cells that were stained with an anti-PV antibody. Top row images (merge) illustrate an overlay of PV+, eGFP+ fluorescence (with representative eGFP+ and PV+ cells, or the white or light grey cells, indicated by arrowheads) and DAPI+.
Figure 5B:
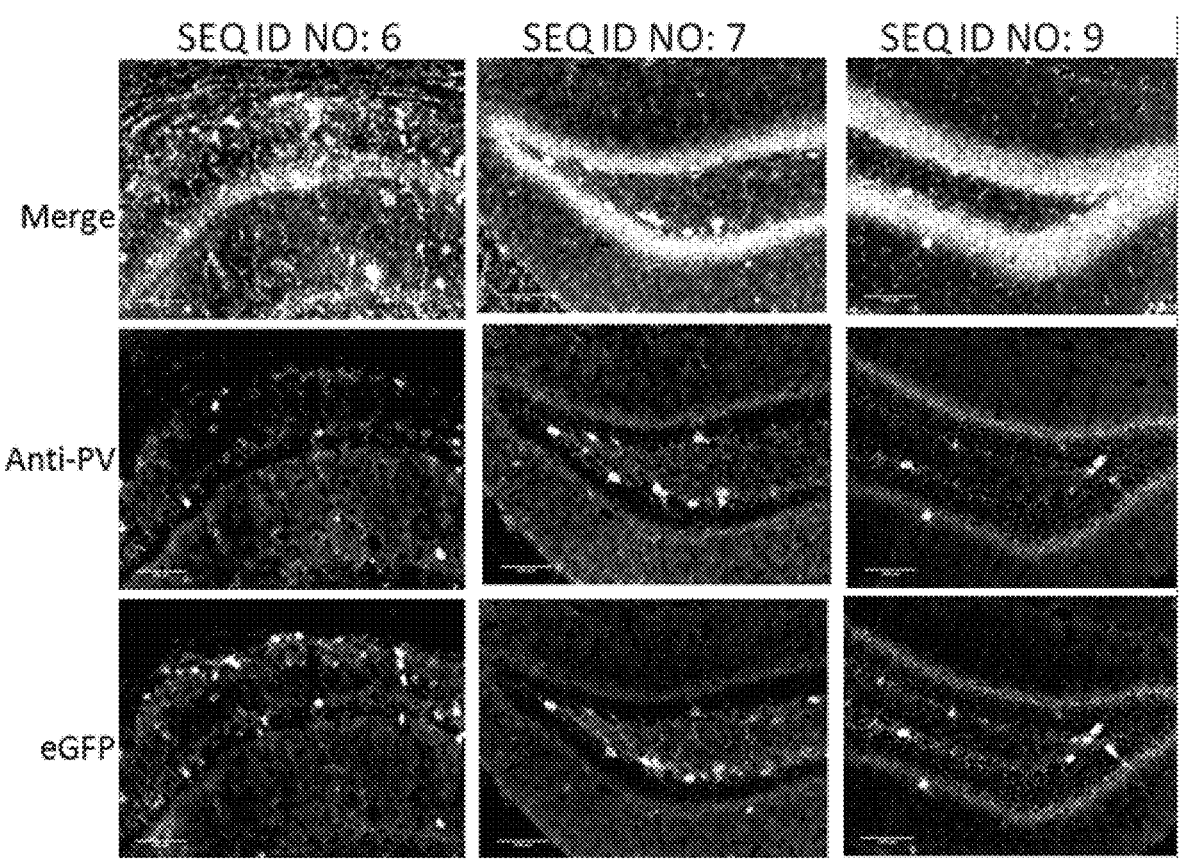
Figure 5C:
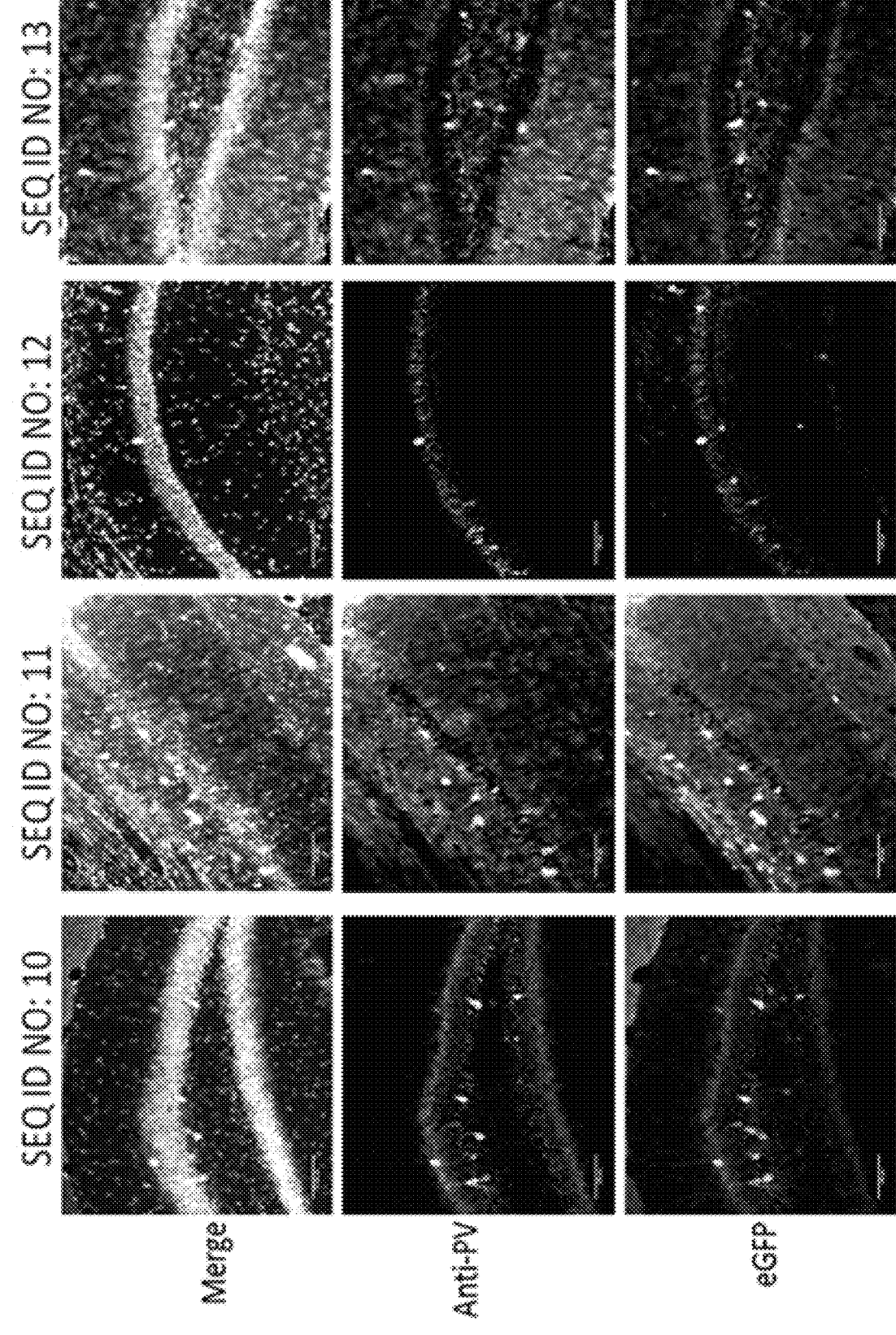
Figure 5D:
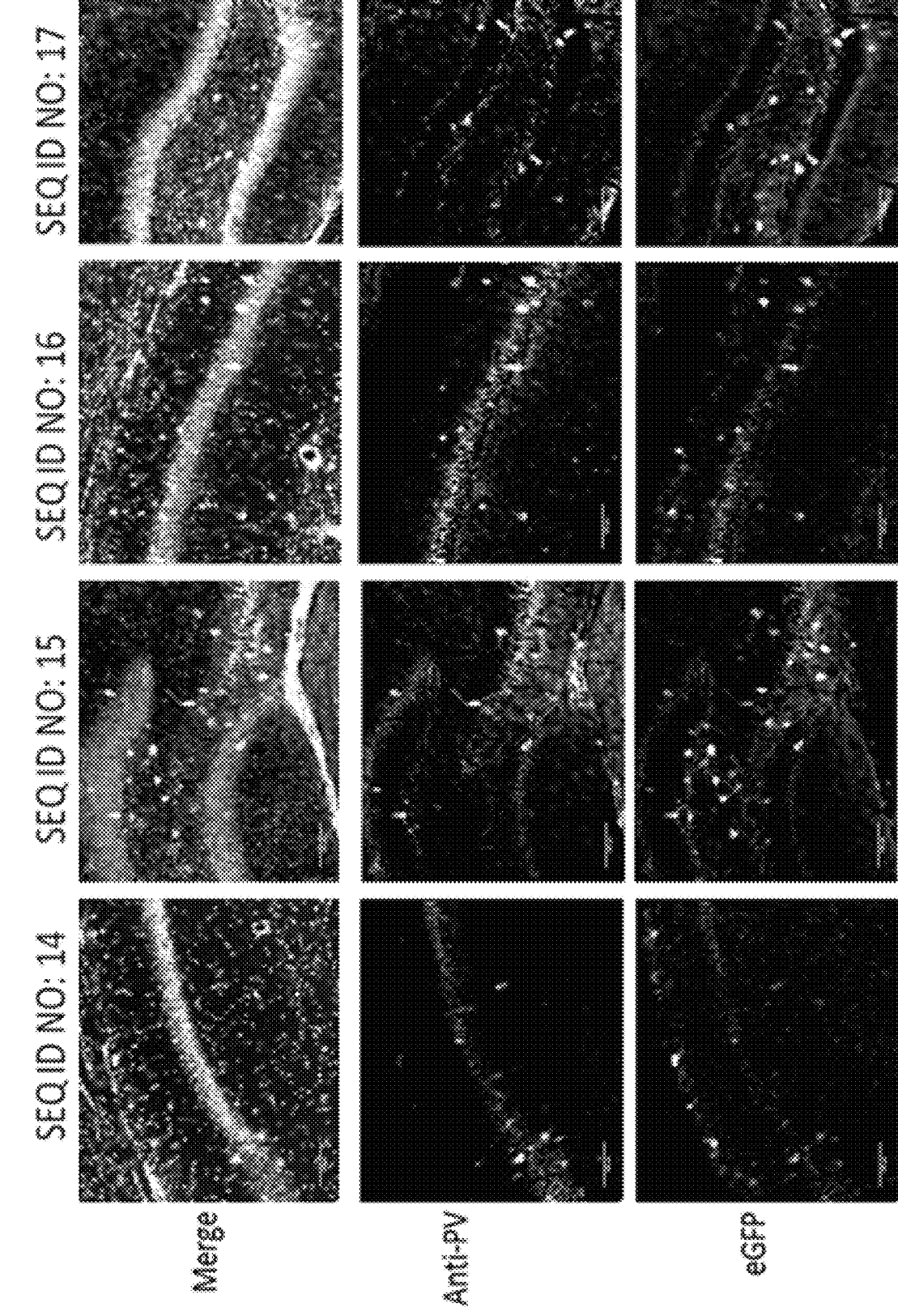
Figure 5E:
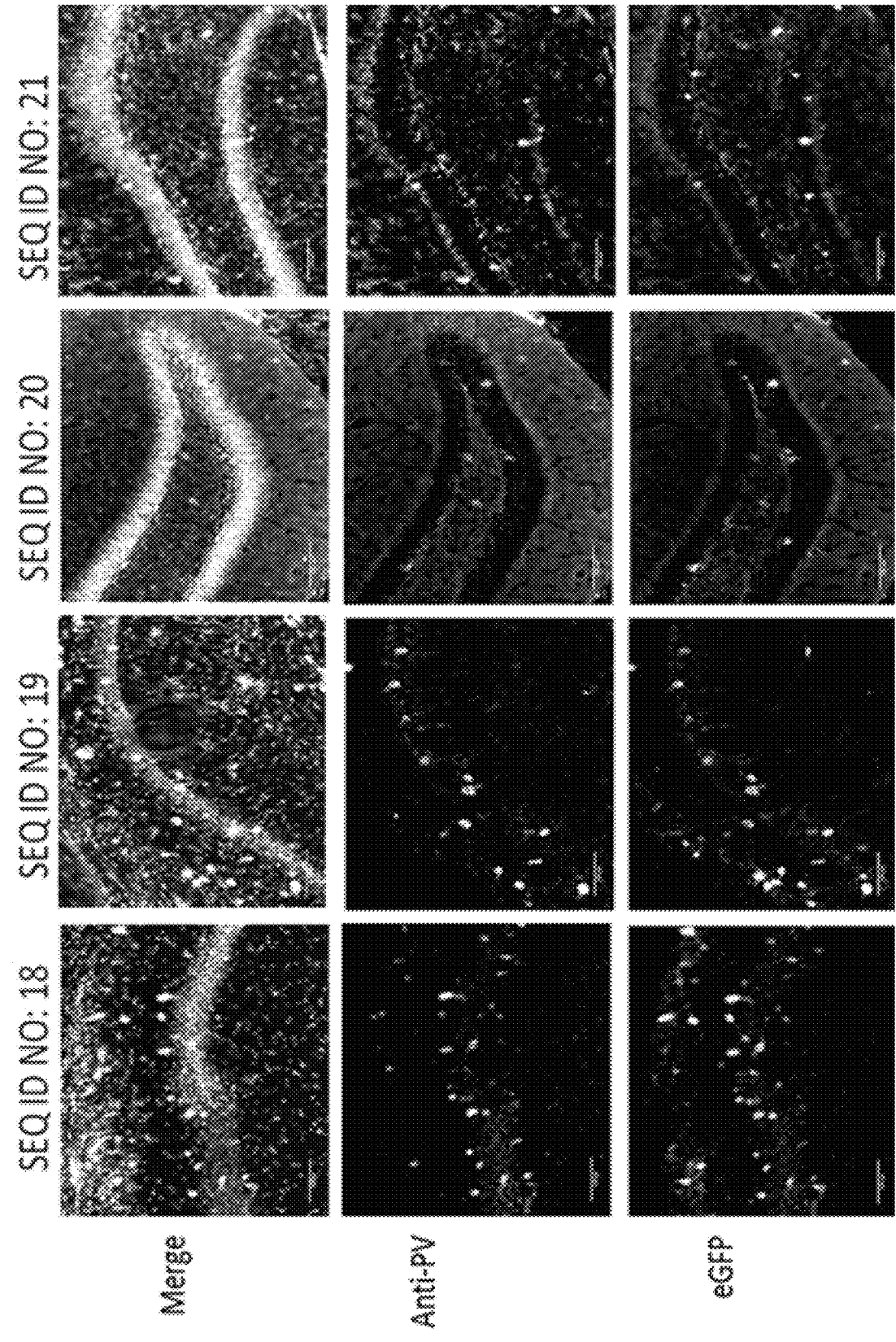
Figure 5F:
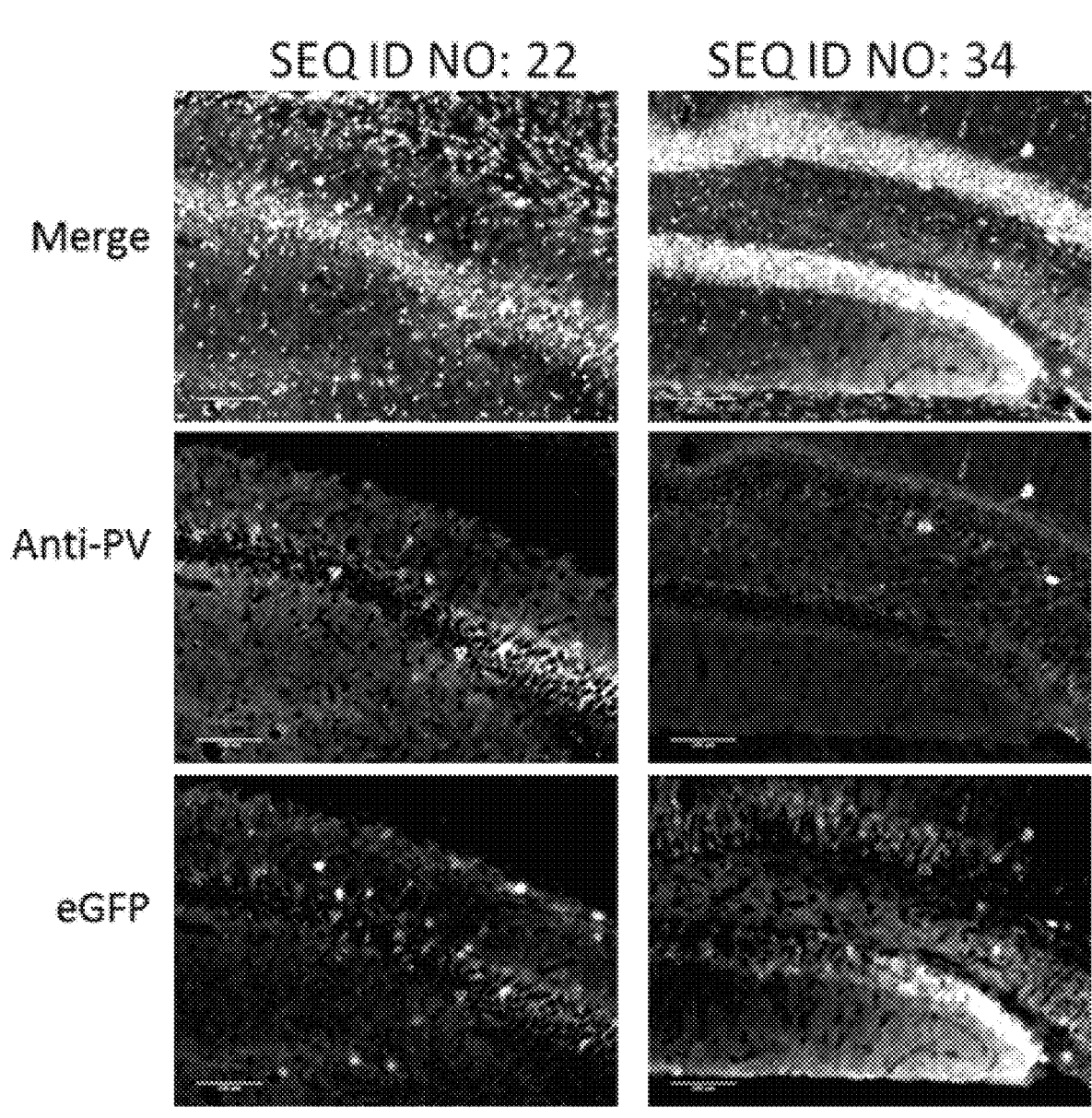

FIGS. 3A-3C illustrates the results of the immunohistochemistry experiments performed in pups after systemic AAV9 injections. FIGS. 4A-4C illustrates results of similar immunohistochemistry experiments performed in adult mice following AAV9 injections.

FIG. 3A illustrates the overlay of the immunohistochemistry experiments performed in pups after systemic AAV9 injections. FIG. 3B illustrates the quantification of the co-localization of the immunohistochemistry experiments, wherein selectivity for PV cells was measured as percentage of GFP+ cells that were also PV+, as compared to eGFP expression under the control of the CAG promoter.

FIG. 4A illustrates the overlay of the immunohistochemistry experiments performed in adult mice after systemic AAV9 injections. FIG. 4B illustrates the quantification of the co-localization of the immunohistochemistry experiments, wherein selectivity for PV cells was measured as percentage of GFP+ cells that were also PV+, as compared to eGFP expression under the control of the EF1α.

It is estimated that GABAergic neurons constitute about 20% of CNS, while PV cells constitute about 40% of GABAergic neurons, which means that PV cells make up approximately 8% of all neurons in the CNS. See, Pelkey, K A et al., 2017; and Lee, S. et al., 2010. Thus, one would predict that about 8% of the cells labeled by a non-selective regulatory element (e.g., CAG, EF1α, or a constitutive promoter) would be PV positive, or within this range. Therefore, expression in PV cells above 8% is indicative of increased selectivity in PV cells. Notably, AAV9 injections comprising regulatory element SEQ ID NO: 8 resulted in about 60% of cells as PV positive, which was 7.5 times higher than what was expected by the distribution of PV cells.

Figure 6:
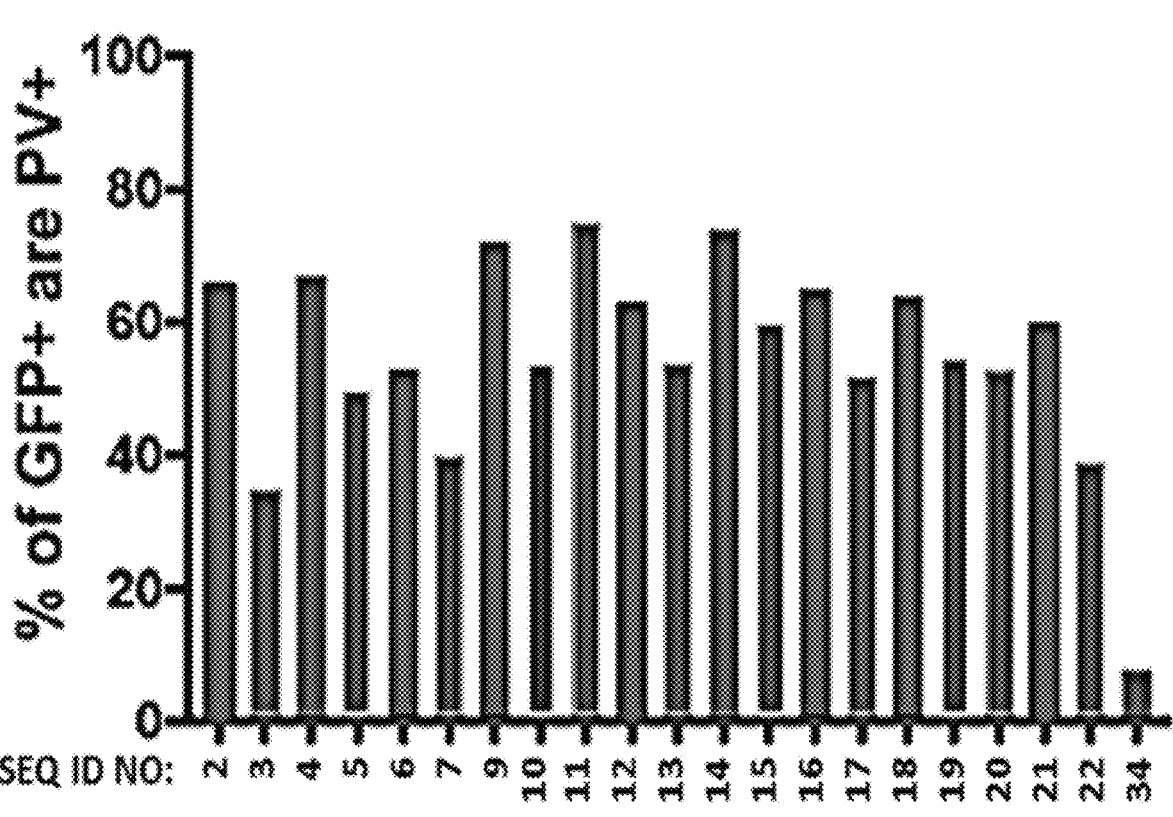
FIG. 6 illustrates the quantification of immunofluorescence co-localization studies illustrated in FIGS. 5A-5F, wherein selective expression in PV cells is expressed as the percentage of eGFP+ cells that were also PV+ in comparison to SEQ ID NO: 34, as measured by the immunofluorescence co-localization assay.

Similar immunohistochemistry experiments as described above were performed to determine the selective expression of additional regulatory elements, SEQ ID NOS: 2-7 and 9-22 as compared to a non-selective regulatory element having a sequence of SEQ ID NO: 34, except AAVDJ viral vector was used to deliver eGFP operably linked to a regulatory element into C57BL/6J (WT) mice. Such AAVDJ virus was injected directly into the CNS in the hippocampus of adult mice. At least 80 GFP positive cells were counted in each experiment before calculating the percentage of co-localization, or selectivity, as percentage of GFP positive cells that were also PV positive. FIGS. 5A-5F illustrate the fluorescence imaging used for determining co-localization, or selectivity, measured as percentage of eGFP positive cells that were also PV positive and in comparison to the signal of non-selective regulatory element SEQ ID NO: 34. Cells that were positive for a marker appear as white/gray cells in the images. Merge images illustrate the overlap between the corresponding eGFP and anti-PV images. Cells that were positive for both eGFP and PV appear as white/light gray cells in the merge image. FIG. 6 illustrates the quantification of the co-localization analysis, measured as percentage of eGFP+ cells that were also PV+.

Example 6

Treatment of Dravet Syndrome in Different Mouse Lines

Treatment of Dravet syndrome and/or symptoms thereof using the expression cassettes described herein can be tested in various mouse lines, such as B6(Cg)-Scn1a$^{tm1.1Dsf}$J as described above, Scn1a$^{tm1Kea}$, and Scn1a-R1470X mouse lines. These mouse lines are established mouse models for Dravet syndrome. Scn1a$^{tm1Kea}$ and Scn1a-R1470X mouse lines do not require CRE recombinase.

The Scn1a$^{tm1Kea}$ mouse (available from the Jackson Laboratory; described in Hawkins et al., Scientific Reports, vol. 7: 15327 (2017)) comprises a deletion of the first coding exon of SCN1A. Mice homozygous for the SCN1A knock-out allele are characterized by tremors, ataxia, seizures, and die by postnatal day 16. Heterozygous mice on the C57BL/6 background develop spontaneous seizures and die within weeks. Such mouse strain can be used to study safety and efficacy of treatment of epilepsy and Dravet syndrome. See, Miller et al., *Genes Brain Behav.* 2014 February; 13(2):163-72 for additional information.

The Scn1a-R1470X mouse is a knock-in mouse carrying a premature stop codon, R1407X, in exon 21 of the SCN1A gene. The same mutation has been identified as a pathogenic mutation in three unrelated SMEI patients. Scn1a$^{RX/RX}$ pups are characterized by recurrent spontaneous seizures at 12 postnatal days, including tonic-clonic and clonic seizures at 12-16 postnatal days, and rhythmic jerking movements and involuntary muscle contraction. See, Ogiwara et al., *Journal of Neuroscience*, May 30, 2007, 27 (22) 5903-5914 for additional information.

To test the compositions described herein, such as AAV gene therapy and treatment using such gene therapy. Dravet mice of each of the mouse strains described above and control mice (e.g., a wild-type mouse or an untreated Dravet mouse for the strain) are injected (e.g., administered by intraperitoneal injection) with AAVs expressing either eGFP or another reporter gene, or an expression cassette comprising one or more PV-selective REs (e.g., SEQ II) NOS: 1-32) as described herein operably linked to a transgene disclosed herein, which encodes SCN1A, SCN1B, or SCN2B, or any of SEQ ID NOS: 37-39, or a variant or functional fragment thereof. Following AAV injections, mouse survival is monitored over time. All mice are monitored daily for general health (e.g. weight, hydration, grooming, and mobility) and deaths were recorded. Telemetry implantation can be performed immediately after AAV injections (F20-EET, Data Sciences International). Electrocorticogram data can be recorded and monitored continuously for at least 14 days from 10 days after the surgery. All seizure events can be recorded for at least 14 days following AAV treatment, annotated with date, time start, time stop, duration, and severity score. A reduction in the frequency and/or duration of seizures following treatment with an AAV as described above as compared to the eGFP control or an untreated control is indicative of the efficacy of the gene therapy in reducing the symptoms and/or severity of Dravet syndrome.

After treatment of the mice with AAV, the expression levels of the transgene (e.g., SCN1A; SCN1B; SCN2B; a DNA binding protein, such as a transcriptional activator, that modulates an endogenous SCN1A, SCN1B, or SCN2B; any of SEQ ID NOS: 37-39; or any variant or functional fragment thereof) can be monitored over time using various PCR and/or sequencing methods to show AAV treatment can result in an increase in gene expression in PV cells. Northern blot analysis and in situ hybridization can also be used to analyze transgene expression in vivo. The level of the protein expressed can also be monitored after treatment to show that an increase in transgene expression correlates with an increase in the corresponding protein in vivo. Protein levels can be assayed using various methods, including, but not limited to, Western blot analysis, immunohistochemistry, immunofluorescence histochemistry, and/or ELISA assays. Formation of functional voltage-gated sodium ion channels can also be assayed using current-clamp analysis.

Hyperthermia-induced seizures can be evaluated to compare the wild-type mice and/or untreated Dravet mice with Dravet mice treated with AAV gene therapy comprising an expression cassette described herein (e.g., an expression cassette comprising one or more REs of this disclosure operably linked to a transgene of this disclosure, encoding SCN1A, SCN2A, SCN8A, SCN1B, SCN2B, a functional fragment thereof, or a DNA binding protein that modulates an endogenous SCN1A, SCN2A, SCN8A, SCN1B, or SCN2B). In such experiments, the core body temperature is monitored with a RET-3 rectal temperature probe (Physitemp Instruments, Inc., New Jersey, USA) and controlled by a heat lamp connected to a rodent temperature regulator (TCAT-2DF, Physitemp Instruments, Inc.) reconfigured with a Partlow 1160+controller (West Control Solutions, Brighton, UK). Body temperature is raised 0.5° C. every two minutes until the onset of the first clonic convulsion. As compared to the untreated Dravet mice, Dravet mice treated with an AAV gene therapy are expected to have a higher threshold temperature before the onset of first clonic convulsion and/or have a higher proportion of mice that remain seizure free at the maximum temperature tested.

Different doses of AAV comprising an expression cassette can also be administered to mice to determine the safety and efficacy profile of each gene therapy treatment. These preclinical studies can also inform the optimal dose(s) of the gene therapy to use for treating Dravet syndrome.

Example 7

Treatment of Alzheimer's Disease in Mouse

Female APP/PS1 and wild-type (WT) mice, which are bred at PSYCHOGENICS® and are established mouse model of Alzheimer's disease, can be used to study the safety and efficacy of the compositions described herein in treating Alzheimer's disease, comprising one or more PV-selective REs. APP/PS1 mice is describe above in Example 4.

APP/PS1 mice and non-transgenic controls are injected with either a control AAV vector expressing eGFP or a treatment AAV vector comprising one or more PV-selective REs disclosed herein, e.g., SEQ ID NOS: 1-32, operably linked to a transgene that is deficient or impaired in Alzheimer's disease, which encodes SCN1A, SCN2A, SCN8A, SCN1B, SCN2B, KV3.1, KV13, STXBP1, a DNA-binding protein that modulates an endogenous gene (e.g., SCN1A, SCN2A, SCN8A, SCN1B, SCN2B, KV3.1, KV3.3, or STXBP1), or any one of SEQ ID NOS: 37-43, or a functional fragment thereof.

Following AAV injections, mouse survival is monitored over time. All mice are monitored daily for general health (e.g. weight, hydration, grooming, and mobility) and deaths were recorded. After injections of the AAVs, mice are also implanted with an EET transmitter as described in Example 3 above. Brain activity can be recorded and monitored over 24 hours for at least 4 weeks after surgery. Electrocortico-gram data can be automatically analyzed, and power levels in the different frequency bands (50-100 Hz) can be compared across different groups: WT mice, untreated APP/PS1 mice, and AAV-treated APP/PS1 mice, each treated with an AAV gene therapy as described above. Increased high gamma power activity is associated with seizures in Alzheimer's patients and epilepsy patients. Thus, the untreated APP/PS1 mice are expected to show a higher level of high gamma power activity than the control mice, while this increase is expected to be absent or reduced in the treated mice, indicating an effective treatment with an AAV gene therapy.

After treatment of the mice with AAVs, the expression levels of the transgene can be monitored over time using various PCR and/or sequencing methods to show AAV treatment can result in an increase in endogenous expression of the transgene. Northern blot analysis and in situ hybrid-ization can also be used to analyze gene expression in vivo. The level of the protein expressed from the transgene can also be monitored after treatment to show an increase in gene expression correlates with an increase in protein levels. Protein level can be assayed using various methods, includ-ing, but not limited to, Western blot analysis, immunohis-tochemistry, and/or ELISA assays. Formation of functional voltage-gated sodium or potassium ion channels can also be assayed using current-clamp analysis.

Different doses of AAV comprising an expression cassette can also be administered to mice to determine the safety and efficacy profile of each gene therapy treatment. These pre-clinical studies can also inform the optimal dose(s) of the gene therapy to use for treating Alzheimer's disease.

---

What is claimed is:

1. A viral particle comprising a viral vector, wherein the viral vector comprises an expression cassette comprising a regulatory element operably linked to a heterologous transgene, wherein the regulatory element comprises a nucleic acid sequence with at least 95% identity to SEQ ID NO: 1 or 8, and wherein the expression cassette selectively increases expression of the heterologous transgene in parvalbumin (PV) neurons compared to non-PV cells.

2. The viral particle of claim 1, wherein the expression cassette further comprises an enhancer, a promoter, a stability element, a UTR, or a combination thereof.

3. The viral particle of claim 1, wherein the regulatory element comprises a nucleic acid sequence of SEQ ID NO: 1.

4. The viral particle of claim 1, wherein the regulatory element comprises a nucleic acid sequence of SEQ ID NO: 8.

5. The viral particle of claim 1, wherein the heterologous transgene encodes (a) an amino acid sequence having at least 95% identity to any one of SEQ ID NOS: 37-43, or (b) an amino acid sequence of any one of SEQ ID NOS: 37-43.

6. The viral particle of claim 1, wherein the heterologous transgene encodes a DNA binding protein.

7. The viral particle of claim 6, wherein the DNA binding protein modulates expression of an endogenous gene.

8. The viral particle of claim 7, wherein the endogenous gene is SCN1A, SCN2A, SCN8A, SCN1B, SCN2B, KV3.1, KV3.2, KV3.3, or STXBP1.

9. The viral particle of claim 1, wherein the viral vector is an adeno-associated virus (AAV) vector or a lentiviral vector.

10. The viral particle of claim 9, wherein the viral vector is the AAV vector and the viral particle is an AAV viral particle, and wherein the AAV viral particle has a serotype selected from the group consisting of AAV1, AAV2, AAV3, AAV4, AAV5, AAV6, AAV7, AAV8, AAV9, AAV10, AAV11, AAV12, rh10, AAV-DJ, avian AAV, bovine AAV, canine AAV, equine AAV, primate AAV, non-primate AAV, ovine AAV, and hybrids or variants thereof.

*     *     *     *     *